(12) United States Patent
Darwish et al.

(10) Patent No.: US 8,129,390 B2
(45) Date of Patent: Mar. 6, 2012

(54) CARBOXAMIDE, SULFONAMIDE AND AMINE COMPOUNDS AND METHODS FOR USING THE SAME

(75) Inventors: Ihab S. Darwish, San Carlos, CA (US); Jiaxin Yu, San Carlos, CA (US); Hui Hong, Palo Alto, CA (US); Rajinder Singh, Belmont, CA (US); Sambaiah Thota, Fremont, CA (US); Xiang Xu, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 571 days.

(21) Appl. No.: 12/334,201

(22) Filed: Dec. 12, 2008

(65) Prior Publication Data

US 2009/0163511 A1 Jun. 25, 2009

Related U.S. Application Data

(60) Provisional application No. 61/013,114, filed on Dec. 12, 2007, provisional application No. 61/013,124, filed on Dec. 12, 2007, provisional application No. 61/016,402, filed on Dec. 21, 2007, provisional application No. 61/016,405, filed on Dec. 21, 2007, provisional application No. 61/016,406, filed on Dec. 21, 2007, provisional application No. 61/078,209, filed on Jul. 3, 2008.

(51) Int. Cl.
*A61K 31/496* (2006.01)
*A61K 31/44* (2006.01)
*C07D 403/00* (2006.01)
*C07D 491/12* (2006.01)

(52) U.S. Cl. ............... 514/253.01; 514/292; 544/364; 546/87

(58) Field of Classification Search ............ 514/253.01, 514/292; 544/364; 546/87
See application file for complete search history.

(56) References Cited

U.S. PATENT DOCUMENTS

| | | | |
|---|---|---|---|
| 4,987,141 A | 1/1991 | Bushell et al. | |
| 6,172,232 B1 | 1/2001 | Stahrfeldt | |
| 6,472,405 B1 | 10/2002 | Fisher et al. | |
| 7,001,900 B2 | 2/2006 | Jacobsen et al. | |
| 7,208,491 B2 | 4/2007 | Fertig et al. | |
| 7,253,286 B2 | 8/2007 | Funahashi et al. | |
| 7,273,868 B2 | 9/2007 | Yamada et al. | |
| 2002/0183327 A1 | 12/2002 | Gerlach et al. | |
| 2004/0002513 A1 | 1/2004 | Mazurov et al. | |
| 2004/0023972 A1 | 2/2004 | Sundermann et al. | |
| 2005/0165049 A1 | 7/2005 | Hulme et al. | |
| 2005/0282864 A1 | 12/2005 | McArthur et al. | |
| 2007/0123515 A1 | 5/2007 | Nettekoven et al. | |
| 2007/0123525 A1 | 5/2007 | Nettekoven et al. | |
| 2007/0123526 A1 | 5/2007 | Nettekoven et al. | |

FOREIGN PATENT DOCUMENTS

| | | |
|---|---|---|
| EP | 1813613 | 8/2007 |
| GB | 2 327 675 | 3/1999 |
| WO | WO9736903 | 10/1997 |
| WO | WO0012074 | 3/2000 |
| WO | WO0059904 | 10/2000 |
| WO | WO0164639 | 9/2001 |
| WO | WO0200651 | 1/2002 |
| WO | WO02089749 | 11/2002 |
| WO | WO03018586 | 3/2003 |
| WO | WO03022856 | 3/2003 |
| WO | WO03070732 | 8/2003 |
| WO | WO03072578 | 9/2003 |
| WO | WO2004000820 | 12/2003 |
| WO | WO2004054974 | 7/2004 |
| WO | WO2004085409 | 10/2004 |
| WO | WO2004111003 | 12/2004 |
| WO | WO2005002552 | 1/2005 |
| WO | WO2005020921 | 3/2005 |
| WO | WO2005061442 | 7/2005 |
| WO | WO2005116000 | 12/2005 |
| WO | WO2005117865 | 12/2005 |
| WO | WO2006045416 | 5/2006 |
| WO | WO2006046916 | 5/2006 |
| WO | WO2006058905 | 6/2006 |
| WO | WO2006064355 | 6/2006 |
| WO | WO2006067462 | 6/2006 |
| WO | WO2006076131 | 7/2006 |
| WO | WO2006094235 | 9/2006 |
| WO | WO2006099379 | 9/2006 |
| WO | WO2006101434 | 9/2006 |

(Continued)

OTHER PUBLICATIONS

Copending U.S. Appl. No. 11/963,742, filed Dec. 21, 2007.

(Continued)

*Primary Examiner* — Rebecca Anderson
*Assistant Examiner* — Samantha Shterengarts
(74) *Attorney, Agent, or Firm* — Travis Young; McDonnell Boehnen Hulbert & Berghoff LLP

(57) ABSTRACT

Disclosed are carboxamide, sulfonamide and amine compounds, as well as pharmaceutical compositions and methods of use. One embodiment is a compound having the structure

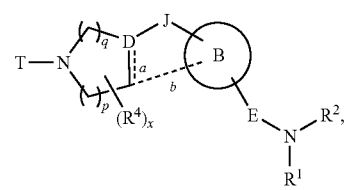

in which $R^1$, $R^2$, $R^4$, D, E, J, T, p, q and x are as described herein. In certain embodiments, a compound disclosed herein activates the AMPK pathway, and can be used to treat metabolism-related disorders and conditions.

53 Claims, No Drawings

FOREIGN PATENT DOCUMENTS

| | | |
|---|---|---|
| WO | WO2006114313 | 11/2006 |
| WO | WO2007005951 | 1/2007 |
| WO | WO2007075688 | 7/2007 |
| WO | WO2007087548 | 8/2007 |
| WO | WO2007087549 | 8/2007 |
| WO | WO2007098086 | 8/2007 |
| WO | WO2007099423 | 9/2007 |
| WO | WO2007122482 | 11/2007 |
| WO | WO2007143823 | 12/2007 |
| WO | WO2007143824 | 12/2007 |
| WO | WO2008017685 | 2/2008 |
| WO | WO2008083124 | 7/2008 |
| WO | WO2008133975 | 11/2008 |

OTHER PUBLICATIONS

Copending U.S. Appl. No. 12/272,581, filed Nov. 17, 2008.
Copending U.S. Appl. No. 12/428,334, filed Apr. 22, 2008.
International Search Report and Written Opinion in PCT/US2008/086673.
CAS Registry Nos. 896885-08-8; 896884-87-0; 896870-69-2; and 896870-65-8, report generated Dec. 10, 2007.
CAS Registry Nos. 894782-16-2; 894780-97-3; 894780-86-0; 894780-85-9; 894780-83-7; and 894779-82-9, report generated Dec. 10, 2007.
CAS Registry Nos. 197893-73-5; 197893-70-2; 197893-61-1; 197892-93-6; 197890-89-4; 197890-86-1; 197890-77-0, report generated Dec. 10, 2007.
CAS Registry Nos. 197893-74-6 and 197890-90-7, report generated Dec. 10, 2007.

CARBOXAMIDE, SULFONAMIDE AND AMINE COMPOUNDS AND METHODS FOR USING THE SAME

CROSS-REFERENCE TO RELATED APPLICATIONS

This application claims the benefit of the earlier filing dates of U.S. Provisional Patent Application Ser. No. 61/013,114, filed Dec. 12, 2007; Ser. No. 61/013,124, filed Dec. 12, 2007; Ser. No. 61/016,402, filed Dec. 21, 2007; Ser. No. 61/016,405, filed Dec. 21, 2007; Ser. No. 61/016,406, filed Dec. 21, 2007; and Ser. No. 61/078,209, filed Jul. 3, 2008, each of which is hereby incorporated herein by reference in its entirety.

BACKGROUND

1. Field

This disclosure relates generally to compounds, pharmaceutical compositions and methods of use of the compounds and compositions containing them. This disclosure relates more particularly to certain carboxamide, sulfonamide and amine compounds and pharmaceutical compositions thereof, and to methods of treating and preventing metabolic disorders such as type II diabetes, atherosclerosis and cardiovascular disease using certain carboxamide, sulfonamide and amine compounds.

2. Technical Background

Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptors, increase endogenous adiponectin production in humans.

Adiponectin binds its receptors in liver and skeletal muscle and thereby activates the 5'-AMP-activated protein kinase (AMPK) pathway. Adiponectin receptors 1 and 2 are membrane-bound proteins found in skeletal muscle and liver tissue. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Adiponectin improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, adiponectin decreases glycogen concentration by reducing the activity of glycogen synthase. Adiponectin also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis. What is needed are compounds, pharmaceutical compositions and methods of using them to treat disease states associated with circulating adiponectin levels, such as type II diabetes, atherosclerosis and cardiovascular disease.

SUMMARY

Disclosed herein are compounds having structural formula (I)

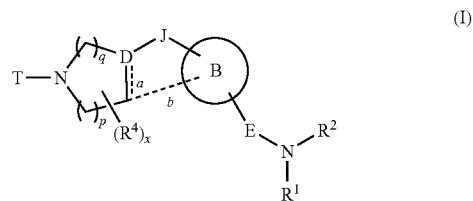

and pharmaceutically acceptable salts, prodrugs and N-oxides thereof (and solvates and hydrates thereof), wherein "B" represents -(aryl or heteroaryl)- substituted by w $R^3$ and k $R^{14}$;

the dotted line denoted by "b" is absent, a single bond or a double bond;

the dotted line denoted by "a" is a bond or absent, provided that if the dotted line denoted by "b" is a double bond, then the dotted line denoted by "a" is absent;

D is a carbon or N when the dotted line denoted by "a" is absent, and a carbon when the dotted line denoted by "a" is a bond;

J is —O—, —N($R^{38}$)—, —CH$_2$—, —CH($R^{26}$)— or —C($R^{26}$)$_2$—;

E is —C(O)—, —S(O)$_2$— or a single bond;

$R^1$ is H, —(C$_1$-C$_4$ alkyl), —C(O)—(C$_1$-C$_4$ alkyl) or —C(O)O—(C$_1$-C$_4$ alkyl);

$R^2$ is -Hca, -Cak-N($R^9$)-G-$R^{22}$ or —(C$_2$-C$_8$ alkyl)-N($R^9$)—$R^{24}$ in which one or two carbons of the (C$_2$-C$_8$ alkyl) are optionally replaced by —O—, —S— or —N($R^9$)— and $R^{24}$ is —$R^{23}$, -G-$R^{23}$ or —C(O)O—(C$_1$-C$_6$ alkyl), provided that two consecutive carbons of the (C$_2$-C$_8$ alkyl) are not replaced by —O—;

each $R^3$ is substituted on a benzo, pyrido or pyrazino carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

w is 0, 1, 2 or 3;

each $R^{14}$ is substituted on a non-benzo, non pyrido, non-pyrazino carbon of the ring system denoted by "B", and is independently selected from —(C$_1$-C$_6$ alkyl), —(C$_1$-C$_6$ halooalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

k is 0, 1 or 2;

each $R^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^4$ on the same carbon optionally combine to form oxo;

x is 0, 1, 2, 3 or 4;
p is 0, 1, 2, 3 or 4;
q is 0, 1, 2, 3 or 4;
the sum of p and q is 1, 2, 3 or 4;

T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$ or

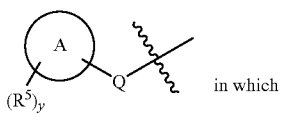 in which

Q is —S(O)$_2$—, L or (C$_0$-C$_3$ alkyl)-, in which each carbon of the —(C$_0$-C$_3$ alkyl)- is optionally and independently substituted with one or two R$^{16}$;

the ring system denoted by "A" is heteroaryl, aryl, cycloalkyl or heterocycloalkyl;

each R$^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN; and y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O—, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each R$^6$, R$^7$, R$^8$ and R$^{10}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), each R$^9$ is independently selected from —H, —(C$_1$-C$_4$ alkyl), —C(O)—(C$_1$-C$_4$ alkyl) and —C(O)O—(C$_1$-C$_4$ alkyl), each G is independently -S(O)$_2$—, L or —(C$_0$-C$_3$ alkyl)-, in which each carbon of the —(C$_0$-C$_3$ alkyl)- is optionally and independently substituted with one or two R$^{16}$, each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo, each R$^{26}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{26}$ on the same carbon combine to form oxo, each R$^{38}$ is independently selected from —H, —(C$_1$-C$_4$ alkyl), —C(O)—(C$_1$-C$_4$ alkyl) and —C(O)O—(C$_1$-C$_4$ alkyl), each R$^{22}$ and R$^{23}$ is independently Ar or Het,
each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.

Also disclosed herein are pharmaceutical compositions. Examples of such compositions include those having at least one pharmaceutically acceptable carrier, diluent or excipient; and a compound, pharmaceutically acceptable salt, prodrug or N-oxide (or solvate or hydrate) described above.

Another aspect of the present disclosure includes methods for modulating metabolism in subjects. Accordingly, also disclosed are methods for treating metabolic disorders using the presently disclosed compounds and pharmaceutical compositions.

DETAILED DESCRIPTION

One aspect of the disclosure provides compounds having structural formula (I):

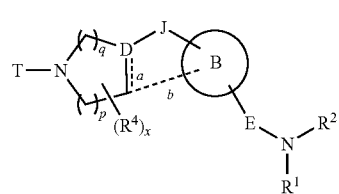

(I)

and pharmaceutically acceptable salts, prodrugs and N-oxides thereof (and solvates and hydrates thereof), in which "B" represents -(aryl or heteroaryl)- substituted by w R$^3$ and k R$^{14}$;

the dotted line denoted by "b" is absent, a single bond or a double bond;

the dotted line denoted by "a" is a bond or absent, provided that if the dotted line denoted by "b" is a double bond, then the dotted line denoted by "a" is absent;

D is a carbon or N when the dotted line denoted by "a" is absent, and a carbon when the dotted line denoted by "a" is a bond;

J is —O—, —N(R$^{38}$)—, —CH$_2$—, —CH(R$^{26}$)— or —C(R$^{26}$)$_2$—;

E is —C(O)—, —S(O)$_2$— or a single bond, provided that when "B" is phenyl, J is —O— and D is a carbon, E is not —C(O)—;

R$^1$ is H, —(C$_1$-C$_4$ alkyl), —C(O)—(C$_1$-C$_4$ alkyl) or —C(O)O—(C$_1$-C$_4$ alkyl);

R$^2$ is -Hca, -Cak-N(R$^9$)-G-R$^{22}$ or —(C$_2$-C$_8$ alkyl)-N(R$^9$)—R$^{24}$ in which one or two carbons of the (C$_2$-C$_8$ alkyl) are optionally replaced by —O—, —S— or —N(R$^9$)— and R$^{24}$ is —R$^{23}$, -G-R$^2$, or —C(O)O—(C$_1$-C$_6$ alkyl), provided that two consecutive carbons of the (C$_2$-C$_8$ alkyl) are not replaced by —O—;

each $R^3$ is substituted on a benzo, pyrido or pyrazino carbon of the ring system denoted by "B" and is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;

w is 0, 1, 2 or 3;

each $R^{14}$ is substituted on a non-benzo, non-pyrido, non-pyrazino carbon of the ring system denoted by "B", and is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;

k is 0, 1 or 2;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo;

x is 0, 1, 2, 3 or 4;

p is 0, 1, 2, 3 or 4;

q is 0, 1, 2, 3 or 4;

the sum of p and q is 1, 2, 3 or 4;

T is —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$ or

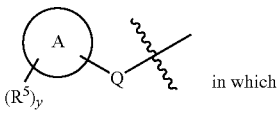

in which

Q is —S(O)$_2$—, L or —($C_0$-$C_3$ alkyl)-, in which each carbon of the —($C_0$-$C_3$ alkyl)- is optionally and independently substituted with one or two $R^{16}$;

the ring system denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, —($C_0$-$C_6$ alkyl)-C(O)$R^{10}$, -halogen, —$NO_2$ and —CN; and y is 0, 1, 2, 3 or 4;

in which each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9$SO$_2$—, —SO$_2NR^9$— and —$NR^9$SO$_2NR^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each G is independently —S(O)$_2$—, L or —($C_0$-$C_3$ alkyl)-, in which each carbon of the —($C_0$-$C_3$ alkyl)- is optionally and independently substituted with one or two $R^{16}$, or each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and optionally two of $R^{16}$ on the same carbon combine to form oxo, each $R^{26}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and optionally two of $R^{26}$ on the same carbon combine to form oxo, each $R^{38}$ is independently selected from —H, —($C_1$-$C_4$ alkyl), —C(O)—($C_1$-$C_4$ alkyl) and —C(O)O—($C_1$-$C_4$ alkyl), each $R^{22}$ and $R^{23}$ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

In certain embodiments of the presently disclosed compounds of structural formula (I), the compound is not 5-methyl-N,2-bis(tetrahydro-2H-pyran-4-yl)-2,3,4,5-tetrahydro-1H-pyrido[4,3-b]indole-8-carboxamide or 5-methyl-2-(tetrahydro-2H-pyran-4-yl)-N-(tetrahydrothiophen-2-yl)-2,3,4,5-tetrahydro-1H-pyrido[4,3-b]indole-8-carboxamide S,S-dioxide.

In certain embodiments of the presently disclosed compounds of structural formula (I), J is —O— or —N($R^{38}$)—. In certain such embodiments, D can be, for example, a carbon (for example, it is CH or C substituted with one of the x $R^4$ groups when the bond denoted by "a" is absent, or C when the bond denoted by "a" is present). In other embodiments of the presently disclosed compounds of structural formula (I), J is —$CH_2$—, —CH($R^{26}$)— or —C($R^{26}$)$_2$—, for example, —$CH_2$—. In certain such embodiments, D can be, for example, N.

In certain embodiments of the presently disclosed compounds of structural formula (I), $R^{38}$ is —H. In other embodiments, $R^{38}$ is —($C_1$-$C_4$ alkyl), for example methyl, ethyl or propyl. In other embodiments, $R^{38}$ is —C(O)—($C_1$-$C_4$ alkyl), for example acetyl. In other embodiments, $R^{38}$ is —C(O)—O—($C_1$-$C_4$ alkyl)-, for example —C(O)—O-t-butyl. In certain embodiments, no alkyl of $R^{38}$ is substituted with an aryl-, heteroaryl-, cycloalkyl- or heterocycloalkyl-containing group.

In certain embodiments of the presently disclosed compounds of structural formula (I), each $R^{26}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{26}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}$$R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, each $R^{26}$ is methyl, ethyl, propyl, or two $R^{26}$ come together to form oxo.

In certain embodiments of the presently disclosed compounds of structural formula (I) as described above, the dotted line denoted by "b" is absent. In other embodiments, the dotted line denoted by "b" is a single bond; in one such embodiment, the dotted line denoted by "a" is a bond (thereby forming a double bond between D and the adjacent carbon).

In certain embodiments of the presently disclosed compounds of structural formula (I), E is —C(O)—. In other embodiments, E is —S(O)$_2$—

In certain embodiments of the presently disclosed compounds of structural formula (I), "B" represents

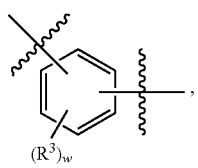

the dotted line denoted by "b" is a single bond, the dotted line denoted by "a" is a bond, k is 0, J is —N($R^{38}$)— and D is a carbon. In one such embodiment, E is —C(O)—.

In other embodiments of the presently disclosed compounds of structural formula (I), "B" represents

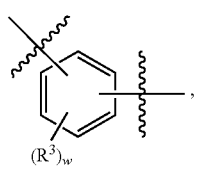

the dotted line denoted by "b" is absent, the dotted line denoted by "a" is absent, k is 0, J is —N($R^{38}$)— and D is a carbon. In one such embodiment, E is —C(O)—.

In other embodiments of the presently disclosed compounds of structural formula (I), "B" represents

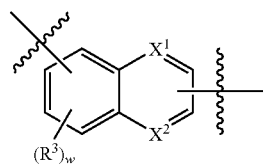

in which $X^1$ and $X^2$ are independently a carbon (for example, CH or C substituted with one of the w $R^3$ groups) or N, and k is 0. In one such embodiment, E is —C(O)—. In certain embodiments, one of $X^1$ and $X^2$ is N and the other is a carbon. In other embodiments, both $X^1$ and $X^2$ are a carbon. Floating bonds indicate attachment on any carbon of the ring system. In some embodiments, for example, the J moiety is on one ring of the ring system, and the E moiety is on the other ring of the naphthalene, and any $R^3$ groups can be on either ring of the fused ring system.

In other embodiments of the presently disclosed compounds of structural formula (I), "B" represents

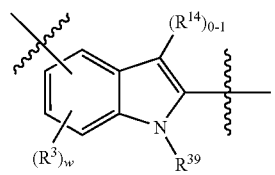

in which $R^{39}$ is H, —($C_1$-$C_4$ alkyl), —C(O)—($C_1$-$C_4$ alkyl) or —C(O)O—($C_1$-$C_4$ alkyl). In certain such embodiments, E is —C(O)—. In certain embodiments, one $R^{14}$ can be substituted on the pyrrolo carbon. In one such embodiment, $R^{14}$ is selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, $R^{14}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}$$R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. $R^{14}$ can be, for example, halo (e.g., —Cl or —F), cyano, unsubstituted —($C_1$-$C_4$ alkyl) (e.g., methyl or ethyl), or unsubstituted —($C_1$-$C_4$ haloakyl) (e.g., difluoromethyl, trifluoromethyl and the like). In certain embodiments, $R^{14}$ is H or methyl; in others, $R^{14}$ is halo (e.g., Cl). In other embodiments, no $R^{14}$ is substituted on the pyrrolo carbon.

In certain embodiments of the presently disclosed compounds of structural formula (I), T is

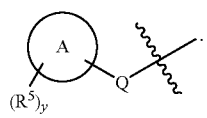

In such embodiments, Q is —S(O)$_2$—, L or —(C$_0$-C$_3$ alkyl)- in which each carbon of the (C$_0$-C$_3$ alkyl) is optionally and independently substituted with one or two R$^{16}$, in which each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo. In certain embodiments, each R$^{16}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each R$^{16}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one R$^{16}$ or an oxo substituted thereon. Q can be, for example, an unsubstituted —(C$_0$-C$_3$ alkyl)-. In other embodiments, Q is a (C$_1$-C$_3$ alkyl) having as its only substitution a single oxo group. For example, in certain embodiments, Q is —CH$_2$—; a single bond; —S(O)$_2$—; —C(O)—; or —CH(CH$_3$)—.

In certain embodiments of the compounds of structural formula (I), the

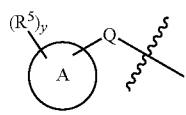

moiety is

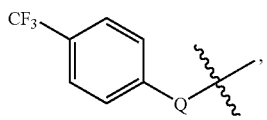

for example, p-(trifluoromethyl)phenyl. In other embodiments, the

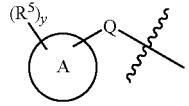

moiety is

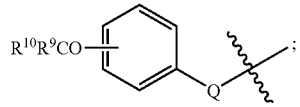

n one such embodiment, Q is a single bond.

The number of substituents on the ring system denoted by "A", y, is 0, 1, 2, 3 or 4. For example, in some embodiments of the presently disclosed compounds of structural formula (I), y is 0, 1, 2 or 3, such as 1. In one embodiment, y is not zero and at least one R$^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)-Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formula (I), each R$^5$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^5$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group.

In one embodiment of the compounds of structural formula (I), y is 0.

In the presently disclosed compounds of structural formula (I), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —(C$_0$-C$_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —$S(O)_2$—; —C(O)—; or —$CH(CH_3)$—.

For example, in certain embodiments of the presently disclosed compounds of structural formula (I), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —$C(O)CH_3$, —C(O)OH, —$C(O)NH_2$, trifluoromethyl, difluoromethyl, difluoromethoxy or trifluoromethoxy. In another embodiment, the

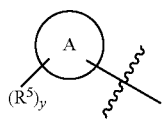

moiety is a 3,4-dihalophenyl.

In another embodiment of the presently disclosed compounds of structural formula (I), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —$CH_2$—; a single bond; —$S(O)_2$—; —C(O)—; or —$CH(CH_3)$—.

In one embodiment of the presently disclosed compounds, the compound has structural formula (II):

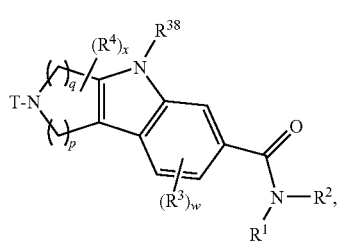

(II)

in which the variables are defined as described above with reference to structural formula (I). In certain embodiments, $R^{38}$ is not H. For example, $R^{38}$ can in one embodiment be methyl, ethyl or propyl. In another embodiment, $R^{38}$ can be acetyl. In other embodiments, $R^{38}$ is H.

In one embodiment of the presently disclosed compounds, the compound has structural formula (III):

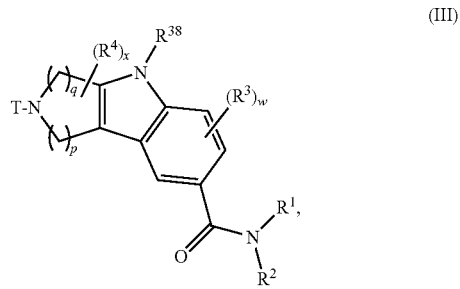

(III)

in which the variables are defined as described above with reference to structural formula (I). In certain embodiments, $R^{38}$ is not H. For example, $R^{38}$ can in one embodiment be methyl, ethyl or propyl. In another embodiment, $R^{38}$ can be acetyl. In other embodiments, $R^{38}$ is H.

In another embodiment of the presently disclosed compounds, the compound has structural formula (IV):

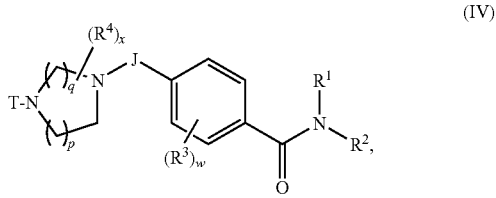

(IV)

in which k is 0, q is 1, 2, 3 or 4, J is —$CH_2$—, —$CH(R^{26})$— or —$C(R^{26})_2$— (e.g., —$CH_2$—), and all other variables are defined as described above with reference to structural formula (I).

In another embodiment of the presently disclosed compounds, the compound has structural formula (V):

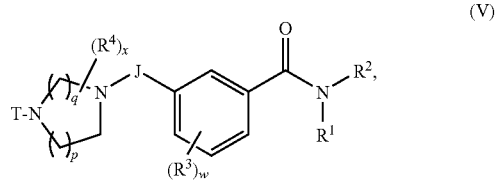

(V)

in which k is 0, q is 1, 2, 3 or 4, J is —$CH_2$—, —$CH(R^{26})$— or —$C(R^{26})_2$— (e.g., —$CH_2$—), and all other variables are defined as described above with reference to structural formula (I).

In certain embodiments according to structural formulae (I)-(V), the sum of p and q is 2 or 3. For example, in one embodiment, the sum of p and q is 2 (e.g., p is 1 and q is 1). In another embodiment, the sum of p and q is 3 (e.g., p is 1 and q is 2).

In another embodiment of the presently disclosed compounds, the compound has structural formula (VI):

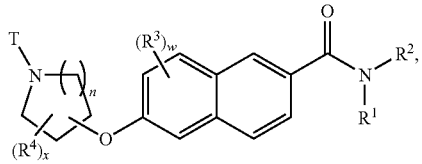
(VI)

in which k is 0, n is 0, 1, 2 or 3, and all other variables are defined as described above with reference to structural formula (I).

In another embodiment of the presently disclosed compounds, the compound has structural formula (VII):

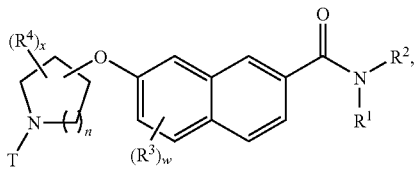
(VII)

in which k is 0, n is 0, 1, 2 or 3, and all other variables are defined as described above with reference to structural formula (I).

In another embodiment of the presently disclosed compounds, the compound has structural formula (VIII):

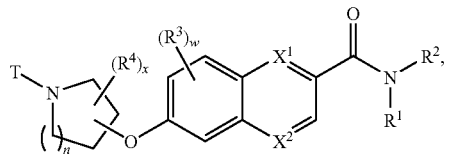
(VIII)

in which k is 0, n is 0, 1, 2 or 3, one of $X^1$ and $X^2$ is N and the other is a carbon, and all other variables are defined as described above with reference to structural formula (I). In one embodiment, for example, $X^1$ is N and $X^2$ is a carbon. In another embodiment, $X^1$ is a carbon, and $X^2$ is N.

In another embodiment of the presently disclosed compounds, the compound has structural formula (IX):

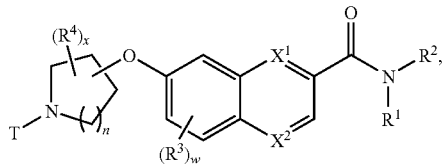
(IX)

in which k is 0, n is 0, 1, 2 or 3, one of $X^1$ and $X^2$ is N and the other is a carbon, and all other variables are defined as described above with reference to structural formula (I). In one embodiment, for example, $X^1$ is N and $X^2$ is a carbon. In another embodiment, $X^1$ is a carbon, and $X^2$ is N.

In one embodiment of the presently disclosed compounds, the compound has structural formula (X):

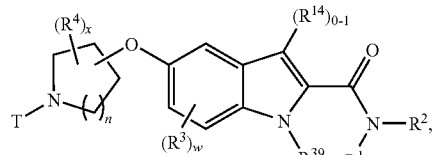
(X)

in which n is 0, 1, 2 or 3 and all other variables are defined as described above with reference to structural formula (I). In certain embodiments, one $R^{14}$ is substituted on the pyrrolo carbon. In other embodiments, no $R^{14}$ is substituted on the pyrrolo carbon.

In another embodiment of the presently disclosed compounds, the compound has structural formula (XI):

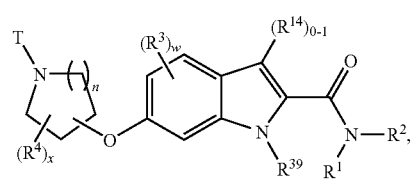
(XI)

in which the variables are defined as described above with reference to structural formula (I). In certain embodiments, one $R^{14}$ is substituted on the pyrrolo carbon. In other embodiments, no $R^{14}$ is substituted on the pyrrolo carbon.

In certain embodiments of the compounds disclosed with reference to structural formulae (VI)-(XI), n is 1 or 2. For example, in one embodiment, n is 2. In another embodiment, n is 1.

In one embodiment of the presently disclosed compounds, the compound has the structural formula (XII):

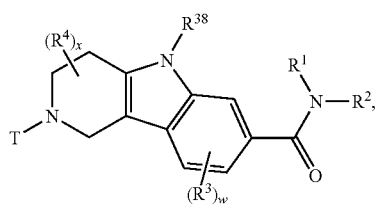
(XII)

in which the variables are defined as described above with reference to structural formulae (I) and (II).

In another embodiment of the presently disclosed compounds, the compound has structural formula (XIII):

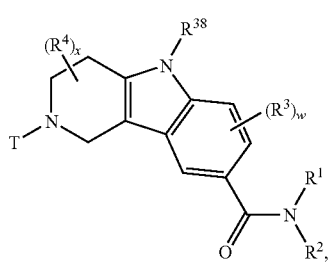
(XIII)

in which the variables are defined as described above with reference to structural formulae (I) and (III).

In another embodiment of the presently disclosed compounds, the compound has structural formula (XIV):

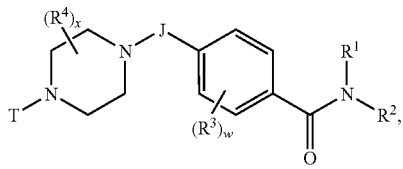
(XIV)

in which J is —CH$_2$—, —CH(R$^{26}$)— or —C(R$^{26}$)$_2$— (e.g., —CH$_2$—), and all other variables are defined as described above with reference to structural formulae (I) and (IV).

In another embodiment of the presently disclosed compounds, the compound has structural formula (XV):

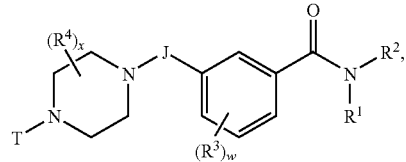
(XV)

in which J is —CH$_2$—, —CH(R$^{26}$)— or —C(R$^{26}$)$_2$— (e.g., —CH$_2$—), and all other variables are defined as described above with reference to structural formulae (I) and (V).

In another embodiment of the presently disclosed compounds, the compound has structural formula (XVI):

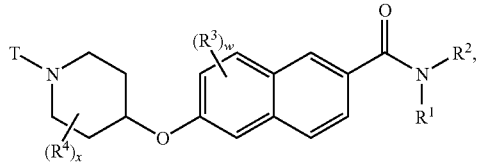
(XVI)

in which the variables are defined as described above with reference to structural formulae (I) and (VI).

In another embodiment of the presently disclosed compounds, the compound has structural formula (XVII):

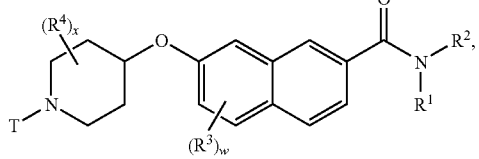
(XVII)

in which the variables are defined as described above with reference to structural formulae (I) and (VII).

In one embodiment of the presently disclosed compounds, the compound has structural formula (XVIII):

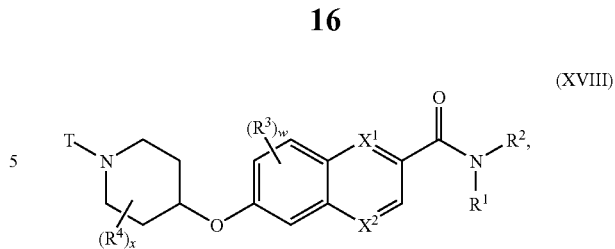
(XVIII)

in which one of X$^1$ and X$^2$ is N, and the other is a carbon; and the other variables are defined as described above with reference to structural formulae (I) and (VIII). In one embodiment, for example, X$^1$ is N and X$^2$ is a carbon. In another embodiment, X$^1$ is a carbon, and X$^2$ is N.

In another embodiment of the presently disclosed compounds, the compound has structural formula (XIX):

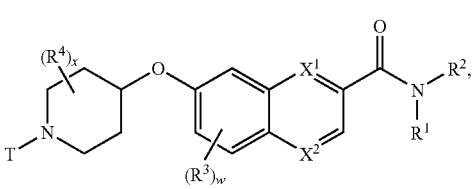
(XIX)

in which one of X$^1$ and X$^2$ is N, and the other is a carbon; and the other variables are defined as described above with reference to structural formulae (I) and (IX). In one embodiment, for example, X$^1$ is N and X$^2$ is a carbon. In another embodiment, X$^1$ is a carbon, and X$^2$ is N.

In one embodiment of the presently disclosed compounds, the compound has structural formula (XX):

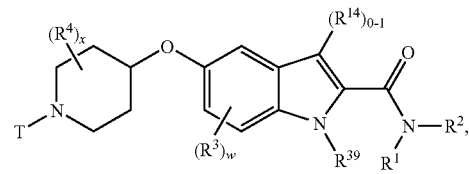
(XX)

in which the variables are defined as described above with reference to structural formulae (I) and (X). In certain embodiments, one R$^{14}$ is substituted on the pyrrolo carbon. In other embodiments, no R$^{14}$ is substituted on the pyrrolo carbon.

In another embodiment of the presently disclosed compounds, the compound has structural formula (XXI):

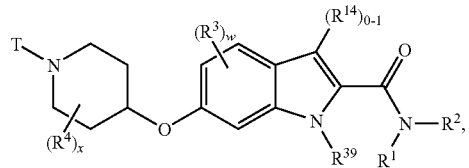
(XXI)

in which the variables are defined as described above with reference to structural formulae (I) and (XI). In certain embodiments, one R$^{14}$ is substituted on the pyrrolo carbon. In other embodiments, no R$^{14}$ is substituted on the pyrrolo carbon.

In certain embodiments of the presently disclosed compounds of any of structural formulae (I)-(XXI), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (I)-(XXI), $R^2$ is -Hca. In certain embodiments, $R^2$ is an optionally-substituted monocyclic heterocycloalkyl. In another embodiment, $R^2$ is not an oxo-substituted heterocycloalkyl. In certain embodiments (e.g., when the compound has structural formula (II) or (III)), $R^2$ is not tetrahydro-2H-pyran-4-yl moiety or a tetrahydrothiophene S,S-dioxide moiety.

In certain of the presently disclosed compounds of any structural formulae (I)-(XXI), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (I)-(XXI), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (I)-(XXI), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (I)-(XXI), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (I)-(XXI), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—$NR^9$—, such as —C(O)—NH—.

In other embodiments of the presently disclosed compounds of any of structural formulae (I)-(XXI), the azetidinyl, pyrrolidinyl, piperidinyl or azepanyl $R^2$ moiety is substituted at its 1-position with —C(O)—O($C_0$-$C_6$ alkyl), —C(O)-Het, —C(O)-Ar, —S(O)$_2$-Het, —S(O)$_2$-Ar or —S(O)$_2$—O($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl or azepanyl $R^2$ moiety is substituted at its 1-position with —C(O)-Het or —C(O)-Ar; in another embodiment, it is substituted at its 1-position with —S(O)$_2$-Het or —S(O)$_2$-Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments of the compounds of any of structural formulae (I)-(XXI), $R^2$ is -Cak-N($R^9$)-G-$R^{22}$, as described above. For example, in one embodiment of the disclosed compounds, $R^2$ has the structure

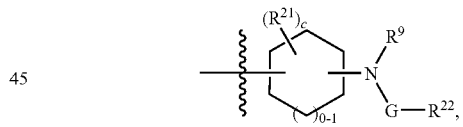

in which c is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—

($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, $R^9$ is H. In certain embodiments, G is a single bond. In certain embodiments of the presently disclosed compounds, each $R^{22}$ is not substituted with an aryl-, heteroaryl-, cycloalkyl- or heterocycloalkyl-containing group. In certain embodiments of the presently disclosed compounds, each $R^{23}$ is not substituted with an aryl-, heteroaryl-, cycloalkyl- or heterocycloalkyl-containing group.

In one embodiment of compounds of any of structural formulae (I)-(XXI), $R^2$ has the structure

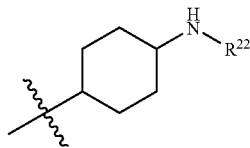

In certain embodiments of the compounds of any of structural formulae (I)-(XXI), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -G$R^{23}$ or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —$CH_2$—$CH_2$—$CH_2$—N($R^9$)—$R^{24}$ or —$CH_2$—$CH_2$—$CH_2$—$CH_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —$CH_2$—$CH_2$—O—$CH_2$—$CH_2$—N($R^9$)—$R^{24}$; —$CH_2$—CH($CH_3$)—N($R^9$)—$R^{24}$; or —$CH_2$—$CH_2$—O—$CH_2$—C(O)—N($R^9$)—$R^{24}$. In certain embodiments, $R^9$ is H. In certain embodiments, $R^{24}$ is Ar or Het. In certain embodiments, $R^{24}$ is not substituted with an aryl-, heteroaryl-, cycloalkyl- or heterocycloalkyl-containing group. In certain embodiments, the ($C_2$-$C_8$ alkyl) is a ($C_2$-$C_5$ alkyl).

In the compounds of any of structural formulae (I)-(XXI), the number of substituents on benzo, pyrido or pyrazino carbons of the ring system represented by "B", w, is 0, 1, 2 or 3. For example, in one embodiment, w is 0, 1 or 2. In another embodiment, such as when the ring system represented by "B" does not include a benzo, pyrido or pyrazino moeity, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1$-$C_4$ alkyl) (e.g., methyl, ethyl or propyl). In certain embodiments, an $R^3$ is substituted on the "B" ring system at a benzo, pyrido or pyrazino ring position in the meta position relative to the J moiety.

In certain embodiments of the compounds of any of structural formulae (I)-(XXI), each $R^3$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of any of structural formulae (I)-(XXI), w is at least one, and at least one $R^3$ is —$NR^8R^9$. For example, in one embodiment, w is 1. In certain such embodiments, $R^3$ is substituted on the "B" ring system at a benzo, pyrido or pyrazino ring position in the meta position relative to the J moiety.

In other embodiments of the compounds of any of structural formulae (I)-(XXI), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a benzo, pyrido or pyrazino ring position in the meta position relative to the J moiety. In one particular embodiment, $R^3$ is —$CH_2$—N($CH_3$)—$CH_2$—C(O)—$OCH_3$.

In the compounds of structural formula (I), the number of substituents on non-benzo, non-pyrido, non-pyrazino carbons, k, is 0, 1 or 2. For example, in one embodiment, k is 1. In other embodiments, such as when the ring system represented by "B" contains only benzo, pyridino and/or piperazino carbons, k is 0. In certain embodiments of the compounds of structural formula (I), each $R^{14}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{14}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. Each $R^{14}$ can be, for example, halo (e.g., —Cl or —F), cyano unsubstituted —($C_1$-$C_4$ alkyl) (e.g., methyl or ethyl) or unsubstituted —($C_1$-$C_4$ haloakyl) (e.g., difluoromethyl, trifluoromethyl and the like).

In the presently disclosed compounds of any of structural formulae (I)-(XXI), the number of substituents on the azacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (I)-(XXI), two $R^4$ groups combine to form an oxo. The oxo can be bound, for example, at the position alpha to the nitrogen of the azacycloalkyl ring. In other embodiments, no two $R^4$ groups combine to form an oxo.

In certain embodiments of the presently disclosed compounds of any of structural formulae (I)-(XXI), when x is 4, not all four $R^4$ groups are ($C_1$-$C_6$ alkyl).

In certain embodiments of the presently disclosed compounds of any of structural formulae (I)-(XXI), each $R^4$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (XXII):

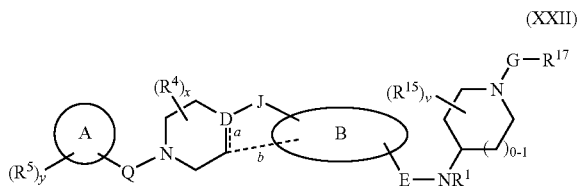

(XXII)

in which Q and G are each independently a bond, —$CH_2$—, —C(H)($R^{16}$)—, —C($R^{16}$)$_2$—, L (e.g., —C(O)—$NR^9$— or —$NR^9$—C(O)—) or —$S(O)_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, and two $R^{15}$ on the same carbon optionally combine to form oxo; $R^{17}$ is Het or Ar, and all other variables are defined as described above with reference to any of structural formula (I)-(XXI). In one embodiment, Q is a single bond. In another embodiment, Q is —$CH_2$—. In other embodiments, Q is —C(O)— or —$S(O)_2$—. In certain embodiments, G is —$CH_2$—. In other embodiments, G is —C(O)— or —$S(O)_2$—. In other embodiments, G is —CH($CH_3$)—. In other embodiments, G is —C(O)—NH—. The above-recited Q and G moieties can be combined in any possible combination. For example, in one embodiment, Q is a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formula (XXII), v is 0, 1, 2, 3 or 4. In one embodiment, v is 0, 1, 2 or 3. For example, v can be 0, or can be 1 or 2.

In certain embodiments of the presently disclosed compounds of structural formula (XXII), two $R^{15}$ groups combine to form an oxo. The oxo can be bound, for example, at the position alpha relative to the nitrogen of the azacycloalkyl ring. In other embodiments, no two $R^{15}$ groups combine to form an oxo.

In certain embodiments of the presently disclosed compounds of structural formula (XXII), when v is 4, not all four $R^{15}$ moieties are ($C_1$-$C_6$ alkyl).

In certain embodiments of the presently disclosed compounds of structural formula (XXII), each $R^{15}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S (O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In some embodiments, one R$^{15}$ is —C(O)NR$^9$R$^7$, which can be bound, for example, at a position alpha relative to the piperidine nitrogen, or at the position linked to the —N(R$^1$)—.

In certain embodiments of the presently disclosed compounds of structural formula (XXII), R$^{17}$ is an unsubstituted aryl or heteroaryl. In other embodiments, the R$^{17}$ Ar or Het is substituted with 1, 2 or 3 substituents independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, the R$^{17}$ Ar or Het is substituted with 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, R$^{17}$ is substituted with 1, 2 or 3 substituents selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca. R$^{17}$ can be substituted with, for example, one such substituent, or two such substituents.

In certain embodiments, the presently disclosed compounds have the structural formula (XXIII):

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —C(O)—(C$_1$-C$_4$ alkyl) or —C(O)—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (I)-(XXII). In one embodiment, R$^{27}$ and R$^{29}$ are both H.

In certain embodiments, the presently disclosed compounds have the structural formula (XXIV):

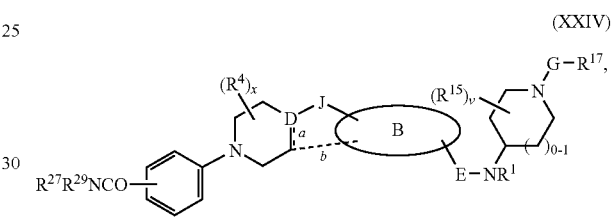

(XXIV)

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (I)-(XXII). In one embodiment, R$^{27}$ and R$^{29}$ are both H.

In certain embodiments, the presently disclosed compounds have the structural formula (XXV):

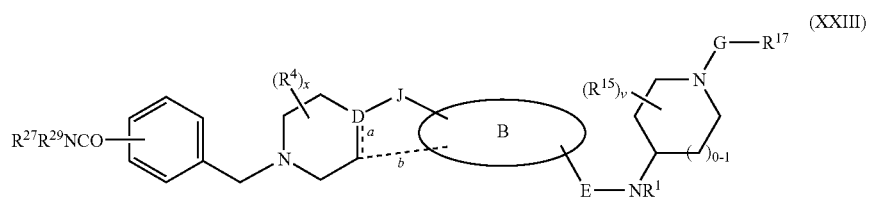

(XXIII)

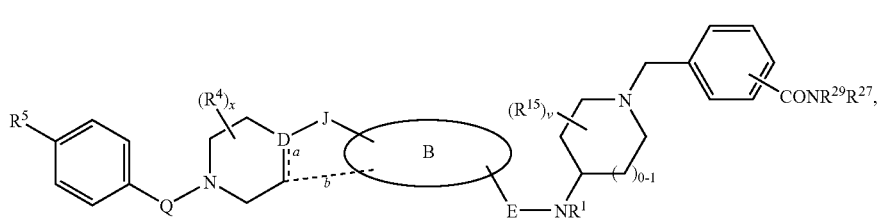

(XXV)

in which R[27] is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-NR[9]($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and R[29] is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or R[27] and R[29] together with the nitrogen to which they are bound form Hca, and all other variables are as described above with reference to any of structural formulae (I)-(XXII). In one embodiment, R[27] and R[29] are both H.

In certain embodiments, the presently disclosed compounds have the structural formula (XXVI):

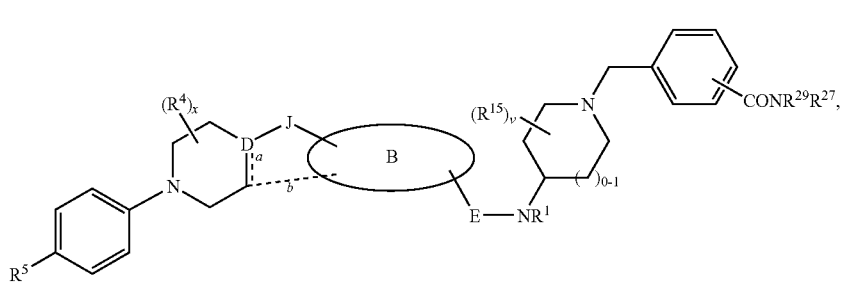

(XXVI)

in which R[27] is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-NR[9]($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and R[29] is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or R[27] and R[29] together with the nitrogen to which they are bound form Hca, and all other variables are as described above with reference to any of structural formulae (I)-(XXII). In one embodiment, R[27] and R[29] are both H.

In certain embodiments, the presently disclosed compounds have the structural formula (XXVII):

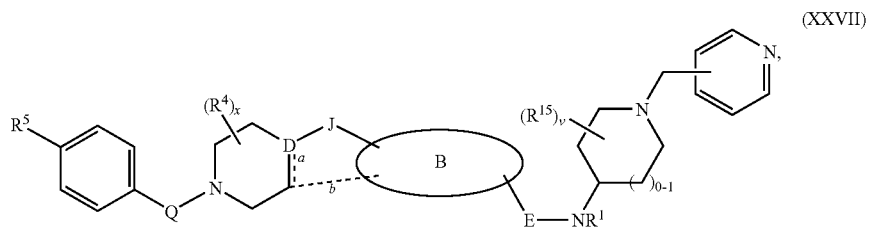

(XXVII)

in which all variables are as described above with reference to any of structural formulae (I)-(XXII).

In certain embodiments, the presently disclosed compounds have the structural formula (XXVIII):

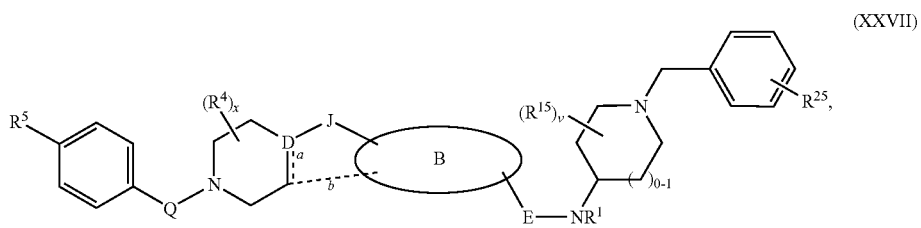
(XXVII)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (I)-(XXII). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (XXIX):

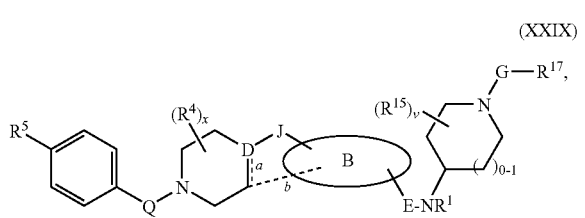
(XXIX)

in which G is —C(O)—, —S(O)$_2$— or —C(O)—NH— and all other variables are as described above with reference to any of structural formulae (I)-(XXII).

In certain embodiments, the presently disclosed compounds have the structural formula (XXX):

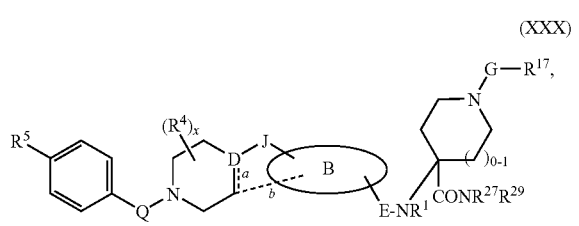
(XXX)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XXII).

In one embodiment, $R^{27}$ and $R^{29}$ are both H. In some embodiments, the compounds of structural formula (XXX) are present as racemic mixtures or scalemic mixtures. In other embodiments, the compounds of structural formula (XXX) are present in an enantiomerically-enriched form, for example as a substantially pure stereoisomer. In certain embodiments, the presently disclosed compounds have the structural formula (XXXI):

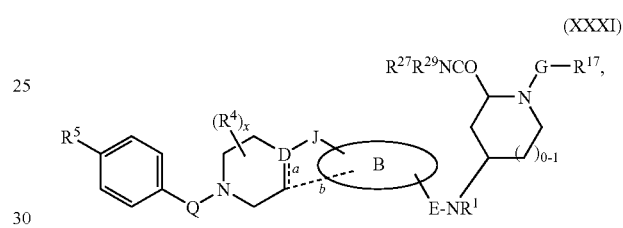
(XXXI)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XXII). In one embodiment, $R^{27}$ and $R^{29}$ are both H. In some embodiments, the compounds of structural formula (XXXI) are present as racemic mixtures or scalemic mixtures. In other embodiments, the compounds of structural formula (XXXI) are present in an enantiomerically-enriched form, for example as a substantially pure stereoisomer.

In certain embodiments, the presently disclosed compounds have the structural formula (XXXII):

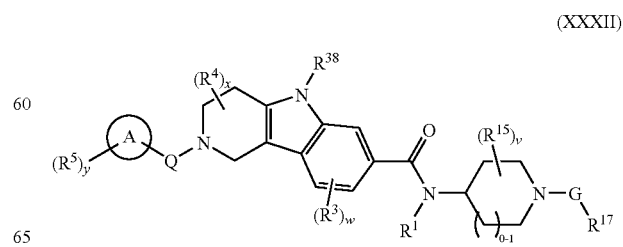
(XXXII)

in which G, v, $R^{15}$ and $R^{17}$ are defined as described above with reference to structural formula (XXII), and all other variables are defined as described above with reference to structural formulae (I) or (II). $R^5$, y, v, $R^{15}$, $R^{17}$, Q, G and the ring denoted by "A" can be defined, for example, as described with reference to any of structural formulae (XXIII)-(XXXI).

In certain embodiments, the presently disclosed compounds have the structural formula (XXXIII):

(XXXIII)

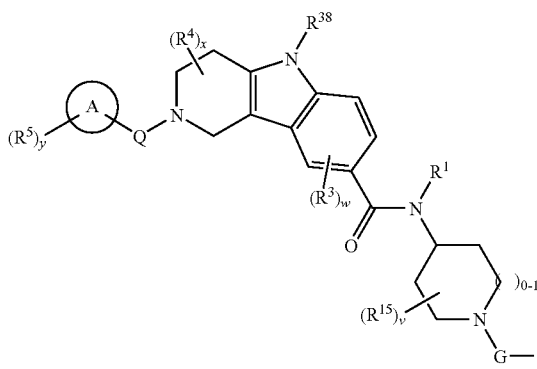

in which G, v, $R^{15}$ and $R^{17}$ are defined as described above with reference to structural formula (XXII), and all other variables are defined as described above with reference to structural formulae (I) or (III). $R^5$, y, v, $R^{15}$, $R^{17}$, Q, G and the ring denoted by "A" can be defined, for example, as described with reference to any of structural formulae (XXIII)-(XXXI).

In certain embodiments, the presently disclosed compounds have the structural formula (XXXIV):

(XXXIV)

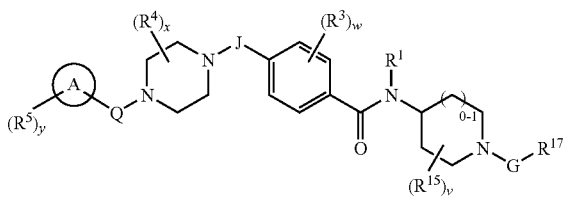

in which J is —$CH_2$—, —$CH(R^{26})$— or —$C(R^{26})_2$— (e.g., —$CH_2$—), G, v, $R^{15}$ and $R^{17}$ are defined as described above with reference to structural formula (XXII), and all other variables are defined as described above with reference to structural formulae (I) or (IV). $R^5$, y, v, $R^{15}$, $R^{17}$, Q, G and the ring denoted by "A" can be defined, for example, as described with reference to any of structural formulae (XXIII)-(XXXI).

In certain embodiments, the presently disclosed compounds have the structural formula (XXXV):

(XXXV)

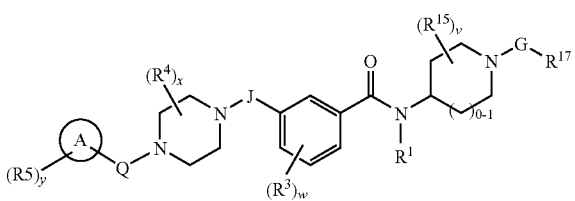

in which J is —$CH_2$—, —$CH(R^{26})$— or —$C(R^{26})_2$— (e.g., —$CH_2$—), G, v, $R^{15}$ and $R^{17}$ are defined as described above with reference to structural formula (XXII), and all other variables are defined as described above with reference to structural formulae (I) or (V). $R^5$, y, v, $R^{15}$, $R^{17}$, Q, G and the ring denoted by "A" can be defined, for example, as described with reference to any of structural formulae (XXIII)-(XXXI).

In certain embodiments, the presently disclosed compounds have the structural formula (XXXVI):

(XXXVI)

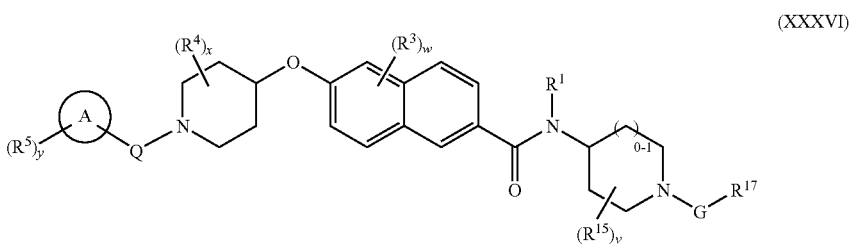

in which G, v, R¹⁵ and R¹⁷ are defined as described above with reference to structural formula (XXII), and all other variables are defined as described above with reference to structural formulae (I) or (VI). $R^5$, y, v, $R^{15}$, $R^{17}$, Q, G and the ring denoted by "A" can be defined, for example, as described with reference to any of structural formulae (XXIII)-(XXXI).

In certain embodiments, the presently disclosed compounds have the structural formula (XXXVII):

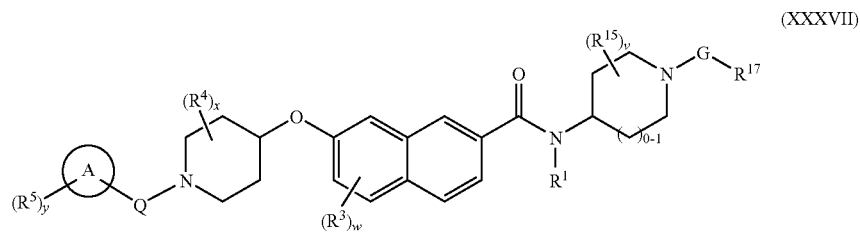

(XXXVII)

in which G, v, $R^{15}$ and $R^{17}$ are defined as described above with reference to structural formula (XXII), and all other variables are defined as described above with reference to structural formulae (I) or (VII). $R^5$, y, v, $R^{15}$, $R^{17}$, Q, G and the ring denoted by "A" can be defined, for example, as described with reference to any of structural formulae (XXIII)-(XXXI).

In certain embodiments, the presently disclosed compounds have the structural formula (XXXVIII):

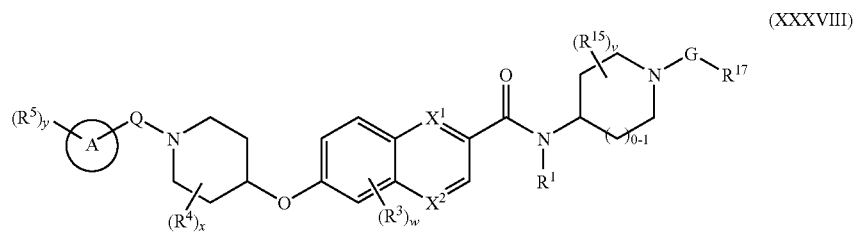

(XXXVIII)

in which one of $X^1$ and $X^2$ is N, and the other is a carbon; G, v, $R^{15}$ and $R^{17}$ are defined as described above with reference to structural formula (XXII), and all other variables are defined as described above with reference to structural formulae (I) or (VIII). $R^5$, y, v, $R^{15}$, $R^{17}$, Q, G and the ring denoted by "A" can be defined, for example, as described with reference to any of structural formulae (XXIII)-(XXXI). In one embodiment, for example, $X^1$ is N and $X^2$ is a carbon. In another embodiment, $X^1$ is a carbon, and $X^2$ is N.

In certain embodiments, the presently disclosed compounds have the structural formula (XXXIX):

in which in which one of $X^1$ and $X^2$ is a carbon; G, v, $R^{15}$ and $R^{17}$ are defined as described above with reference to structural formula (XXII), and all other variables are defined as described above with reference to structural formulae (I) or (IX). $R^5$, y, v, $R^{15}$, $R^{17}$, Q, G and the ring denoted by "A" can be defined, for example, as described with reference to any of structural formulae (XXIII)-(XXXI). In one embodiment, for example, $X^1$ is N and $X^2$ is a carbon. In another embodiment, $X^1$ is a carbon, and $X^2$ is N.

In certain embodiments, the presently disclosed compounds have the structural formula (XL):

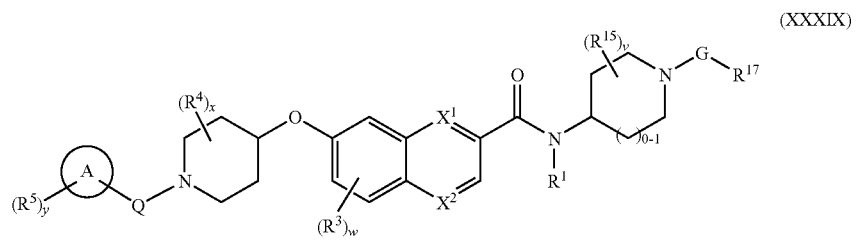

(XXXIX)

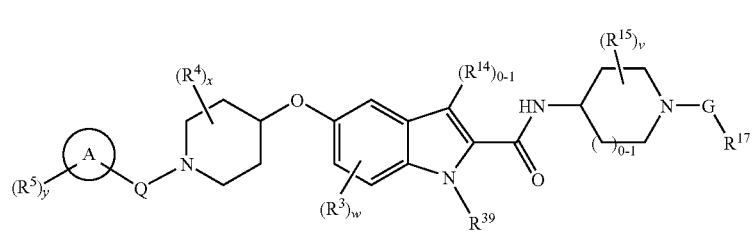

(XL)

in which G, v, $R^{15}$ and $R^{17}$ are defined as described above with reference to structural formula (XXII), and all other variables are defined as described above with reference to structural formulae (I) or (X). $R^5$, y, v, $R^{15}$, $R^{17}$, Q, G and the ring denoted by "A" can be defined, for example, as described with reference to any of structural formulae (XXIII)-(XXXI). In certain embodiments, one $R^{14}$ is substituted on the pyrrolo carbon. $R^{14}$ can be, for example, as described above with reference to structural formula (I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloalkyl) (e.g., difluoromethyl, trifluoromethyl and the like). In other embodiments, no $R^{14}$ is substituted on the pyrrolo carbon.

In certain embodiments, the presently disclosed compounds have the structural formula (XLI):

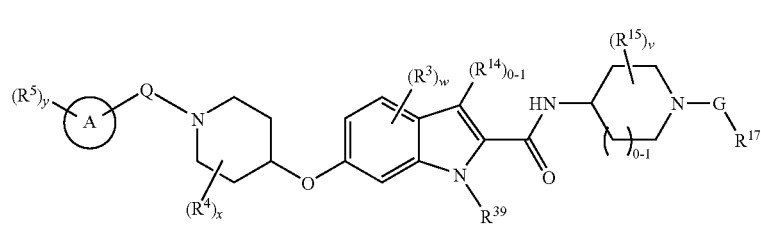

(XLI)

in which G, v, $R^{15}$ and $R^{17}$ are defined as described above with reference to structural formula (XXII), and all other variables are defined as described above with reference to structural formulae (I) or ($X^1$). $R^5$, y, v, $R^{15}$, $R^{17}$, Q, G and the ring denoted by "A" can be defined, for example, as described with reference to any of structural formulae (XXIII)-(XXXI). In certain embodiments, one $R^{14}$ is substituted on the pyrrolo carbon. $R^{14}$ can be, for example, as described above with reference to structural formula (I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloalkyl) (e.g., difluoromethyl, trifluoromethyl and the like). In other embodiments, no $R^{14}$ is substituted on the pyrrolo carbon.

In certain embodiments of compounds having structural formulae (XXII)-(XLI), the moiety has the structure

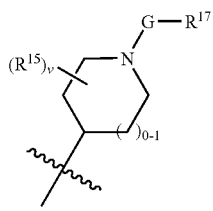

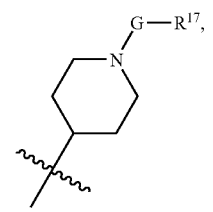

in which G is —$CH_2$—, —CH($CH_3$)—, —C(O)—, —S(O)$_2$— or —C(O)—NH—. For example, in one embodiment, G is —$CH_2$—. In another embodiment, G is —C(O)— or —S(O)$_2$—. In another embodiment, G is —C(O)—NH—.

In other embodiments of compounds having structural formulae (XXII)-(XLI), the

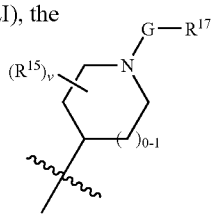

moiety has the structure

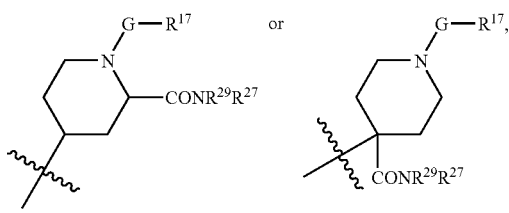

in which G is —CH$_2$—, —C(O)—, —S(O)$_2$— or —C(O)—NH—, R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (XXII)-(XLI), the

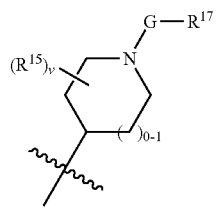

moiety has the structure

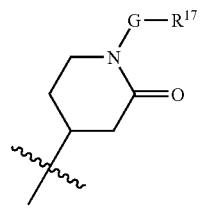

in which G is —CH$_2$—, —C(O)—, —S(O)$_2$— or —C(O)—NH—.

In certain embodiments of compounds having structural formulae (XXII)-(XLI), the R$^{17}$ moiety has the structure

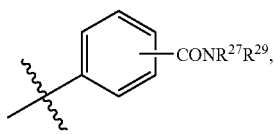

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

In certain embodiments of compounds having structural formulae (XXII)-(XLI), w is 1, and R$^3$ is —NR$^8$R$^9$. In certain such embodiments, R$^3$ is substituted at a benzo, pyrido or pyrazino ring position in the meta position relative to the J moiety.

In other embodiments of compounds having structural formulae (XXII)-(XLI), w is 1, and R$^3$ is —(C$_0$-C$_3$ alkyl)-Y$^1$—(C$_1$-C$_3$ alkyl)-Y$^2$—(C$_0$-C$_3$ alkyl), in which each of Y$^1$ and Y$^2$ is independently L, —O—, —S— or —NR$^9$—. In certain such embodiments, R$^3$ is substituted at a benzo, pyrido or pyrazino ring position in the meta position relative to the J moiety.

In certain embodiments described above, each R$^{27}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group, and each R$^{29}$ is H, methyl or ethyl, or R$^{27}$ and R$^{29}$ together with the nitrogen to which they are bound form Hca.

In certain embodiments of compounds having structural formulae (XXII)-(XLI), at least one R$^5$ moiety is a haloalkyl group, and in exemplary embodiments of these formulae the

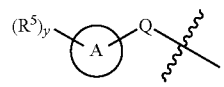

moiety is p-(trifluoromethyl)phenyl. By way of further illustration, certain exemplary compounds including such

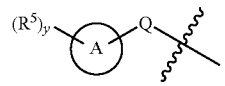

moieties have structural formula (XLII) or (XLIII):

(XLII)

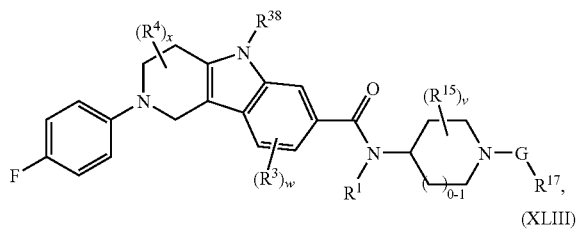

(XLIII)

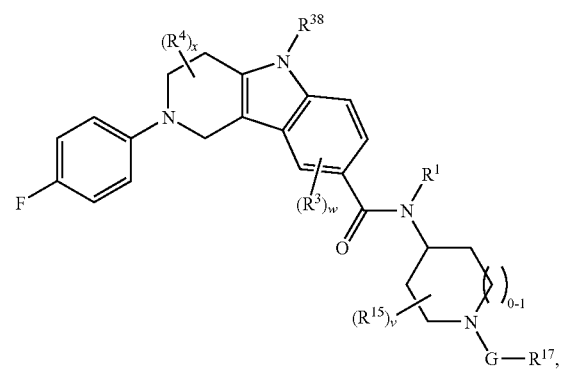

in which all variables are as described above with reference to structural formulae (XXXII) or (XXXIII).

In one embodiment, the presently disclosed compounds have the structural formula (XLIV):

(XLIV)

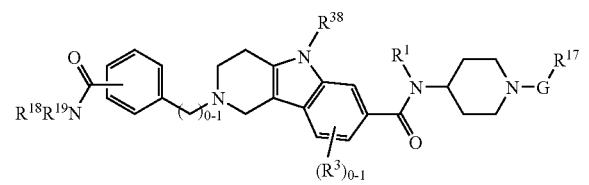

in which G, $R^1$, $R^3$, $R^{17}$ and $R^{38}$ are as described above with reference to any of structural formulae (I), (II), (XII) or (XXII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In one embodiment, the presently disclosed compounds have the structural formula (XLV):

(XLV)

in which G, $R^1$, $R^3$, $R^{17}$ and $R^{38}$ are as described above with reference to any of structural formulae (I), (III), (XIII) and (XXII), and $R^{18}$ and $R^{19}$ are defined as described above with reference to structural formula (XLIV).

In another embodiment, the presently disclosed compounds have the structural formula (XLVI):

(XLVI)

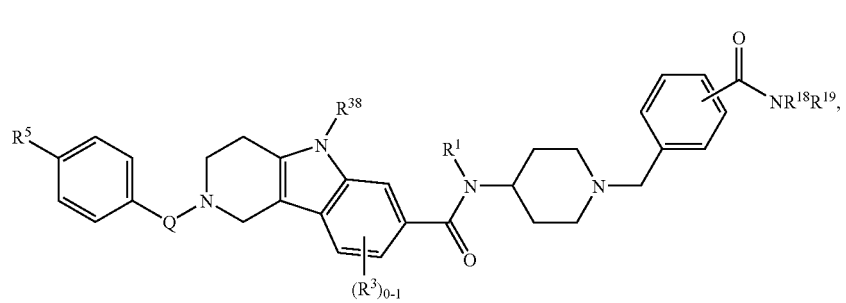

in which Q, $R^1$, $R^3$, $R^5$ and $R^{38}$ are defined as described above with reference to any of structural formulae (I), (II), (XII) and (XXII), and $R^{18}$ and $R^{19}$ are defined as described above with reference to structural formula (XLIV).

In another embodiment, the presently disclosed compounds have the structural formula (XLVII):

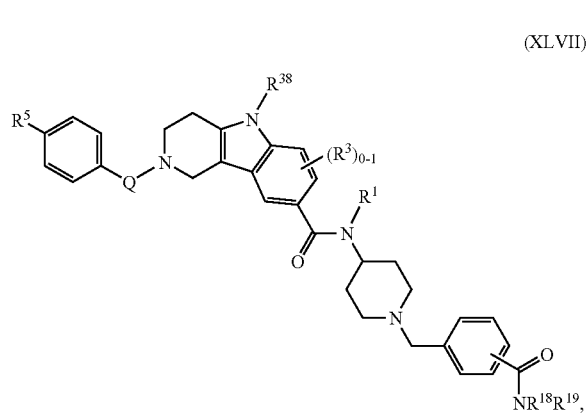

(XLVII)

in which Q, $R^1$, $R^3$, $R^5$ and $R^{38}$ are defined as described above with reference to any of structural formulae (I), (III), (XIII) and (XXII), and $R^{18}$ and $R^{19}$ are defined as described above with reference to structural formula (XLIV).

In another embodiment, the presently disclosed compounds have the structural formula (XLVIII):

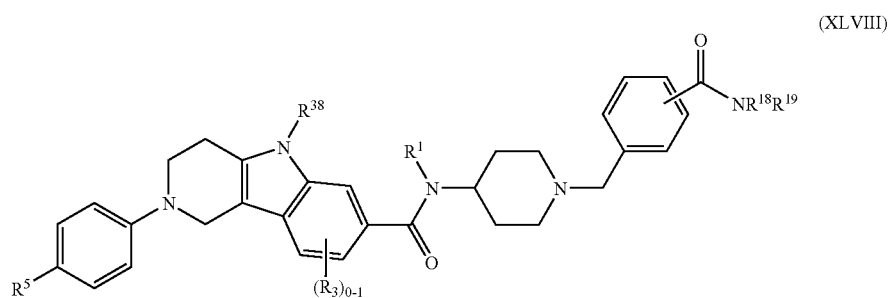

(XLVIII)

in which $R^1$, $R^3$, $R^5$ and $R^{38}$ are defined as described above with reference to any of structural formulae (I), (II), (XII) and (XXII), and $R^{18}$ and $R^{19}$ are defined as described above with reference to structural formula (XLIV).

In another embodiment, the presently disclosed compounds have the structural formula (XLIX):

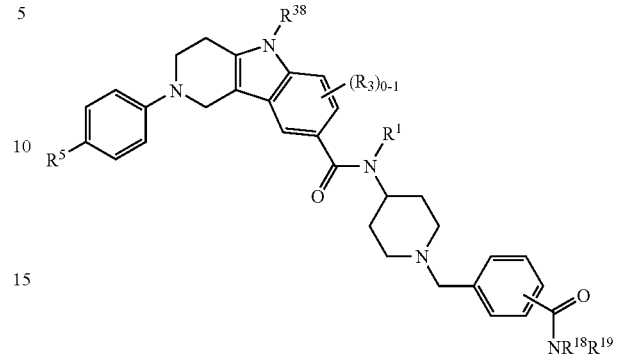

(XLIX)

in which $R^1$, $R^3$, $R^5$ and $R^{38}$ are defined as described above with reference to any of structural formulae (I), (III), (XIII) and (XXII), and $R^{18}$ and $R^{19}$ are defined as described above with reference to structural formula (XLIV).

In compounds according to any of structural formulae (I), (IV)-(XI) and (XIV)-(XXI), T and $R^2$ can be defined as described above with reference to structural formulae (XLIV)-(XLIX).

In certain embodiments, the presently disclosed compounds have the structural formula (L):

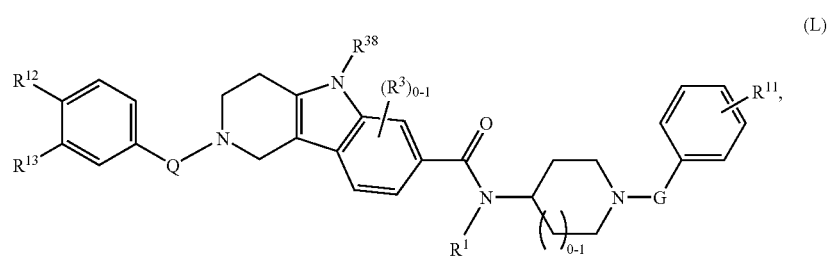

(L)

in which Q is —$CH_2$—, —C(O)— or a single bond; G is a single bond, —$CH_2$—, —C(O)—, —$S(O)_2$— or —C(O)—NH—; $R^1$, $R^3$ and $R^{38}$ are as described above with reference to any of structural formulae (I), (II), (XII) and (XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the benzo moiety. In another embodiment, one $R^3$ (e.g., —Cl, —F, —CH₃, —C₂H₅, —C₃H₇) is substituted on the benzo moiety.

In certain embodiments, the presently disclosed compounds have the structural formula (LI):

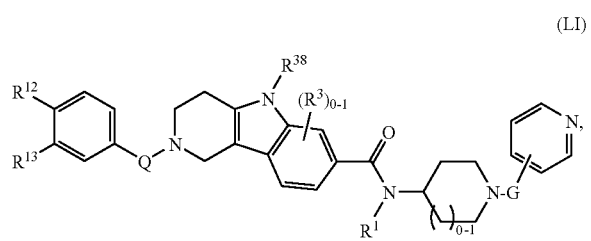

(LI)

in which Q is —CH₂—, —C(O)— or a single bond; G is a single bond, —CH₂—, —C(O)—, —S(O)₂— or —C(O)—NH—; $R^1$, $R^3$ and $R^{38}$ are as described above with reference to any of structural formulae (I), (II), (XII) and (XXII); and $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the benzo moiety. In another embodiment, one $R^3$ (e.g., —Cl, —F, —CH₃, —C₂H₅, —C₃H₇) is substituted on the benzo moiety.

In certain embodiments, the presently disclosed compounds have the structural formula (LII):

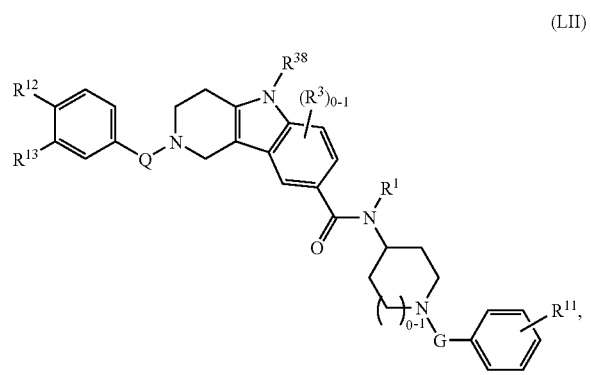

(LII)

in which Q is —CH₂—, —C(O)— or a single bond; G is a single bond, —CH₂—, —C(O)—, —S(O)₂— or —C(O)—NH—; $R^1$, $R^3$ and $R^{38}$ are as described above with reference to any of structural formulae (I), (III), (XIII) and (XXII); and $R^{11}$, $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the benzo moiety. In another embodiment, one $R^3$ (e.g., —Cl, —F, —CH₃, —C₂H₅, —C₃H₇) is substituted on the benzo moiety.

In certain embodiments, the presently disclosed compounds have the structural formula (LIII):

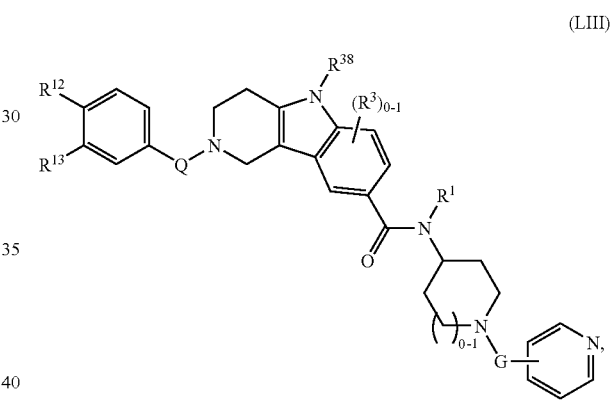

(LIII)

in which Q is —CH₂—, —C(O)— or a single bond; G is a single bond, —CH₂—, —C(O)—, —S(O)₂— or —C(O)—NH—; $R^1$, $R^3$ and $R^{38}$ are as described above with reference to any of structural formulae (I), (III), (XIII) and (XXII); $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the benzo moiety. In another embodiment, one $R^3$ (e.g., —Cl, —F, —CH₃, —C₂H₅, —C₃H₇) is substituted on the benzo moiety.

In one embodiment, the presently disclosed compounds have the structural formula (LIV):

(LIV)

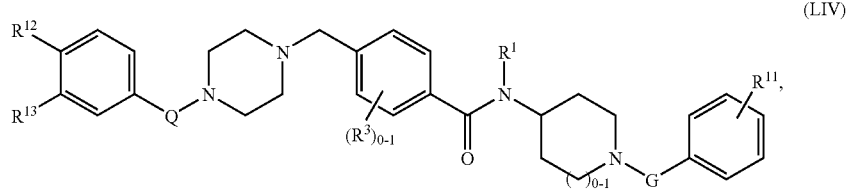

in which Q is —CH$_2$—, —C(O)— or a single bond; G is a single bond, —CH$_2$—, —C(O)—, —S(O)$_2$— or —C(O)—NH—; R$^1$ and R$^3$ are as described above with respect to any of structural formulae (I), (IV), (XIV) and (XXII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the central phenyl moiety. In another embodiment, one R$^3$ (e.g., —Cl, —F, —CH$_3$, —C$_2$H$_5$, —C$_3$H$_7$) is substituted on the central phenyl moiety.

In certain embodiments, the presently disclosed compounds have the structural formula (LV):

and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the central phenyl moiety. In another embodiment, one R$^3$ (e.g., —Cl, —F, —CH$_3$, —C$_2$H$_5$, —C$_3$H$_7$) is substituted on the central phenyl moiety.

(LV)

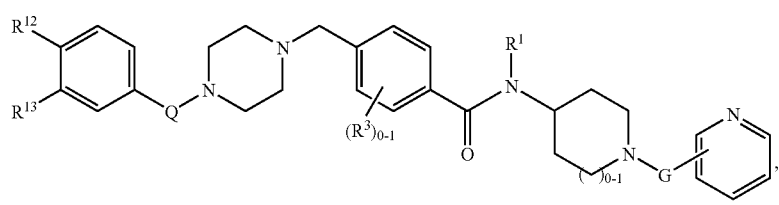

In certain embodiments, the presently disclosed compounds have the structural formula (LVI):

(LVI)

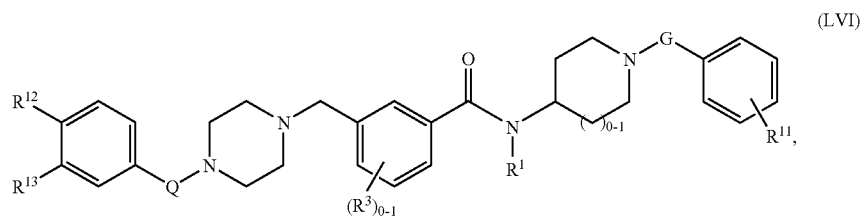

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I), (IV), (XIV) and (XXII); and R$^{12}$ in which Q is —CH$_2$—, —C(O)— or a single bond; G is a single bond, —CH$_2$—, —C(O)—, —S(O)$_2$— or —C(O)—NH—; R$^1$ and R$^3$ are as described above with respect to any of structural formulae (I), (V), (XV) and (XXII); and R$^{11}$, R$^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (LVII):

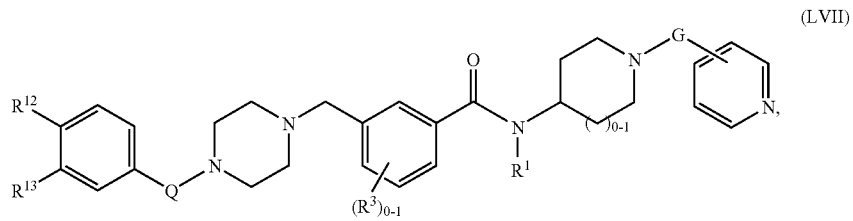

(LVII)

in which Q is —$CH_2$—, —C(O)— or a single bond; G is a single bond, —$CH_2$—, —C(O)—, —$S(O)_2$— or —C(O)NH—; $R^1$ and $R^3$ are as described above with reference to any of structural formulae (I), (V), (XV) and (XXII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (LVIII):

in which Q is —$CH_2$—, —C(O)— or a single bond; G is a single bond, —$CH_2$—, —C(O)—, —$S(O)_2$— or —C(O)NH—; $R^1$ and $R^3$ are as described above with reference to any of structural formulae (I), (VI), (XVI) and (XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the naphthyl moiety. In another embodiment, one $R^3$ (e.g., —Cl, —F, —$CH_3$, —$C_2H_5$, —$C_3H_7$) is substituted on the naphthyl moiety.

In certain embodiments, the presently disclosed compounds have the structural formula (LIX):

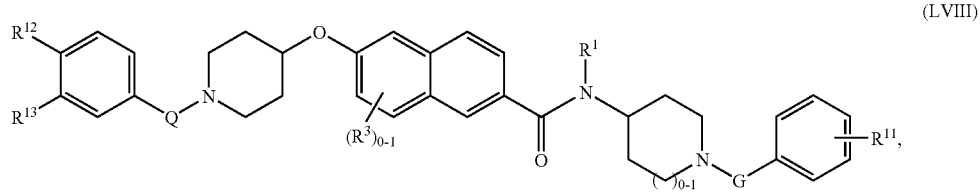

(LVIII)

(LIX)

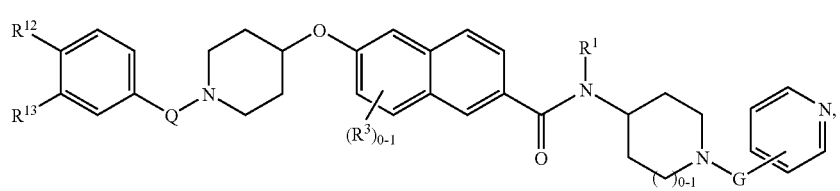

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to structural formulae (I), (VI), (XVI) and (XXII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (LX):

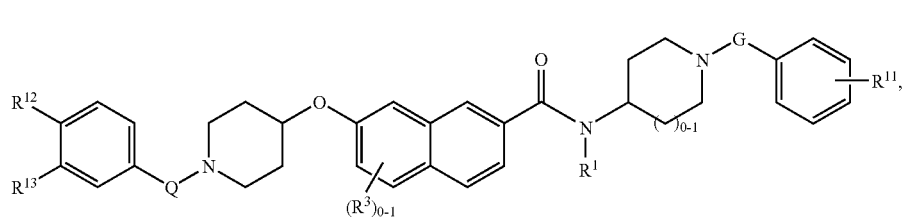

(LX)

—(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (LXI):

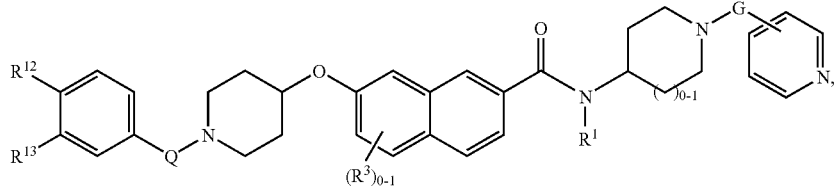

(LXI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I), (VII), (XVII) and (XXII); and R$^{11}$, R$^{12}$ and R$^{13}$ are independently selected from H, halo, cyano, in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to structural formulae (I), (VII), (XVII) and (XXII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the naphthyl moiety. In another embodiment, one $R^3$ (e.g., —Cl, —F, —$CH_3$, —$C_2H_5$, —$C_3H_7$) is substituted on the naphthyl moiety.

In certain embodiments, the presently disclosed compounds have the structural formula (LXII):

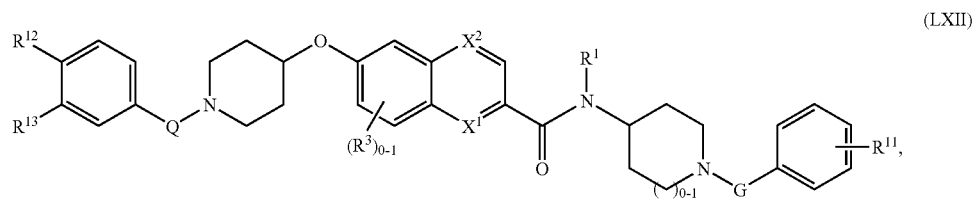

(LXII)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (I), (VIII), (XVIII) and (XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)O—($C_0$-$C_4$ alkyl), —C(O)—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (LXIII):

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to structural formulae (I), (VIII), (XVIII) and (XXII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (LXIV):

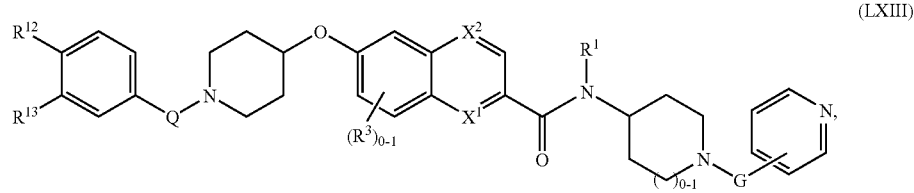

(LXIII)

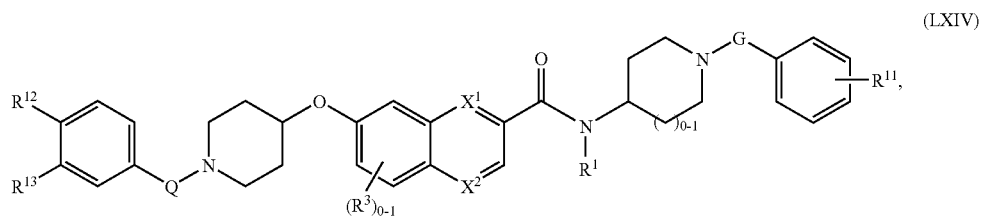

(LXIV)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (I), (IX), (XIX) and (XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (LXV):

dently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

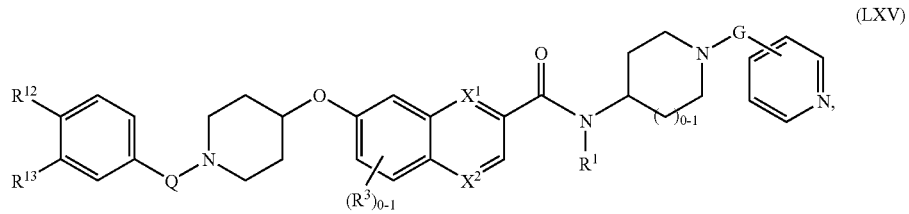

(LXV)

In certain embodiments, the presently disclosed compounds have the structural formula (LXVI):

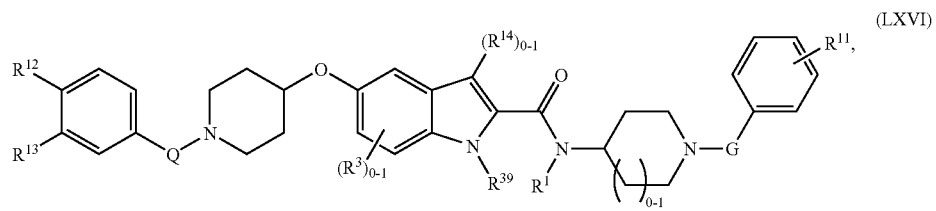

(LXVI)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to structural formulae (I), (IX), (XIX) and (XXII); and $R^{12}$ and $R^{13}$ are indepenin which Q is —$CH_2$—, —C(O)— or a single bond; G is a single bond, —$CH_2$—, —C(O)—, —$S(O)_2$— or —C(O)—NH—; $R^1$, $R^3$ and $R^{39}$ are as described above with reference to any of structural formulae (I), (X), (XX) and (XXII); $R^{14}$ is as described above with reference to structural formulae (I), (X), (XX) and (XXII) (e.g., absent, methyl or halo); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the benzo moiety. In another embodiment, one $R^3$ (e.g., —Cl, —F, —$CH_3$, —$C_2H_5$, —$C_3H_7$) is substituted on the benzo moiety.

In certain embodiments, the presently disclosed compounds have the structural formula (LXVII):

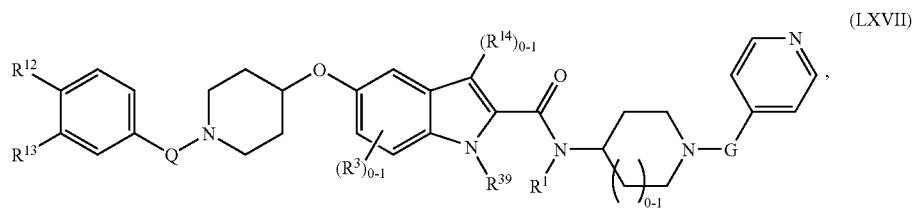

(LXVII)

in which Q is —$CH_2$—, —C(O)— or a single bond; G is a single bond, —$CH_2$—, —C(O)—, —S(O)$_2$— or —C(O)—NH—; $R^1$, $R^3$ and $R^{39}$ are as described above with reference to any of structural formulae (I), (X), (XX) and (XXII); $R^{14}$ is as described above with reference to structural formulae (I), (X), (XX) and (XXII) (e.g., absent, methyl or halo); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the benzo moiety. In another embodiment, one $R^3$ (e.g., —Cl, —F, —$CH_3$, —$C_2H_5$, —$C_3H_7$) is substituted on the benzo moiety.

In certain embodiments, the presently disclosed compounds have the structural formula (LXVIII):

in which Q is —$CH_2$—, —C(O)— or a single bond; G is a single bond, —$CH_2$—, —C(O)—, —S(O)$_2$— or —C(O)—NH—; $R^1$, $R^3$ and $R^{39}$ are as described above with reference to any of structural formulae (I), (XI), (XXI) and (XXII); $R^{14}$ is as described above with reference to structural formulae (I), (XI), (XXI) and (XXII) (e.g., absent, methyl or halo); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the benzo moiety. In another embodiment, one $R^3$ (e.g., —Cl, —F, —$CH_3$, —$C_2H_5$, —$C_3H_7$) is substituted on the benzo moiety.

In certain embodiments, the presently disclosed compounds have the structural formula (LXIX):

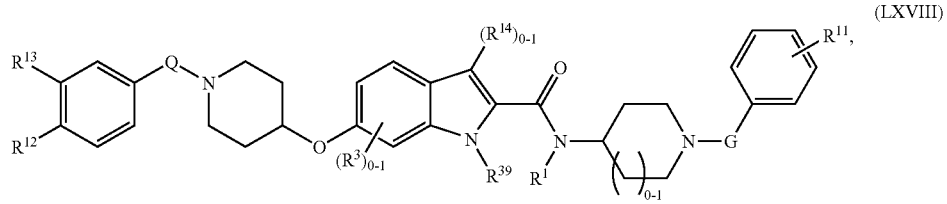

(LXVIII)

(LXIX)

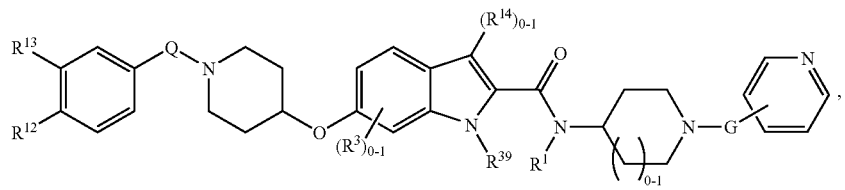

in which Q is —CH$_2$—, —C(O)— or a single bond; G is a single bond, —CH$_2$—, —C(O)—, —S(O)$_2$— or —C(O)—NH—; R$^1$, R$^3$ and R$^{39}$ are as described above with reference to any of structural formulae (I), (X), (XX) and (XXII); R$^{14}$ is as described above with reference to structural formulae (I), (X), (XX) and (XXII) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In one embodiment of the presently disclosed compounds of any of structural formulae (I)-(XXI), the compound has the structural formula (XXII), in which the "A" ring system is an aryl or heteroaryl; E is —C(O)— or —S(O)$_2$—, and in which the compound has a computed low energy three-dimensional conformer in which the oxygen of the E —C(O)— group is positioned at (0 Å, 0 Å, 0 Å), or one of the oxygens of the E —S(O)$_2$— group is positioned at (0 Å, 0 Å, 0 Å);

the centerpoint of an aromatic ring of the aryl or heteroaryl of the "B" ring system is positioned within 3.5 Å of (−3.1 Å, 0.4 Å, 1.2 Å);

the nitrogen of the right-hand azacycloalkyl (i.e., the ring to which -G-R$^{17}$ is bound) is positioned within 3.5 Å of (0.8 Å, 1.6 Å, −5.3 Å);

the centerpoint of the left-hand azacycloalkyl (i.e., the ring to which -Q-(A ring)-(R$^5$)$_y$ is bound) is positioned within 3.5 Å of (−6.2 Å, 0.1 Å, 7.4 Å); and the centerpoint of an aromatic ring of the aryl or heteroaryl of the "A" ring system is positioned within 3.5 Å of (−7.4 Å, −1.9 Å, 10.7 Å).

In certain embodiments of the presently disclosed compounds of structural formula (XXII), in a computed low energy three-dimensional conformer:

the oxygen of the E —C(O)— group is positioned at (0 Å, 0 Å, 0 Å), or one of the oxygens of the E —S(O)$_2$— group is positioned at (0 Å, 0 Å, 0 Å);

the centerpoint of an aromatic ring of the aryl or heteroaryl of the "B" ring system is positioned within 2.5 Å of (−3.1 Å, 0.4 Å, 1.2 Å);

the nitrogen of the right-hand azacycloalkyl is positioned within 1.8 Å of (0.8 Å, 1.6 Å, −5.3 Å);

the centerpoint of the left-hand azacycloalkyl is positioned within 2.5 Å of (−6.2 Å, 0.1 Å, 7.4 Å); and the centerpoint of an aromatic ring of the aryl or heteroaryl of the "A" ring system is positioned within 2.5 Å of (−7.4 Å, −1.9 Å, 10.7 Å).

In one embodiment of the presently disclosed compounds of structural formula (XXII), the "A" ring system is an aryl or heteroaryl substituted with a hydrophobic moiety; R$^{17}$ is substituted with an electron acceptor; E is —C(O)— or —S(O)$_2$—, and the compound has a computed low energy three-dimensional conformer in which the oxygen of the E —C(O)— group is positioned at (0 Å, 0 Å, 0 Å), or one of the oxygens of the E —S(O)$_2$— group is positioned at (0 Å, 0 Å, 0 Å);

the centerpoint of an aromatic ring of the aryl or heteroaryl of the "B" ring system is positioned within 3.5 Å of (−3.1 Å, 0.4 Å, 1.2 Å);

the nitrogen of the right-hand azacycloalkyl is positioned within 3.5 Å of (0.8 Å, 1.6 Å, −5.3 Å);

the centerpoint of the left-hand azacycloalkyl is positioned within 3.5 Å of (−6.2 Å, 0.1 Å, 7.4 Å); and the centerpoint of an aromatic ring of the aryl or heteroaryl of the "A" ring system is positioned within 3.5 Å of (−7.4 Å, −1.9 Å, 10.7 Å);

the hydrophobic moiety substituted on the "A" ring system is positioned within 3.5 Å of (−9.0 Å, −3.2 Å, 13.4 Å); and the electron acceptor substituted on R$^{17}$ is positioned within 3.5 Å of (7.0 Å, −2.7 Å, −7.0 Å).

The hydrophobic moiety can be, for example, any of the following, as defined in SMARTS query format:
INCLUDE
[a]F group(2)
[a]Cl group(2)
[a]Br group(2)
[a]I group(2)
[a]C(F)(F)(F) group(2,3,4,5)
[a][CH$_2$]C(F)(F)(F) group(2,3,4,5,6)
[a]O[CH$_3$] group(2,3)
[a]S[CH$_3$] group(2,3)
[a]OC(F)(F)(F) group(2,3,4,5,6)
C(F)(F)(F) group
F group
Cl group
Br group
I group
default_aromatic_surface group
default_aliphatic_surface group
C[S;X2]C group
[S;X2]CC group
[S;X2]C group.

The electron acceptor can be, for example, any of the following, as defined in SMARTS query format:
INCLUDE
[N;X1]#[#6] vector(1)

[N;X1]#CC vector(1)
[N;X2](=C~[C,c])C vector(1)
[N;X2](O)=N[a] vector(1)
[N;X2](=N—O)[a] vector(1)
[n;X2]1ccccc1 vector(1)
[n;X2]([a])([a]) vector(1)
[N;X2](=C~[C,c])(~[*]) vector(1)
[N;X3](C)(C)[N;X3]C vector(1)
[N;X2](=C)(~[*]) vector(1)
[N;X2](~[C,c])=[N;X2] vector(1)
[n;X2]1c[nH]cc1 vector(1)
O=[S;X4](=O)([!#8])([!#8]) vector(1)
[O;X2]C vector(1)
[O;X2]N vector(1)
[O;X1]=[C,c] vector(1)
o vector(1)
[O;X2](C)C vector(1)
[O;X2]c1ncccc1 vector(1)
[O;X2~][a] vector(1)
O=PO([!#1]) vector(1)
[O;X2] vector(1)
[S;X2](C)C vector(1)
[S;X2](=C)N vector(1)
EXCLUDE
O=C[O—,OH] point
[O—,OH]C(=O) point
[nH]([a])[a] point
[#7;X3][*]=[O,S] point
[N;X3](C)(C)[C;X3] point
[N;X3][a] point
N(=N=N)[#6] point
[NH2](C(=O)[NH2]) point
[NH](C=O)(C=O) point
[NH2](S(=O)(=O)[#6])[#6] point
[NH](S(=O)(=O)[#6])[#6] point
n1c([NH$_2$])ccnc1([NH2]) point
o1nccc1 point
o1cncc1 point
o1cccc1 point
[O;X2]C=O point
[O;X2] point.

In one embodiment of the presently disclosed compounds of structural formula (XXII), the "A" ring system is an aryl or heteroaryl substituted with a hydrophobic moiety; $R^{17}$ is substituted with an electron acceptor; E is —C(O)— or —S(O)$_2$—, and the compound has a computed low energy three-dimensional conformer in which the oxygen of the E —C(O)— group is positioned at (0 Å, 0 Å, 0 Å), or one of the oxygens of the E —S(O)$_2$— group is positioned at (0 Å, 0 Å, 0 Å);

the centerpoint of an aromatic ring of the aryl or heteroaryl of the "B" ring system is positioned within 2.5 Å of (−3.1 Å, 0.4 Å, 1.2 Å);

the nitrogen of the right-hand azacycloalkyl is positioned within 1.8 Å of (0.8 Å, 1.6 Å, −5.3 Å);

the centerpoint of the left-hand azacycloalkyl is positioned within 2.5 Å of (−6.2 Å, 0.1 Å, 7.4 Å); and the centerpoint of an aromatic ring of the aryl or heteroaryl of the "A" ring system is positioned within 2.5 Å of (−7.4 Å, −1.9 Å, 10.7 Å);

the hydrophobic moiety substituted on the "A" ring system is positioned within 2.5 Å of (−9.0 Å, −3.2 Å, 13.4 Å); and the electron acceptor substituted on $R^{17}$ is positioned within 2 Å of (7.0 Å, −2.7 Å, −7.0 Å).

In certain embodiments of the presently disclosed compounds, the computed low energy three-dimensional conformer has a root mean square deviation from the given points of no greater than 3 Å, and a vector score greater than 0.2.

In certain embodiments of the presently disclosed compounds, the computed low energy three-dimensional conformer has a root mean square deviation from the given points of no greater than 1.5 Å, and a vector score greater than 0.4.

In certain embodiments of the presently disclosed compounds, the computed low energy three-dimensional conformer has a root mean square deviation from the given points of no greater than 1.2 Å, and a vector score greater than 0.5.

A centerpoint of a carbocyclic or heterocyclic ring is the average position of the constituent atoms of the ring (i.e., excluding any substituents) as positioned in the low energy three-dimensional conformer. For example, the centerpoint of the left-hand azacycloalkyl is the average position of its ring carbon and nitrogen atom(s). Similarly, the centerpoint of a phenyl ring is the average position of its six ring carbons. Centerpoints are calculated only on single rings; multi-ring systems have multiple centerpoints, one for each ring. For example, a benzofuran would have two centerpoints, one calculated as the average position of the six carbon rings making up the fused benzene subunit, and the other calculated as the average position of the four carbon atoms and one oxygen atom making up the fused furan subunit.

Low energy three-dimensional conformers can be calculated using the Phase software package version 3.0, available from Schrödinger LLC. Low energy three-dimensional conformers can be generated by a torsion search procedure under OPLS_2005 force field with a distance dependent dielectric constant. As the person of skill in the art will appreciate, the low energy conformer should be translated and rotated so that the oxygen of the E —C(O)— group is positioned at (0 Å, 0 Å, 0 Å), or one of the oxygens of the E —S(O)$_2$— group is positioned at (0 Å, 0 Å, 0 Å), and so that the root mean square deviation of the rest of the listed features with respect to the given points is minimized.

As the person of skill in the art will recognize, the various embodiments described above can be combined to form other embodiments of the invention. For example, in one embodiment, Q is —CH$_2$—, as described above, and G is —CH$_2$—, as described above. In another embodiment, the ring system denoted by "A" is a phenyl, the ring system denoted by "B" is a phenyl, J is —N(R$^{38}$)—, D is a carbon, the dotted line denoted by "a" is a bond and the dotted line denoted by "b" is a single bond, as described above.

Examples of compounds according to structural formula (I) include those listed in Table 1. These compounds can be made according to the general schemes described below, for example using procedures analogous to those described below in the Examples.

TABLE 1

| No. | Name | Structure |
|-----|------|-----------|
| 1 | benzyl 8-(1-(4-cyanobenzyl)piperidin-4-ylcarbamoyl)-3,4-dihydro-1H-pyrido[4,3-b]indole-2(5H)-carboxylate | 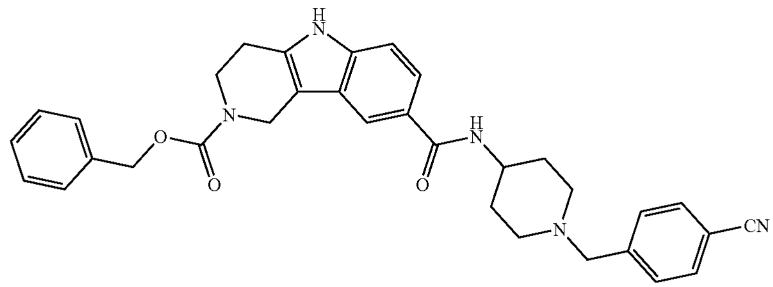 |
| 2 | benzyl 8-(1-(4-benzyl)piperidin-4-ylcarbamoyl)-3,4-dihydro-1H-pyrido[4,3-b]indole-2(5H)-carboxylate | 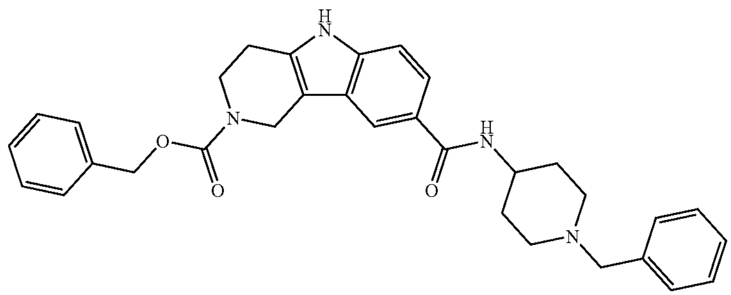 |
| 3 | benzyl 8-(1-(tert-butoxycarbonyl)piperidin-4-ylcarbamoyl)-3,4-dihydro-1H-pyrido[4,3-b]indole-2(5H)-carboxylate | 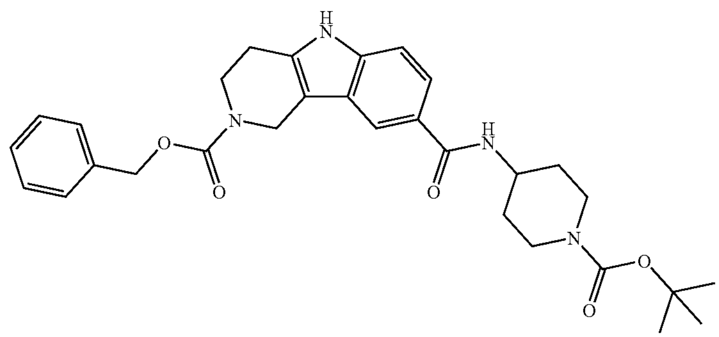 |
| 4 | 2-benzyl-N-(1-(4-cyanobenzyl)piperidin-4-yl)-2,3,4,5-tetrahydro-1H-pyrido[4,3-b]indole-8-carboxamide | 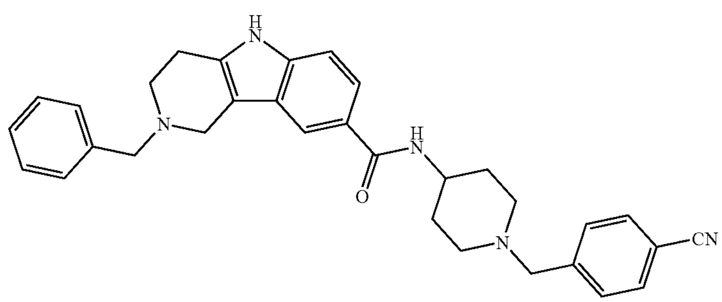 |
| 5 | 2-benzyl-N-(1-(4-trifluoromethylbenzyl)piperidin-4-yl)-2,3,4,5-tetrahydro-1H-pyrido[4,3-b]indole-8-carboxamide | 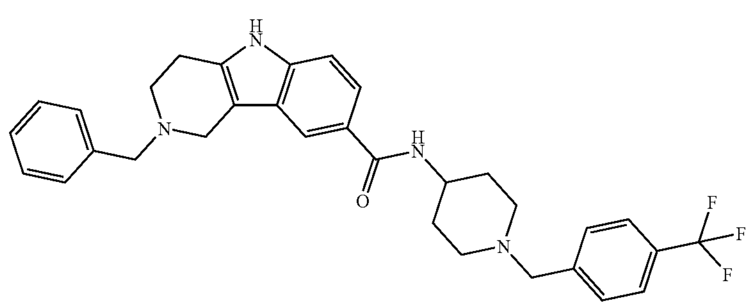 |

TABLE 1-continued

| No. | Name |
|---|---|
| 6 | tert-butyl 4-(2-(4-(trifluoromethyl)benzyl)-2,3,4,5-tetrahydro-1H-pyrido[4,3-b]indole-8-carboxamido)piperidine-1-carboxylate |
| 7 | 2-benzyl-N-(1-(pyridin-4-ylmethyl)piperidin-4-yl)-2,3,4,5-tetrahydro-1H-pyrido[4,3-b]indole-8-carboxamide |
| 8 | 2-(4-fluorobenzyl)-N-(1-(pyridin-3-ylmethyl)piperidin-4-yl)-2,3,4,5-tetrahydro-1H-pyrido[4,3-b]indole-8-carboxamide |
| 9 | N-(1-(4-cyanobenzyl)piperidin-4-yl)-2-(4-fluorobenzyl)-2,3,4,5-tetrahydro-1H-pyrido[4,3-b]indole-8-carboxamide |
| 10 | N-(1-(4-trifluoromethylbenzyl)piperidin-4-yl)-2-(4-fluorobenzyl)-2,3,4,5-tetrahydro-1H-pyrido[4,3-b]indole-8-carboxamide |

TABLE 1-continued

| No. | Name |
|---|---|
| 11 | N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide |
| 12 | N-(1-(4-cyanobenzyl)piperidin-4-yl)-2-(4-(trifluoromethyl)benzyl)-2,3,4,5-tetrahydro-1H-pyrido[4,3-b]indole-8-carboxamide |
| 13 | N-(1-(4-trifluoromethylbenzyl)piperidin-4-yl)-2-(4-(trifluoromethyl)benzyl)-2,3,4,5-tetrahydro-1H-pyrido[4,3-b]indole-8-carboxamide |
| 14 | N-(1-phenethylpiperidin-4-yl)-2-(4-(trifluoromethyl)benzyl)-2,3,4,5-tetrahydro-1H-pyrido[4,3-b]indole-8-carboxamide |
| 15 | N-(1-(4-fluorophenyl)piperidin-4-yl)-2-(4-(trifluoromethyl)benzyl)-2,3,4,5-tetrahydro-1H-pyrido[4,3-b]indole-8-carboxamide |

TABLE 1-continued

| No. | Name |
|---|---|
| 16 | N-(1-(4-cyanobenzyl)piperidin-4-yl)-5-methyl-2-(4-trifluoromethyl)benzyl)-2,3,4,5-tetrahydro-1H-pyrido[4,3-b]indole-8-carboxamide |
| 17 | N-(1-(4-trifluoromethylbenzyl)piperidin-4-yl)-5-methyl-2-(4-(trifluoromethyl)benzyl)-2,3,4,5-tetrahydro-1H-pyrido[4,3-b]indole-8-carboxamide |
| 18 | 5-methyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide |
| 19 | N-(1-benzylpiperidin-4-yl)-2-(4-(trifluoromethyl)phenylsulfonyl)-2,3,4,5-tetrahydro-1H-pyrido[4,3-b]indole-8-carboxamide |
| 20 | 5-acetyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide |

TABLE 1-continued

| No. | Name | Structure |
|---|---|---|
| 21 | N-(1-(4-cyanophenylsulfonyl)piperidin-4-yl)-2-(4-(trifluoromethyl)benzyl)-2,3,4,5-tetrahydro-1H-pyrido[4,3-b]indole-8-carboxamide | 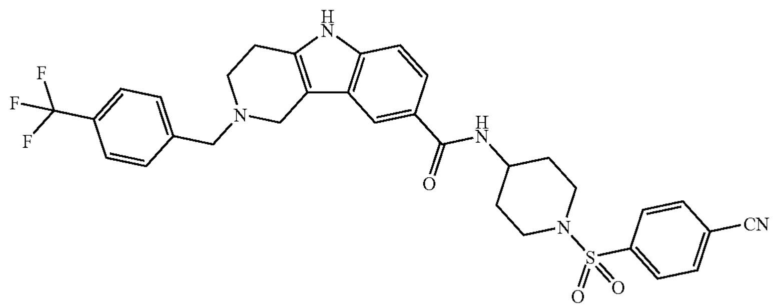 |
| 22 | N-(1-(pyridin-3-ylsulfonyl)piperidin-4-yl)-2-(4-(trifluoromethyl)benzyl)-2,3,4,5-tetrahydro-1H-pyrido[4,3-b]indole-8-carboxamide | 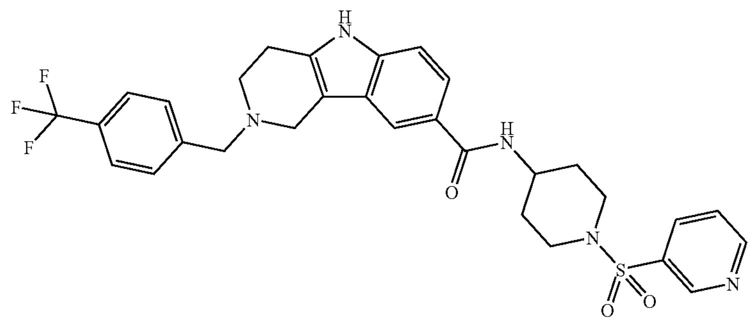 |
| 23 | 2-(4-(trifluoromethyl)benzyl)-N-(1-(4-(trifluoromethyl)phenylsulfonyl)piperidin-4-yl)-2,3,4,5-tetrahydro-1H-pyrido[4,3-b]indole-8-carboxamide | 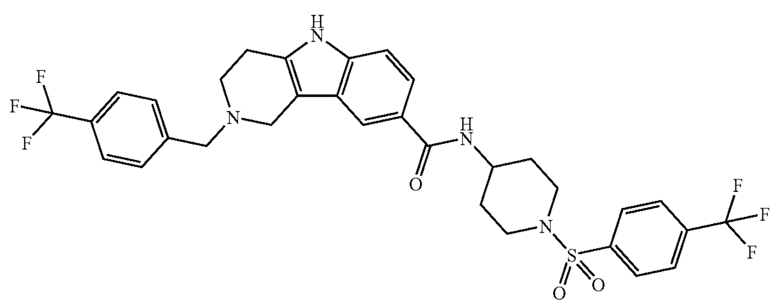 |
| 24 | N-(1-(4-cyanobenzyl)piperidin-4-yl)-2-(4-(trifluoromethyl)phenylsulfonyl)-2,3,4,5-tetrahydro-1H-pyrido[4,3-b]indole-8-carboxamide | 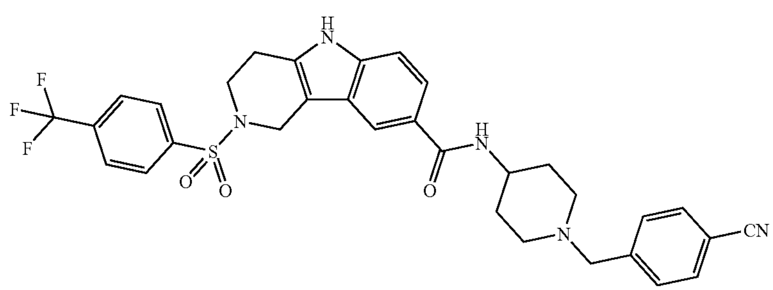 |
| 25 | N-(1-(4-cyanobenzyl)piperidin-4-yl)-2-(4-cyanophenylsulfonyl)-2,3,4,5-tetrahydro-1H-pyrido[4,3-b]indole-8-carboxamide | 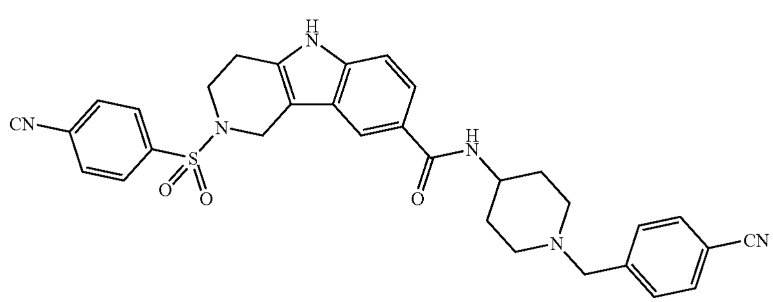 |

TABLE 1-continued

| No. | Name | Structure |
|---|---|---|
| 26 | N-(1-(4-cyanobenzyl)piperidin-4-yl)-2-(pyridin-3-ylsulfonyl)-2,3,4,5-tetrahydro-1H-pyrido[4,3-b]indole-8-carboxamide | 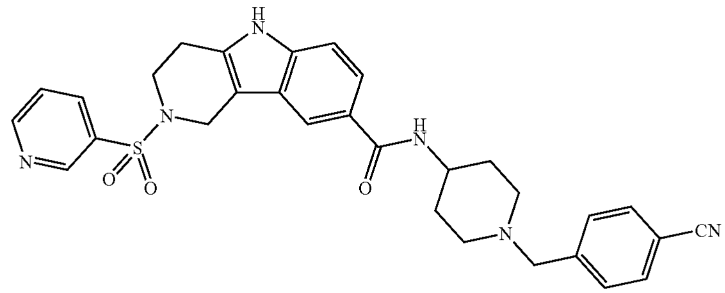 |
| 27 | N-(1-(4-cyanophenylcarbamoyl)piperidin-4-yl)-2-(4-(trifluoromethyl)benzyl)-2,3,4,5-tetrahydro-1H-pyrido[4,3-b]indole-8-carboxamide | 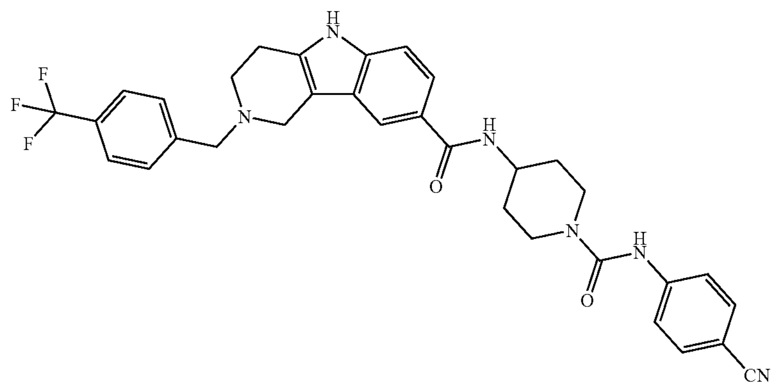 |
| 28 | N-(1-(4-fluorophenylsulfonyl)piperidin-4-yl)-2-(4-(trifluoromethyl)benzyl)-2,3,4,5-tetrahydro-1H-pyrido[4,3-b]indole-8-carboxamide | 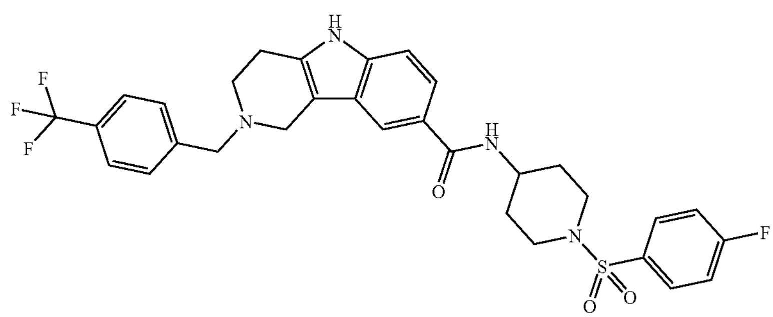 |
| 29 | N-(1-(3-cyanophenylsulfonyl)piperidin-4-yl)-2-(4-(trifluoromethyl)benzyl)-2,3,4,5-tetrahydro-1H-pyrido[4,3-b]indole-8-carboxamide | 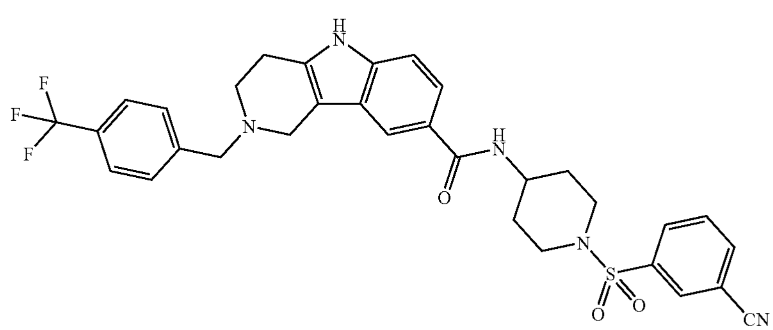 |

TABLE 1-continued

| No. | Name | Structure |
|---|---|---|
| 30 | 2-(4-(trifluoromethyl)benzyl)-N-(1-(3-(trifluoromethyl)phenylsulfonyl)piperidin-4-yl)-2,3,4,5-tetrahydro-1H-pyrido[4,3-b]indole-8-carboxamide | 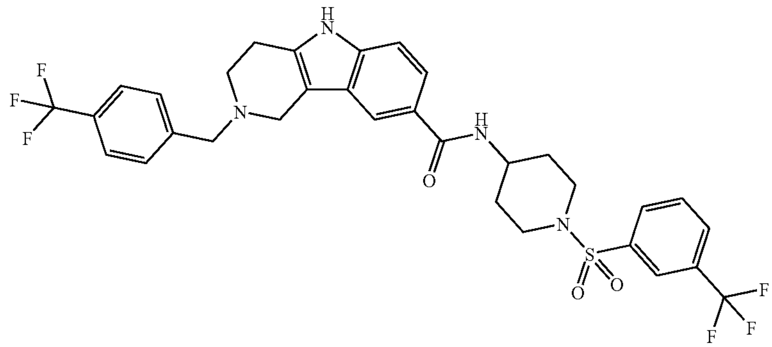 |
| 31 | N-(1-(3-fluorophenylcarbamoyl)piperidin-4-yl)-2-(4-(trifluoromethyl)benzyl)-2,3,4,5-tetrahydro-1H-pyrido[4,3-b]indole-8-carboxamide | 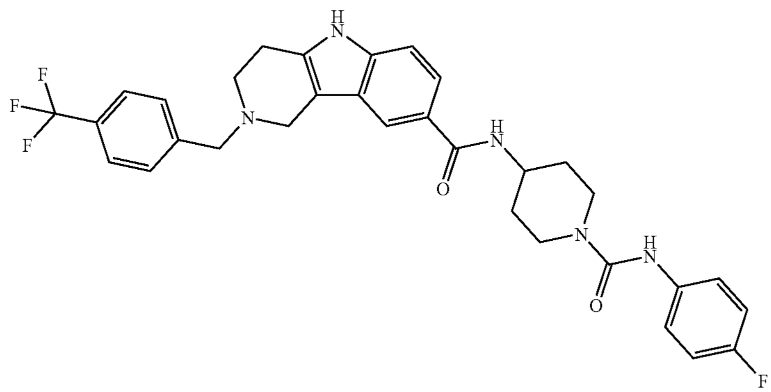 |
| 32 | N-(1-(4-chlorophenylsulfonyl)piperidin-4-yl)-2-(4-(trifluoromethyl)benzyl)-2,3,4,5-tetrahydro-1H-pyrido[4,3-b]indole-8-carboxamide | 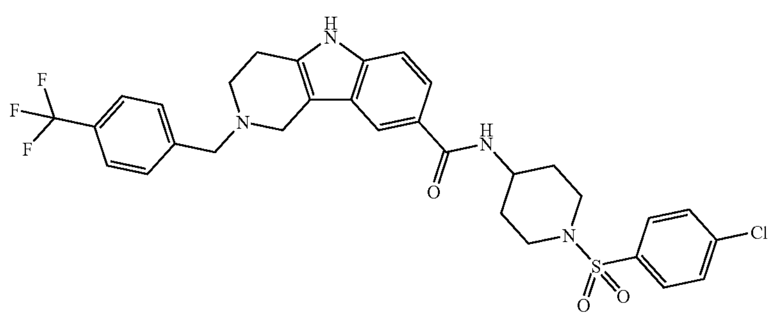 |
| 33 | 2-(4-(trifluoromethyl)benzyl)-N-(1-(4-(trifluoromethyl)phenylcarbamoyl)piperidin-4-yl)-2,3,4,5-tetrahydro-1H-pyrido[4,3-b]indole-8-carboxamide | 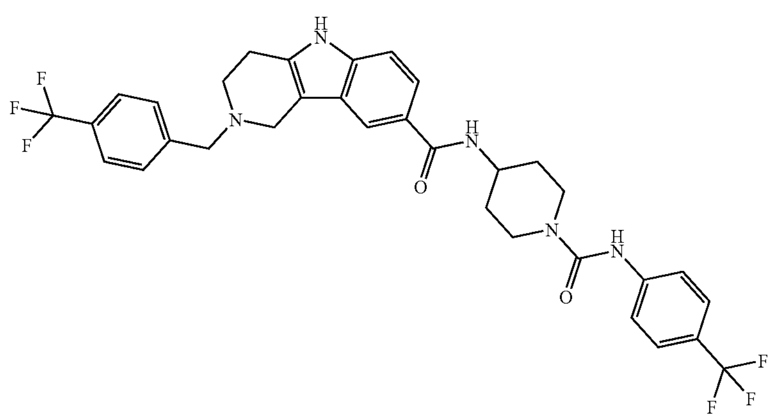 |

TABLE 1-continued

| No. | Name | Structure |
|-----|------|-----------|
| 34 | N-(1-(4-cyanobenzyl)piperidin-4-yl)-2-(4-fluorophenyl)-2,3,4,5-tetrahydro-1H-pyrido[4,3-b]indole-8-carboxamide | 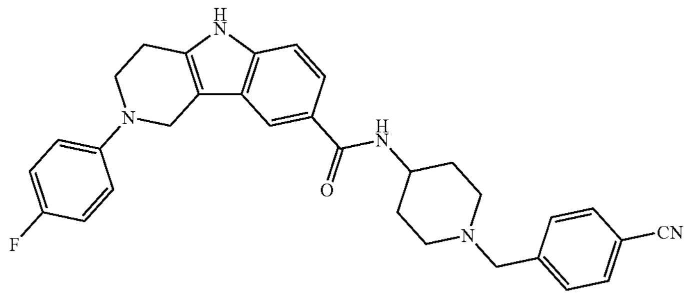 |
| 35 | 2-(4-fluorophenyl)-N-(1-(4-fluorophenylsulfonyl)piperidin-4-yl)-2,3,4,5-tetrahydro-1H-pyrido[4,3-b]indole-8-carboxamide | 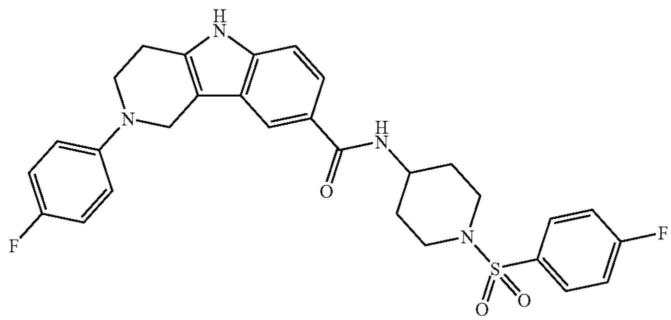 |
| 36 | 2-(4-fluorophenyl)-N-(1-(pyridin-3-ylmethyl)piperidin-4-yl)-2,3,4,5-tetrahydro-1H-pyrido[4,3-]indole-8-carboxamide | 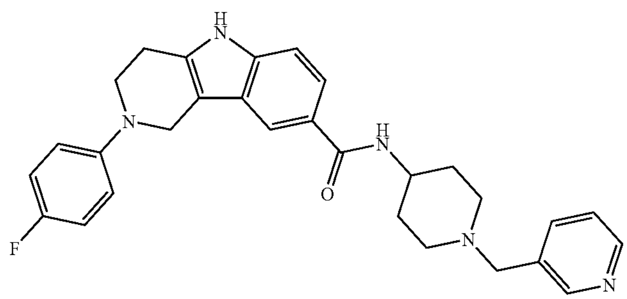 |
| 37 | 2-(4-fluorophenyl)-N-(1-(4-(trifluoromethyl)benzyl)piperidin-4-yl)-2,3,4,5-tetrahydro-1H-pyrido[4,3-b]indole-8-carboxamide | 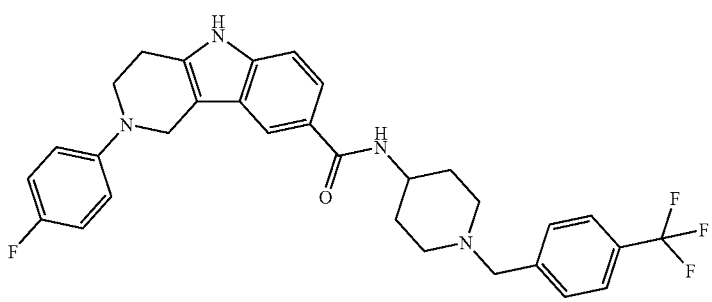 |
| 38 | tert-butyl 4-(2-(4-fluorophenyl)-2,3,4,5-tetrahydro-1H-pyrido[4,3-b]indole-8-carboxamido)piperidine-1-carboxylate | 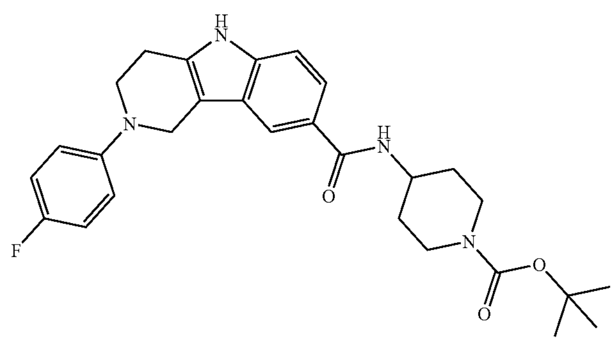 |

TABLE 1-continued

| No. | Name |
|---|---|
| 39 | N-(1-(4-fluorobenzoyl)piperidin-4-yl)-2-(4-fluorophenyl)-2,3,4,5-tetrahydro-1H-pyrido[4,3-b]indole-8-carboxamide |
| 40 | 2-(4-fluorophenyl)-N-(1-nicotinoylpiperidin-4-yl)-2,3,4,5-tetrahydro-1H-pyrido[4,3-b]indole-8-carboxamide |
| 41 | 2-(4-fluorophenyl)-N-(1-(4-(trifluoromethyl)benzoyl)piperidin-4-yl)-2,3,4,5-tetrahydro-1H-pyrido[4,3-b]indole-8-carboxamide |
| 42 | N-(1-nicotinoylpiperidin-4-yl)-2-(4-(trifluoromethyl)benzyl)-2,3,4,5-tetrahydro-1H-pyrido[4,3-b]indole-8-carboxamide |

TABLE 1-continued

| No. | Name |
|---|---|
| 43 | tert-butyl 4-(2-(4-carbamoylbenzyl)-2,3,4,5-tetrahydro-1H-pyrido[4,3-b]indole-8-carboxamido)piperidine-1-carboxylate |
| 44 | 2-(4-carbamoylbenzyl)-N-(1-(4-cyanobenzyl)piperidin-4-yl)-2,3,4,5-tetrahydro-1H-pyrido[4,3-b]indole-8-carboxamide |
| 45 | 2-(4-carbamoylbenzyl)-N-(1-(pyridin-4-ylmethyl)piperidin-4-yl)-2,3,4,5-tetrahydro-1H-pyrido[4,3-b]indole-8-carboxamide |
| 46 | 2-(4-carbamoylbenzyl)-N-(1-isonicotinoylpiperidin-4-yl)-2,3,4,5-tetrahydro-1H-pyrido[4,3-b]indole-8-carboxamide |
| 47 | 2-(4-carbamoylbenzyl)-N-(1-(4-(trifluoromethyl)benzyl)piperidin-4-yl)-2,3,4,5-tetrahydro-1H-pyrido[4,3-b]indole-8-carboxamide |

TABLE 1-continued

| No. | Name | Structure |
|---|---|---|
| 48 | 2-(4-carbamoylbenzyl)-N-(1-(4-fluorobenzyl)piperidin-4-yl)-2,3,4,5-tetrahydro-1H-pyrido[4,3-b]indole-8-carboxamide | 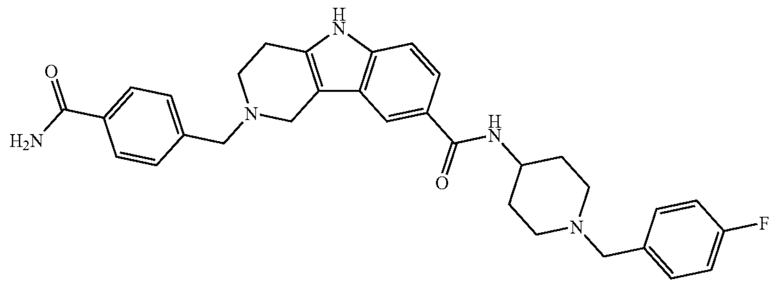 |
| 49 | 2-(4-carbamoylbenzyl)-N-(1-(4-carbamoylbenzyl)piperidin-4-yl)-2,3,4,5-tetrahydro-1H-pyrido[4,3-b]indole-8-carboxamide | 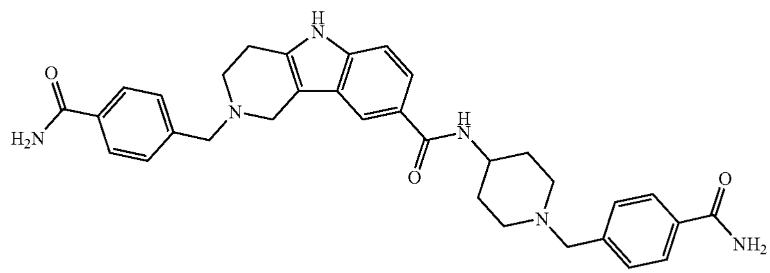 |
| 50 | N-(1-(pyridin-4-ylmethyl)piperidin-4-yl)-2-(4-(trifluoromethyl)benzyl)-2,3,4,5-tetrahydro-1H-pyrido[4,3-b]indole-8-carboxamide | 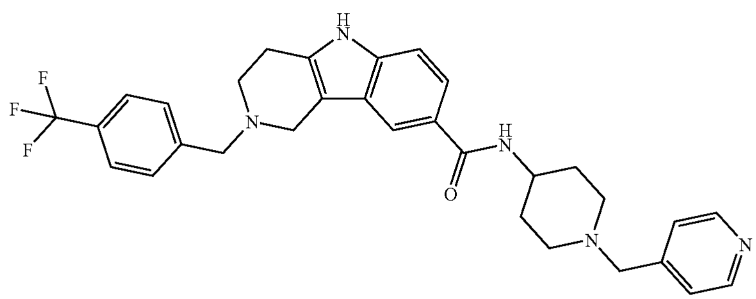 |
| 51 | N-(1-isonicotinoylpiperidin-4-yl)-2-(4-(trifluoromethyl)benzyl)-2,3,4,5-tetrahydro-1H-pyrido[4,3-b]indole-8-carboxamide | 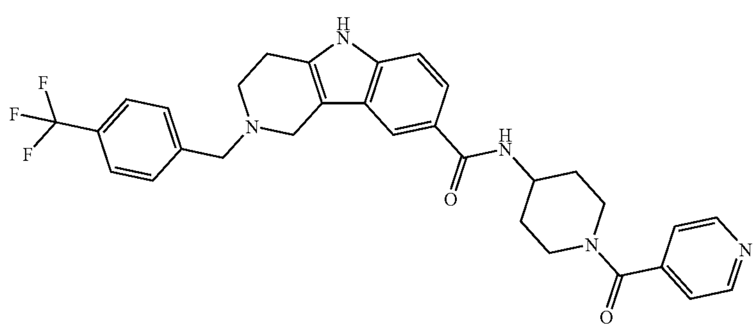 |
| 52 | N-(1-(4-carbamoylbenzyl)piperidin-4-yl)-2-(4-(trifluoromethyl)benzyl)-2,3,4,5-tetrahydro-1H-pyrido[4,3-b]indole-8-carboxamide | 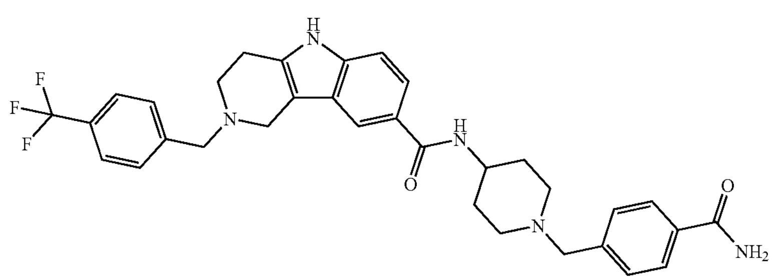 |

TABLE 1-continued

| No. | Name | Structure |
|---|---|---|
| 53 | N-(1-((1-methyl-1H-imidazol-4-yl)methyl)piperidin-4-yl)-2-(4-(trifluoromethyl)benzyl)-2,3,4,5-tetrahydro-1H-pyrido[4,3-b]indole-8-carboxamide | 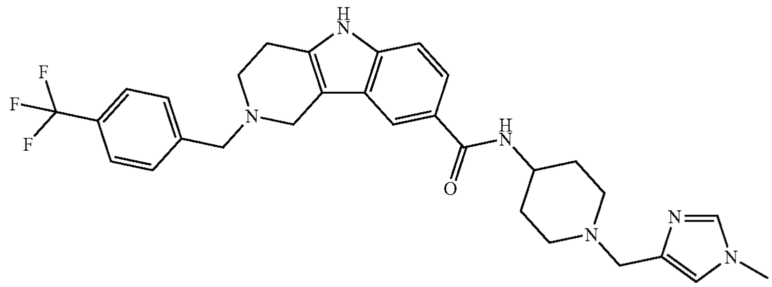 |
| 54 | N-(1-(oxazol-4-ylmethyl)piperidin-4-yl)-2-(4-(trifluoromethyl)benzyl)-2,3,4,5-tetrahydro-1H-pyrido[4,3-b]indole-8-carboxamide | 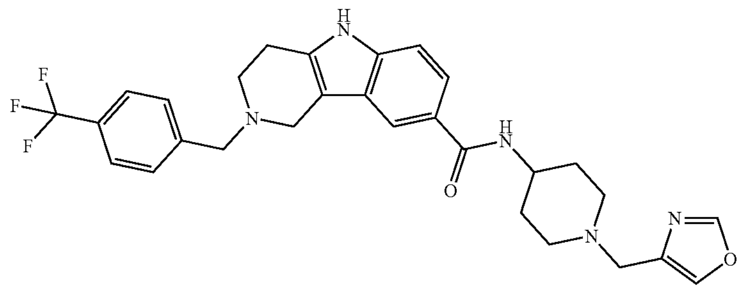 |
| 55 | 4-((4-benzylpiperazin-1-yl)methyl)-N-(1-benzylpiperidin-4-yl)benzamide | 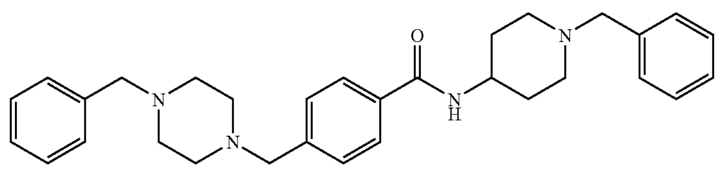 |
| 56 | N-(1-benzylpiperidin-4-yl)-4-((4-(cyclohexylmethyl)piperazin-1-yl)methyl)benzamide | 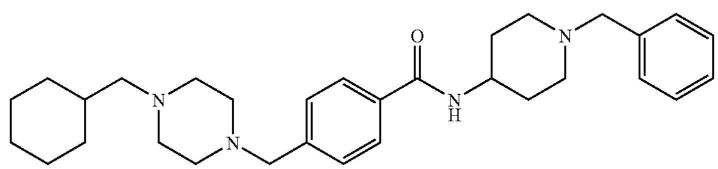 |
| 57 | N-(1-benzylpiperidin-4-yl)-4-((4-(5-(trifluoromethyl)pyridin-2-yl)piperazin-1-yl)methyl)benzamide | 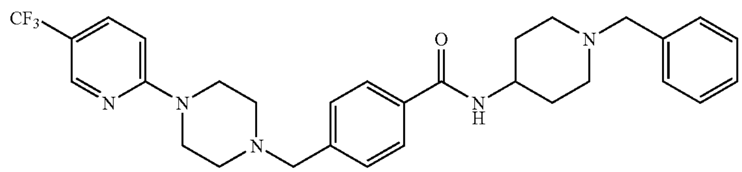 |
| 58 | N-(1-benzylpiperidin-4-yl)-4-((4-(pyridin-2-yl)piperazin-1-yl)methyl)benzamide | 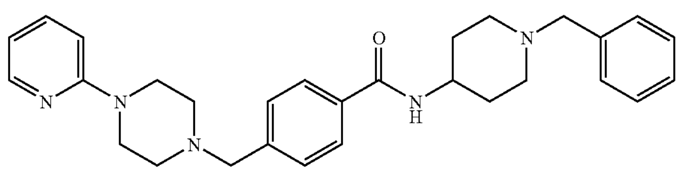 |
| 59 | 4-((4-benzylpiperazin-1-yl)methyl)-N-(1-(pyridin-4-ylmethyl)piperidin-4-yl)benzamide | 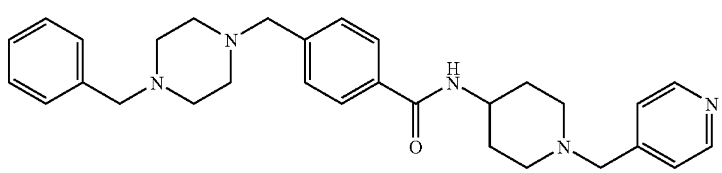 |

TABLE 1-continued

| No. | Name | Structure |
|-----|------|-----------|
| 60 | 4-((4-benzylpiperazin-1-yl)methyl)-N-(1-(pyridin-3-ylmethyl)piperidin-4-yl)benzamide | 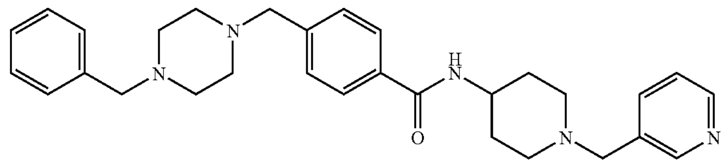 |
| 61 | 4-((4-benzylpiperazin-1-yl)methyl)-N-(1-(4-cyanobenzyl)piperidin-4-yl)benzamide | 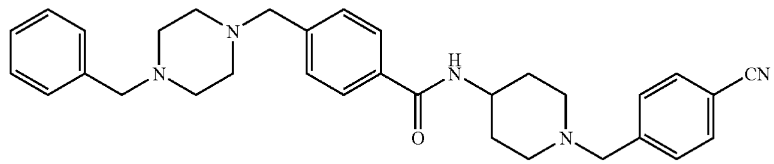 |
| 62 | 4-((4-benzylpiperazin-1-yl)methyl)-N-(1-(4-trifluoromethylbenzyl)piperidin-4-yl)benzamide | 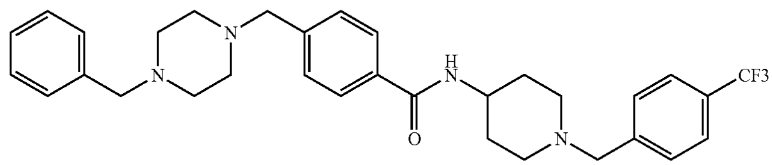 |
| 63 | N-(1-benzylpiperidin-4-yl)-6-(1-(4-(trifluoromethyl)benzyl)piperidin-4-yloxy)-2-naphthamide | 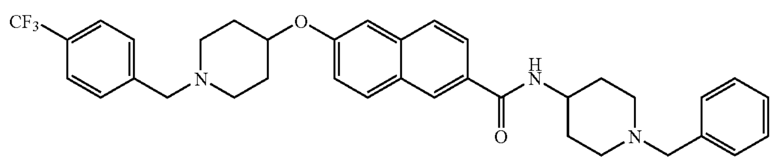 |
| 64 | N-(1-benzylpiperidin-4-yl)-6-(1-(4-cyanobenzyl)piperidin-4-yloxy)-2-naphthamide | 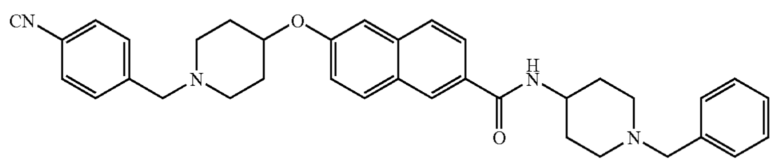 |
| 65 | N-(1-benzylpiperidin-4-yl)-6-(1-(4-(trifluoromethyl)phenyl)piperidin-4-yloxy)-2-naphthamide | 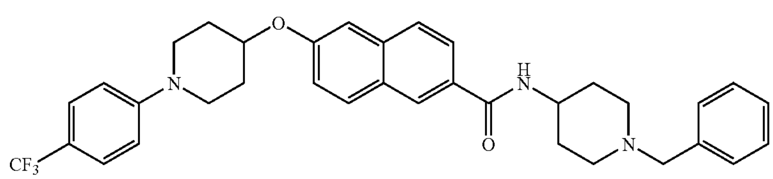 |
| 66 | tert-butyl 4-(7-(1-(4-(trifluoromethyl)phenyl)piperidin-4-yloxy)-2-naphthamido)piperidine-1-carboxylate | 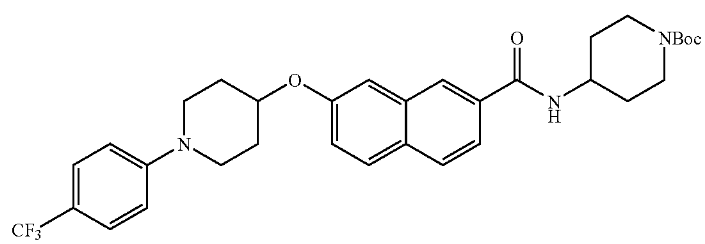 |
| 67 | tert-butyl 4-(6-(1-(4-(trifluoromethyl)phenyl)piperidin-4-yloxy)quinoline-3-carboxamido)piperidine-1-carboxylate | 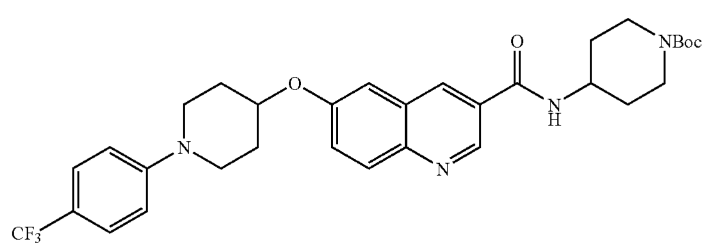 |

TABLE 1-continued

| No. | Name | Structure |
|---|---|---|
| 68 | N-(piperidin-4-yl)-6-(1-(4-(trifluoromethyl)phenyl)piperidin-4-yloxy)quinoline-3-carboxamide | 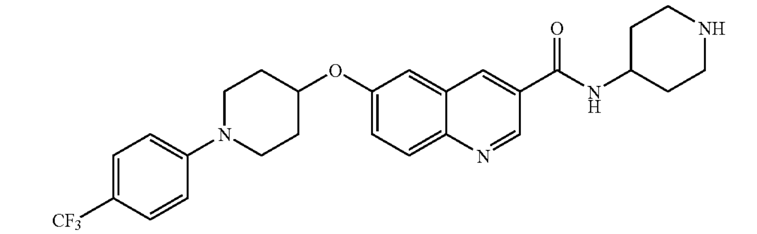 |
| 69 | N-(1-(4-cyanobenzyl)piperidin-4-yl)-6-(1-(4-(trifluoromethyl)phenyl)piperidin-4-yloxy)quinoline-3-carboxamide | 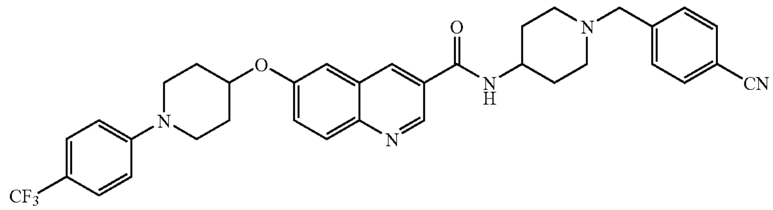 |
| 70 | N-(1-(4-(trifluoromethyl)benzyl)piperidin-4-yl)-6-(1-(4-(trifluoromethyl)phenyl)piperidin-4-yloxy)quinoline-3-carboxamide | 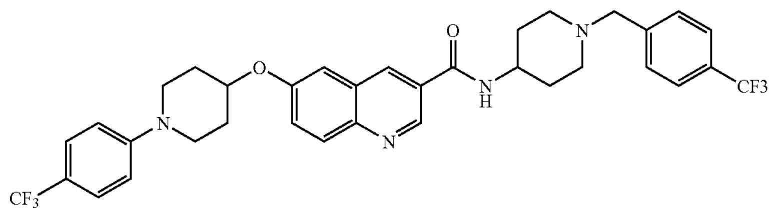 |
| 71 | N-(1-benzylpiperidin-4-yl)-6-(1-(4-(trifluoromethyl)phenyl)piperidin-4-yloxy)quinoline-3-carboxamide | 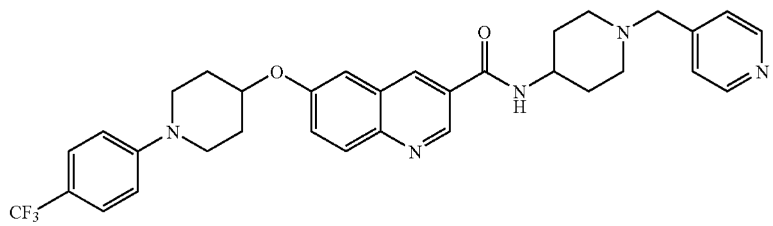 |
| 72 | N-(1-benzylpiperidin-4-yl)-5-(1-(4-(trifluoromethyl)phenyl)piperidin-4-yloxy)-1H-indole-2-carboxamide | 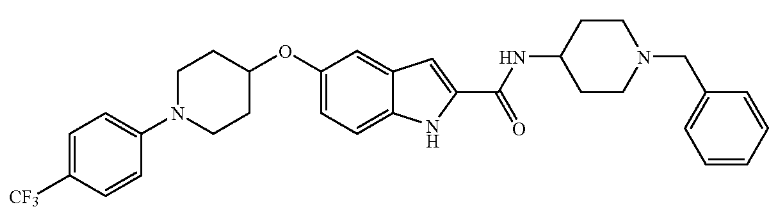 |

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B-, wherein a is 0 or 1. In such instances, when a is 0 the moiety is B- and when a is 1 the moiety is A-B-.

As used herein, the term "alkyl" includes alkyl, alkenyl and alkynyl groups of a designed number of carbon atoms, desirably from 1 to about 12 carbons (i.e., inclusive of 1 and 12). The term "$C_m$-$C_n$ alkyl" means an alkyl group having from m to n carbon atoms (i.e., inclusive of m and n). The term "$C_m$-$C_n$ alkyl" means an alkyl group having from m to n carbon atoms. For example, "$C_1$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-

C₆ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic carbocyclic ring system having a single ring (e.g., phenyl) which is optionally fused to other aromatic hydrocarbon rings or non-aromatic hydrocarbon rings. "Aryl" includes ring systems having multiple condensed rings and in which at least one is aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, 2,3-dihydrobenzofuranyl and 6,7,8,9-tetrahydro-5H-benzo[a]cycloheptenyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Preferred cycloalkyl groups have from 3 to 7 members in a single ring. More preferred cycloalkyl groups have 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —O$^-$M$^+$, =O, —OR$^{70}$, —SR$^{70}$, —S$^-$M$^+$, =S, —NR$^{80}$R$^{80}$, =NR$^{70}$, =N—OR$^{70}$, trihalomethyl, —CF$_3$, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)R$^{70}$, —C(S)R$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, NR$^{70}$C(NR$^{70}$)R$^{70}$ and —NR$^{70}$C(NR$^{70}$)NR$^{80}$R$^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}$R$^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2$R$^7$, —SO$_2$O$^-$M$^+$, —SO$_2$OR$^{71}$, —OSO$_2$R$^{71}$, —OSO$_2$O$^-$M$^+$, —OSO$_2$OR$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O M$^+$, —C(O)OR$^{71}$, —C(S)R$^{71}$, —C(O)NR$^{81}$R$^{81}$, —C(NR$^{71}$)NR$^{81}$R$^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, —NR$^{71}$C(S)R$^{71}$, —NR$^{71}$CO$_2$$^-$M$^+$, —NR$^{71}$CO$_2$R$^{71}$, —NR$^{71}$C(S)OR$^{71}$, —NR$^{71}$C(O)NR$^{81}$R$^{81}$, —NR$^{71}$C(NR$^{71}$)R$^{71}$ and —NR$^{71}$C(NR$^{71}$)NR$^{81}$R$^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M$^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, OR$^{72}$, —SR$^{72}$, S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^2$R$^2$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2$$^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each $R^{81}$ is independently $R^{71}$ or alternatively, two $R^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$ alkyl) or ($C_1$-$C_6$ fluoroalkyl); each $R^{82}$ is independently $R^{72}$ or alternatively, two $R^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each M$^+$ may independently be, for example, an alkali ion, such as K$^+$, Na$^+$, Li$^+$; an ammonium ion, such as $^+$N($R^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$M$^+$, —OSO$_3$R$^{70}$, —PO$_3$$^{-2}$(M$^+$)$_2$, —P(O)(OR$^{70}$)O M$^+$, —P(O)(OR$^{70}$)$_2$, —C(O)R$^{70}$, —C(S)R$^{70}$, —C(NR$^{70}$)R$^{70}$, —CO$_2$ M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where $R^{60}$, $R^{70}$, $R^{80}$ and M$^+$ are as previously defined.

Substituent groups for hydrogens on nitrogen atoms in "substituted" heteroalkyl and heterocycloalkyl groups are, unless otherwise specified, —$R^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{80}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where $R^{60}$, $R^{70}$, $R^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, 1, or d1), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

Compounds can be assayed for binding to a membrane-bound adiponectin receptor by performing a competitive binding assay with adiponectin. In one such procedure, HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands are washed away and the degree of binding of the adiponectin is determined using horseradish peroxidase-conjugated anti-polyhistidine. Compounds that compete with adiponectin binding to the membrane (i.e., give a reduced signal compared to a control performed without a candidate compound) can be chosen as hits and further screened using the below-described functional assays to identify adiponectin receptor agonists.

An in-cell western assay can be performed to demonstrate the activation of AMPK in human liver cells by globular adiponectin using glutathione S-transferase (GST). AMPK activity can be measured by the relative concentration of phosphorylated acetyl Co-A carboxylase, which is one of the products of AMPK. An increase in pACC correlates with an increase in the rate of fatty acid oxidation.

The compounds of structural formulae (I)-(LXIX) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(LXIX).

In the pharmaceutical compositions disclosed herein, one or more compounds of structural formulae (I)-(LXIX) may be present in association with one or more pharmaceutically acceptable carriers, diluents or excipients, and, if desired, other active ingredients. The pharmaceutical compositions containing compounds of structural formulae (I)-(LXIX) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(LXIX) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(LXIX) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compounds disclosed herein can be made using procedures familiar to the person of ordinary skill in the art and as described herein. For example, compounds of structural formulae (II)-(III) can be prepared according to Scheme 1, below, or analogous synthetic schemes:

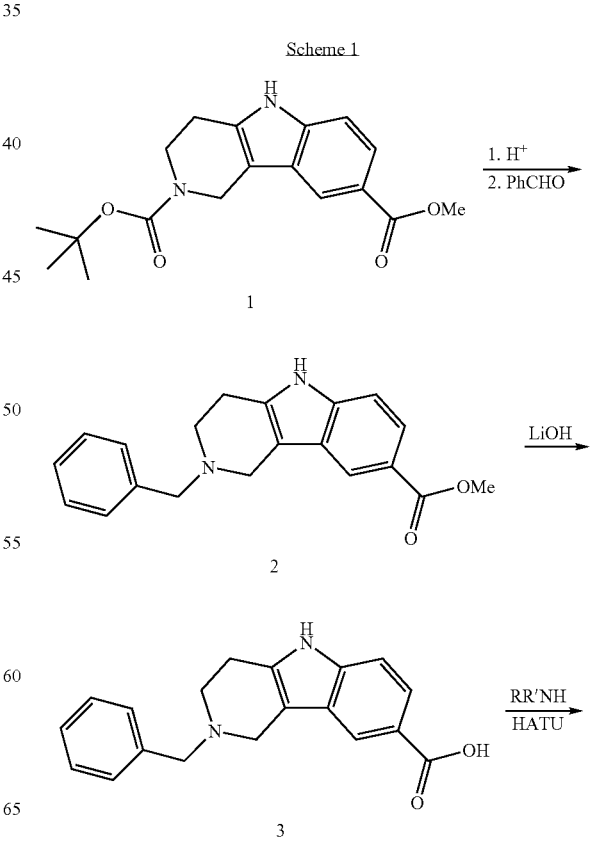

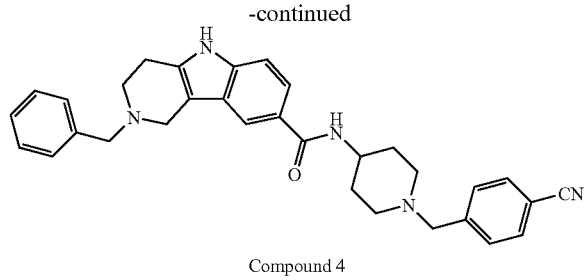

Compound 4

Referring to Scheme 1, BOC-protected tetrahydro-1H-pyrido[4,3-b]indolecarboxylate ester 1, for example, is de-BOC'd and coupled with a benzaldehyde via e.g. reductive amination to form benzyl-substituted compound 2. The ester is saponified and protonated to form the corresponding carboxylic acid 3, which is then coupled with a suitable amine (in this case, a substituted 1-benzylpiperidin-4-amine) to form Compound 4 of Table 1. Examples of the syntheses of compounds according to structural formula (III) are provided below in Example 1.

Compounds of structural formula (IV)-(V) can be prepared according to Scheme 2, below, or analogous synthetic schemes:

Scheme 2

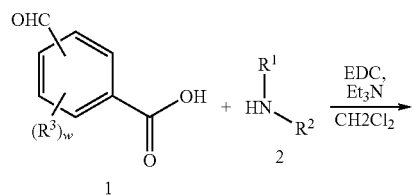

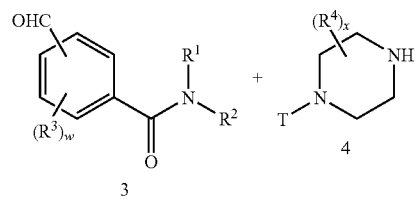

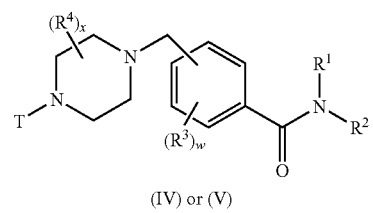

(IV) or (V)

Referring to Scheme 2, aldehydic acid 1, for example, can be coupled with amine 2 to provide amide 3. Amide 3 in turn can be reductively coupled with piperazine 4 to provide compounds of structural formulae (IV) or (V). An example of the synthesis of a compound of structural formula (IV) is provided below in Example 2.

Compounds of structural formulae (VI)-(VII) can be prepared according to Scheme 3, below, or analogous synthetic schemes:

Scheme 3

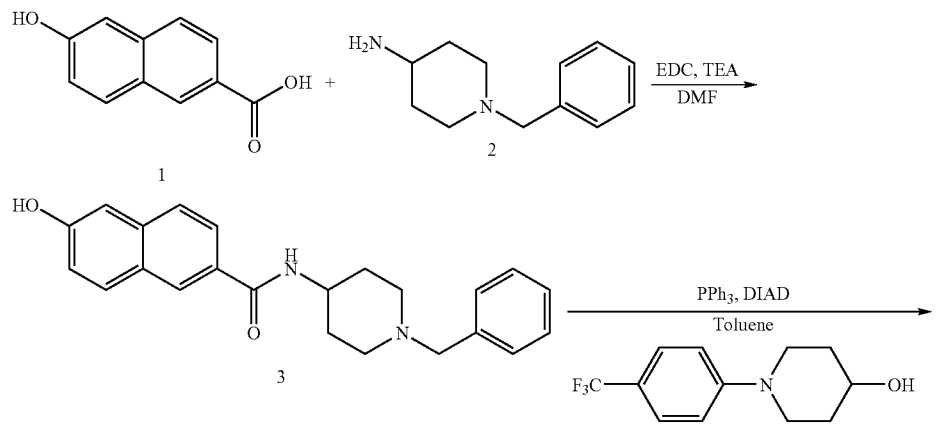

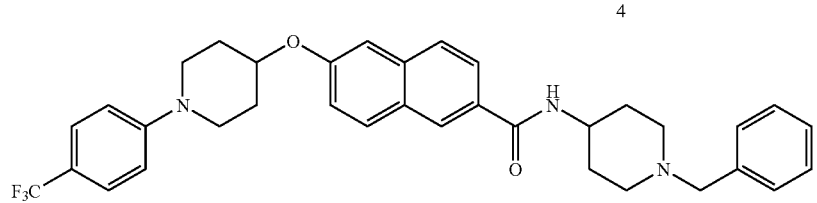

Compound 65

Referring to Scheme 3, hydroxynaphthoic acid 1, for example, is coupled with a protected (e.g. benzyl) 4-aminopiperidine 2 to form N-piperidin-4-yl naphthamide 3, which is coupled with 4-hydroxypiperidine 4, for example under Mitsunobu conditions, to form Compound 65 of Table 1. An example of the synthesis of a compound of structural formula (VI) is provided below in Example 3.

Compounds of structural formulae (VII)-(IX) can be prepared according to Scheme 4, below, or analogous synthetic schemes:

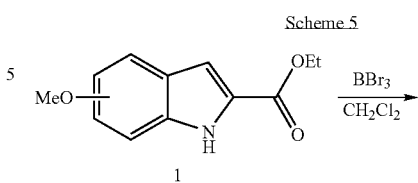

Scheme 5

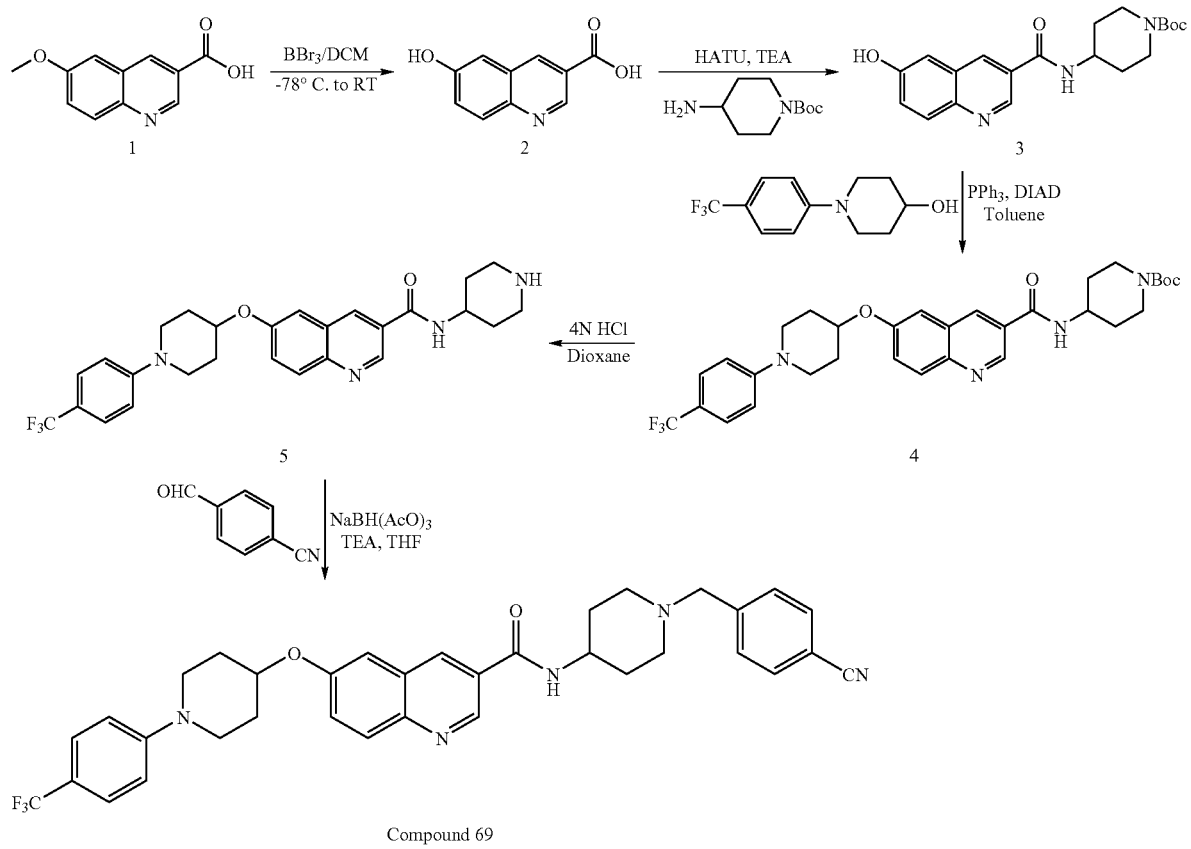

Scheme 4

Compound 69

Referring to Scheme 4, methoxyquinolinecarboxylic acid 1, for example, is converted to the corresponding hydroxyquinolinecarboxylic acid 2, by removal of the methyl group with, e.g., boron tribromide. The acid moiety is coupled with Boc-protected 4-aminopiperidine to form protected N-piperidin-4-yl quinolinecarboxamide 3. Coupling of the hydroxyl group of 3 with a desired 4-hydroxypiperidine yields Boc-protected compound 4, which is deprotected to yield the N-piperidin-4-yl piperidinyloxyquinolinecarboxamide 5. Reductive amination of a benzaldehyde with the amide pipiridine yields Compound 69 of Table 1. An example of the synthesis of a compound of structural formula (IX) is provided below in Example 4.

Compounds of structural formulae (X)-(XI) can be prepared according to Scheme 5, below, or analogous synthetic schemes:

-continued

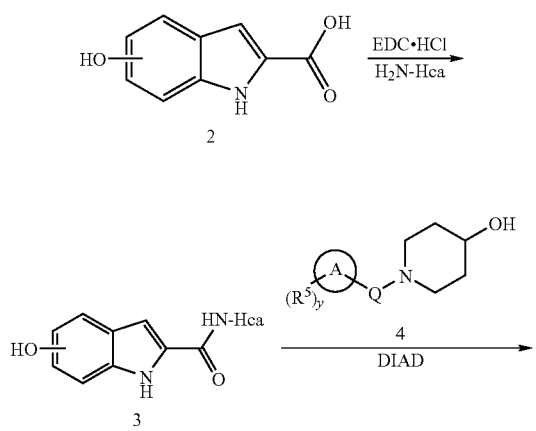

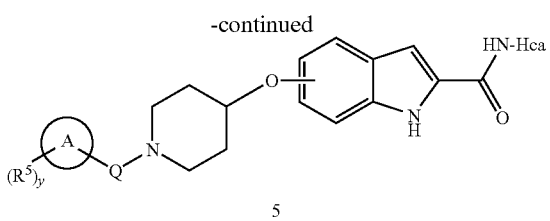

5

Referring to Scheme 5, methoxyindole ester 1, for example, is converted to the corresponding hydroxyindole carboxylic acid 2 with boron tribromide. Carboxylic acid 2 is coupled with Hca amine to yield hydroxyindole amide 3. Hydroxyazacycloalkanol 4 (illustrated as a 4-hydroxypiperidine) is coupled with amide 3 to yield (azacycloalkoxy)benzoindoleamide 5. An example of the synthesis of a compound of structural formula (X) is provided below in Example 5.

One of skill in the art can adapt the reaction sequences of Schemes 1-5 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(LXIX) can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

While not intending to be bound by theory, the inventors surmise that compounds of structural formulae (I)-(LXIX) are mimics of adiponectin which act as adiponectin receptor agonists, thereby activating the AMPK pathway. Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, compounds of structural formulae (I)-(LXIX) should also inhibit the inflammatory processes which occur during the early phases of atherosclerosis. Accordingly, compounds of structural formulae (I)-(LXIX) can be useful in the treatment of type II diabetes and in the treatment and prevention of atherosclerosis, cardiovascular disease, obesity and non-alcoholic fatty liver disease.

Accordingly, another aspect of the present disclosure relates to a method of activating the AMPK pathway. According to this aspect, a method for activating the AMPK pathway in a cell includes contacting the cell with an effective amount of a compound, pharmaceutically acceptable salt, prodrug, N-oxide (or solvate or hydrate thereof) or composition described above.

In one embodiment, a method of increasing fatty acid oxidation in a cell includes contacting the cell with an effective amount of a compound, pharmaceutically acceptable salt, prodrug, N-oxide (or solvate or hydrate thereof) or composition described above. Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because the presently disclosed compounds can increase the rate of phosphorylation of ACC, they can reduce the inhibition of fatty acid oxidation and therefore increase its overall rate.

In another embodiment, a method of decreasing glycogen concentration in a cell includes contacting the cell with an effective amount of a compound, pharmaceutically acceptable salt, prodrug, N-oxide (or solvate or hydrate thereof) or composition described above.

In another embodiment, a method of increasing glucose uptake in a cell includes contacting the cell with an effective amount of a compound, pharmaceutically acceptable salt, prodrug, N-oxide (or solvate or hydrate thereof) or composition described above.

In another embodiment, a method of reducing triglyceride levels in a subject includes administering to the subject an effective amount of a compound, pharmaceutically acceptable salt, prodrug, N-oxide (or solvate or hydrate thereof) or composition described above.

In another embodiment, a method of increasing insulin sensitivity of a subject includes administering to the subject an effective amount of a compound, pharmaceutically acceptable salt prodrug, N-oxide (or solvate or hydrate thereof) or composition described above.

Accordingly, the compounds and compositions disclosed herein can be used to treat a variety of metabolic disorders. For example, in one embodiment, a method of treating type II diabetes in a subject in need of such treatment includes administering to the subject an effective amount of a compound, pharmaceutically acceptable salt, prodrug, solvate, hydrate, N-oxide or composition described above. In another embodiment, a method of treating or preventing atherosclerosis or cardiovascular disease in a subject includes administering to the subject an effective amount of a compound, pharmaceutically acceptable salt, prodrug, N-oxide (or solvate or hydrate thereof) or composition described above.

As described above, the compounds disclosed herein can act as activators of the AMPK pathway. Accordingly, in another embodiment, a method comprises modulating the AMPK pathway (either in vitro or in vivo) by contacting a cell with a compound, pharmaceutically acceptable salt, prodrug, N-oxide (or solvate or hydrate thereof) or composition described above, or administering a compound, pharmaceutically acceptable salt, prodrug, N-oxide (or solvate or hydrate thereof) or composition described above to a mammal (e.g., a human) in an amount sufficient to modulate the AMPK activity and study the effects thereby induced. Such methods are useful for studying the AMPK pathway and its role in biological mechanisms and disease states both in vitro and in vivo.

Another embodiment is the use of a compound, pharmaceutically acceptable salt, prodrug, N-oxide (or solvate or hydrate thereof) or composition as described above in the manufacture of a medicament for any of the therapeutic purposes described above. For example, the medicament can be for the reduction of triglyceride levels in a subject, the treatment of type II diabetes in a subject, or the treatment or prevention of atherosclerosis or cardiovasclular disease in a subject.

The compounds disclosed herein can be linked to labeling agents, for example for use in variety of experiments exploring their receptor binding, efficacy and metabolism. Accordingly, another embodiment is a labeled conjugate comprising a compound as disclosed herein covalently linked to a labeling agent, optionally through a linker. Suitable linker and labeling agents will be readily apparent to those of skill in the art upon consideration of the present disclosure. The labeling agent can be, for example, an affinity label such as biotin or strepavidin, a hapten such as digoxigenin, an enzyme such as a peroxidase, or a fluorophoric or chromophoric tag. Any suitable linker can be used. For example, in some embodiments, an ethylene glycol, oligo(ethylene glycol) or poly(ethylene glycol) linker is used. Other examples of linkers include amino acids, which can be used alone or in combination with other linker groups, such as ethylene glycol, oligoethylene glycol or polyethylene glycol. Suitable linkers include, without limitation, single amino acids, as well as di- and tripeptides. In one embodiment, the linker includes a glycine residue. The person of skill in the art will realize, of course, that other linkers and labeling agents can be used. In other embodiments, an alkylene chain is the linker. In other embodiments, the linker has the structure —[($C_0$-$C_3$ alkyl)-$Y^m$—]$_m$—, in which each $Y^m$ is —O—, —N($R^9$)—, or L, and m is in the range of 1-40. For example, in certain embodiments, a labeled conjugate has structural formula (LXX):

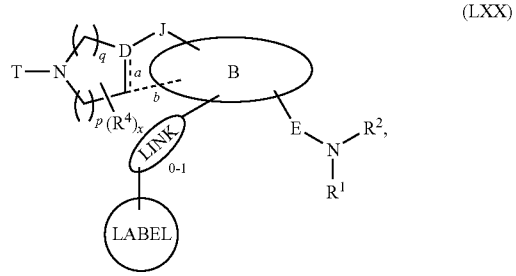

(LXX)

in which the "LINK" moiety is a linker and is optional, and the "LABEL" moiety is a labeling agent, and all other variables are as described above, for example with reference to structural formula (I). Any of the compounds disclosed with reference to structural formulae (I)-(LXIX) can be used in the labeled conjugate of structural formula (LXX).

In certain embodiments, the -(LINK)$_{0-1}$-(LABEL) moiety is attached the "B" ring system at a benzo, pyrido or pyrazino ring position in the meta position relative to the J moiety. For example, in one embodiment, a labeled conjugate has structural formula (LXXI):

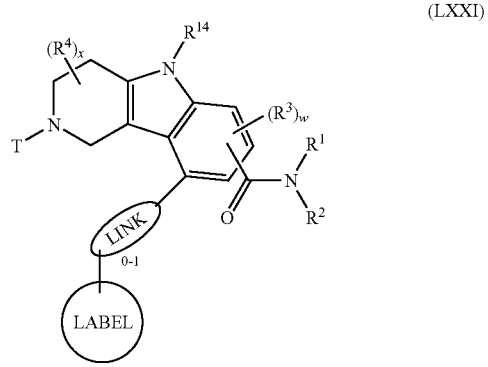

(LXXI)

in which the "LINK" moiety is a linker and is optional, and the "LABEL" moiety is a labeling agent, and all other variables are as described above, for example with reference to any of structural formulae (I), (II), (III), (XII), (XIII), (XXII)-(XXXIII) and (XLII)-(XLIX).

For example, in one particular embodiment, a labeled conjugate has structural formula (LXXII):

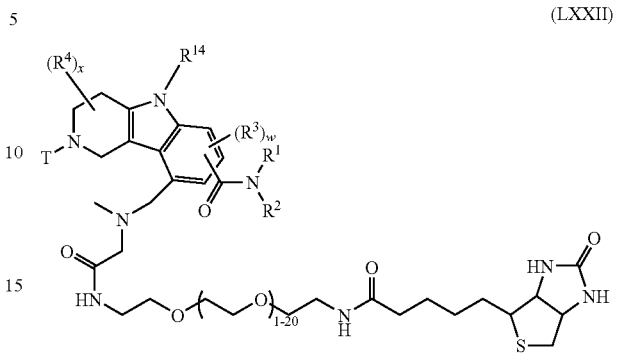

(LXXII)

in which all variables are as described above, for example with reference to any of structural formulae (I), (II), (III), (XII), (XIII), (XXII)-(XXXIII) and (XLII)-(XLIX).

The following examples are intended to further illustrate certain embodiments and are not intended to limit the scope of the invention.

EXAMPLES

Example 1

(a) Synthetic Example 2-benzyl-N-(1-(4-cyanobenzyl)piperidin-4-yl)-2,3,4,5-tetrahydro-1H-pyrido[4,3-b]indole-8-carboxamide (Compound 4)

Compound 4 was prepared as described in Scheme 1, above.

Step 1

A solution of 2-tert-butyl 8-methyl 3,4-dihydro-1H-pyrido[4,3-b]indole-2,8(5H)-dicarboxylate (0.5 g, 1.5 mmol) in dichloromethane/trifluoroacetic acid (1:1, 10 mL) was stirred at room temperature for 1 h. The reaction mixture was then concentrated, diluted with acetic acid (5 mL) and concentrated again to give an oily residue. The residue was dissolved in THF/MeOH (4:1, 10 mL) followed by the addition of benzaldehyde (170 µL, 180 mg, 1.7 mmol), sodium triacetoxyborohydride (485 mg, 2.3 mmol) and acetic acid (175 µL, 185 mg, 3.1 mmol). Additional amounts of benzaldehyde (4×170 µL) and sodium triacetoxyborohydride (4×485 mg) were added over the course of the ensuing 8 h. The resulting reaction mixture was stirred at room temperature overnight then poured over saturated sodium bicarbonate solution (30 mL). The aqueous layer was then extracted with dichloromethane (3×30 mL) and the combined organic layer was washed with water (2×30 mL), dried over MgSO$_4$, filtered and concentrated. Column chromatography (neat dichloromethane→3% MeOH/CH$_2$Cl$_2$) provided methyl 2-benzyl-2,3,4,5-tetrahydro-1H-pyrido[4,3-b]indole-8-carboxylate as a white crystalline solid (320 mg, 66%). $^1$H NMR (CD$_3$OD): δ 8.17 (1H, d, J=1.1 Hz); 7.73 (1H, dd, J=8.7, 1.8 Hz); 7.44-7.27 (6H, m); 3.88 (3H, s); 3.83 (2H, br s); 3.73 (2H, br s) 2.95-2.88 (4H, m). MS (M+H)$^+$=321.

Step 2

To a solution of methyl 2-benzyl-2,3,4,5-tetrahydro-1H-pyrido[4,3-b]indole-8-carboxylate (307 mg, 1.0 mmol) in THF/MeOH/H$_2$O (2:1:1, 12 mL) was added lithium hydroxide monohydrate (240 mg, 5.7 mmol). The reaction mixture was then allowed to stir at room temperature until all the starting material was consumed (2-3 days). The resulting cloudy reaction mixture was then concentrated to give a yellow foamy residue. Trituration with 10% HCl solution provided 2-benzyl-2,3,4,5-tetrahydro-1H-pyrido[4,3-b]indole-8-carboxylic acid as a yellow crystalline solid upon filtration and drying under vacuuo (269 mg, 92%). $^1$H NMR (DMSO-d$_6$): δ 11.59 (1H, s); 10.92 (1H, s); 8.07 (1H, s); 7.71 (1H, d, J=8.5 Hz); 7.65 (2H, d, J=3.6 Hz); 7.49 (3H, d, J=3.6 Hz); 7.39 (1H, d, J=8.5 Hz); 4.58-4.3 (4H, m); 3.78-3.69 (1H, m); 3.52-3.05 (3H, m). MS (M+H)$^+$=307.

Step 3

To a solution of 2-benzyl-2,3,4,5-tetrahydro-1H-pyrido[4,3-b]indole-8-carboxylic acid (50 mg, 0.2 mmol) in DMF (2 mL), HATU (O-(7-azabenzotriazol-1-yl)-N,N,N',N'-tetramethyluronium hexafluorophosphate) (75 mg, 0.2 mmol), 4-amino-1-(4-cyanobenzyl)piperidine dihydrochloride (47 mg, 0.2 mmol) and triethylamine (105 μL, 76 mg, 0.8 mmol) were added. The resulting reaction mixture was stirred at room temperature overnight. The reaction mixture was poured into saturated sodium bicarbonate solution (30 mL) to give a white precipitate which was filtered and dried under vacuuo. The resulting solid was triturated with ethyl ether to yield Compound 4 as a white crystalline solid (80 mg, 97%). $^1$H NMR (DMSO-d$_6$): δ 11.00 (1H, br s); 8.00 (1H, d, J=7.7 Hz); 7.82 (1H, s); 7.78 (2H, d, J=8.3 Hz); 7.53 (1H, d, J=11.8 Hz); 7.50 (2H, d, J=7.7 Hz); 7.39 (2H, d, J=6.6 Hz); 7.36 (2H, d, J=8.3 Hz); 7.32-7.23 (2H, m); 3.76 (3H, br s); 3.58 (4H, d, J=10.5 Hz); 2.89-2.73 (6H, m); 2.06 (2H, t, J=11.0 Hz); 1.76 (2H, d, J=9.9 Hz); 1.58 (2H, q, J=10.7 Hz). MS (M+H)$^+$=504.

(b) Synthetic Example

N-(1-(4-Cyanobenzyl)piperidin-4-yl)-2-(4-(trifluoromethyl)phenylsulfonyl)-2,3,4,5-tetrahydro-1H-pyrido[4,3-b]indole-8-carboxamide (Compound 24)

Compound 24 was prepared according to Scheme 1(b), below:

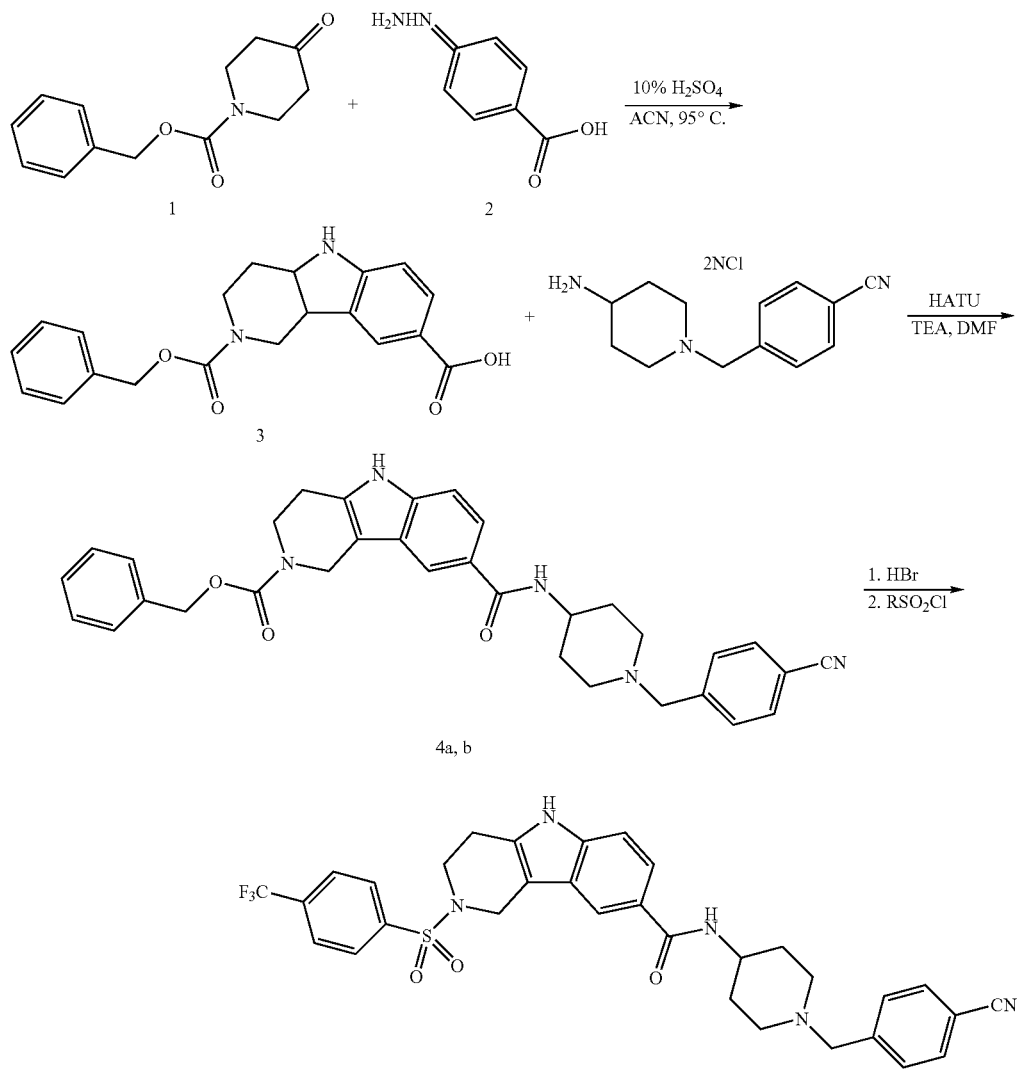

Compound 24

Step 1

A solution of benzyl 4-oxo-1-piperidine carboxylate (1 in Scheme 1(b)), 30.7 g, 131 mmol) and 4-hydrazinobenzoic acid (2, 20 g, 131 mmol) in ACN/10% sulfuric acid (1:1, 400 mL) was allowed to stir at reflux for 19 h. The reaction mixture was then cooled down to room temperature, and the resulting yellow solid was collected by filtration, washed with $H_2O$ (3×50 mL) and dried under vacuum overnight to provide 2-(benzyloxycarbonyl)-2,3,4,5-tetrahydro-1H-pyrido[4,3-b]indole-8-carboxylic acid (3) as a pale yellow solid (35.2 g, 77%). $^1H$ NMR (DMSO-$d_6$, 300 MHZ) 12.33 (br s, 1H), 11.30 (s, 1H), 8.06 (s, 1H), 7.66 (d, J=8.3 Hz, 1H), 7.38-7.32 (m, 6H), 5.14 (s, 2H), 4.72-4.58 (m, 2H), 3.79 (br s, 2H), 2.82 (br s, 2H) ppm; MS (ES) 351 (M+H).

Step 2

To a solution of 2-(benzyloxycarbonyl)-2,3,4,5-tetrahydro-1H-pyrido[4,3-b]indole-8-carboxylic acid (3, 0.5 g, 1.4 mmol) in DMF (10 mL), HATU (0.65 g, 1.7 mmol), 4-amino-1-(4-cyanobenzyl)piperidine dihydrochloride (0.41 g, 1.4 mmol) and triethylamine (1.05 mL, 0.76 g, 7.5 mmol) were added. The resulting reaction mixture was allowed to stir at room temperature overnight, poured into saturated sodium bicarbonate solution (75 mL) and extracted with EtOAc (3×50 mL). The combined organic layers were washed with water (2×30 mL), brine (1×30 mL), dried ($MgSO_4$), filtered and concentrated to give a tan solid. Column chromatography (neat DCM→5% MeOH/DCM) provided benzyl 8-(1-(4-cyanobenzyl)piperidin-4-ylcarbamoyl)-3,4-dihydro-1H-pyrido[4,3-b]indole-2(5H)-carboxylate (4a in Scheme 1(b)) as a white solid upon trituration with ethyl ether (0.55 g, 70%). $^1H$ NMR (DMSO-$d_6$, 300 MHZ) 11.14 (br s, 1H), 8.04 (d, J=8.0 Hz, 1H), 8.00 (s, 1H), 7.79 (d, J=8.0 Hz, 2H), 7.59 (d, J=8.5 Hz, 1H), 7.51 (d, J=7.7 Hz, 2H), 7.39-7.27 (m, 6H), 5.14 (s, 2H), 4.67 (br s, 2H), 3.80 (br s, 3H), 3.57 (s, 2H), 2.82 (br s, 4H), 2.08 (t, J=11.0 Hz, 2H), 1.80 (d, J=11.3 Hz, 2H), 1.61 (q, J=10.7 Hz, 2H) ppm; MS (ES) 548 (M+H).

Step 3

To a solution of benzyl 8-(1-(4-cyanobenzyl)piperidin-4-ylcarbamoyl)-3,4-dihydro-1H-pyrido[4,3-b]indole-2(5H)-carboxylate (4a, 50 mg, 91 μmol) in DCM (dichloromethane) (1.0 mL) was added dropwise a solution of HBr/AcOH (48% w/v, 1.0 mL). After the resulting brown reaction mixture was stirred for 30 min, the volatiles were evaporated, MeOH (2 mL) was added and the volatiles evaporated again. The resulting brown residue was dissolved in DMF (1.0 mL) and triethylamine (0.5 mL, 0.36 g, 3.6 mmol) and 4-(trifluoromethyl)benzenesulfonyl chloride (45 mg, 0.2 mmol) were added. The resulting reaction mixture was allowed to stir at room temperature overnight, then poured into saturated sodium bicarbonate solution (20 mL) to give a brown precipitate which was filtered and purified by reverse phase HPLC to provide Compound 24 upon trituration with ethyl ether (18 mg, 31%). $^1H$ NMR (DMSO-$d_6$, 300 MHZ) 11.21 (br s, 1H), 11.18 (br s, 1H), 9.75 (br s, 1H), 8.26 (d, J=7.2 Hz, 1H), 8.07 (d, J=8.3 Hz, 2H), 7.98 (d, J=7.7 Hz, 4H), 7.71 (d, J=8.3 Hz, 2H), 7.57 (d, J=8.5 Hz, 1H), 7.28 (d, J=8.5 Hz, 1H), 4.40 (d, J=8.3 Hz, 4H), 3.55-3.06 (m, 7H), 2.92-2.82 (m, 2H), 2.07 (d, J=10.5 Hz, 2H), 1.78 (q, J=11.3 Hz, 2H) ppm; MS (ES) 622 (M+H).

The following compounds were prepared using methods analogous to those described in Synthetic Example 1(b) and in Scheme 1(b).

Compound 19: N-(1-benzylpiperidin-4-yl)-2-(4-(trifluoromethyl)phenylsulfonyl)-2,3,4,5-tetrahydro-1H-pyrido[4,3-b]indole-8-carboxamide trifluoroacetate (41%). $^1H$ NMR ($CD_3OD$, 300 MHz) 8.34 (d, J=7.2 Hz, 1H), 8.04 (d, J=8.0 Hz, 2H), 7.93 (br s, 1H), 7.84 (d, J=8.3 Hz, 2H), 7.58 (d, J=8.5 Hz, 1H), 7.52 (s, 5H), 7.29 (d, J=8.3 Hz, 1H), 4.48 (s, 2H), 4.35 (s, 2H), 4.22-4.08 (m, 1H), 3.65-3.56 (m, 4H), 3.21 (t, J=11.6 Hz, 2H), 2.90-2.82 (m, 2H), 2.28 (d, J=13.2 Hz, 2H), 1.90 (q, J=11.6 Hz, 2H) ppm; MS (ES) 597 (M+H).

Compound 25: N-(1-(4-cyanobenzyl)piperidin-4-yl)-2-(4-cyanophenylsulfonyl)-2,3,4,5-tetrahydro-1H-pyrido[4,3-b]indole-8-carboxamide trifluoroacetate (13%). $^1H$ NMR ($CD_3OD$, 300 MHz) 8.01 (d, J=8.5 Hz, 2H), 7.93 (d, J=1.1 Hz, 1H), 7.88 (d, J=8.8 Hz, 2H), 7.71 (d, J=8.3 Hz, 2H), 7.59-7.55 (m, 3H), 7.29 (d, J=8.5 Hz; 1H), 4.49 (s, 2H), 4.00-3.88 (m, 1H), 3.68 (s, 2H), 3.64 (t, J=5.9 Hz, 2H), 2.97 (d, J=11.8 Hz, 2H), 2.85-2.82 (m, 2H), 2.28 (t, J=11.8 Hz, 2H), 1.99 (d, J=9.4 Hz, 2H), 1.75 (q, J=11.8 Hz, 2H) ppm; MS (ES) 579 (M+H).

Compound 26: N-(1-(4-cyanobenzyl)piperidin-4-yl)-2-(pyridin-3-ylsulfonyl)-2,3,4,5-tetrahydro-1H-pyrido[4,3-b]indole-8-carboxamide trifluoroacetate (24%). $^1H$ NMR ($CD_3OD$, 300 MHz) 8.98 (d, J=1.9 Hz, 1H), 8.73 (dd, J=4.7, 1.7 Hz, 1H), 8.36-8.00 (m, 1H), 8.25 (ddd, J=8.3, 2.2, 1.7 Hz, 1H), 7.95 (s, 1H), 7.89 (d, J=8.3 Hz, 2H), 7.71 (d, J=8.6 Hz, 2H), 7.60-7.54 (m, 2H), 7.29 (d, J=8.3 Hz, 1H), 4.52 (br s, 2H), 4.43 (br s, 2H), 4.23-4.10 (m, 1H), 3.67 (t, J=5.8 Hz, 2H), 3.61-3.52 (m, 2H), 3.25-3.15 (m, 2H), 2.90-2.81 (m, 2H), 2.32-2.22 (m, 2H), 1.98-1.81 (m, 2H) ppm; MS (ES) 555 (M+H).

(c) Synthetic Example

N-(1-(4-Cyanophenylsulfonyl)piperidin-4-yl)-2-(4-(trifluoromethyl)benzyl)-2,3,4,5-tetrahydro-1H-pyrido[4,3-b]indole-8-carboxamide (Compound 21)

Compound 21 was prepared according to Scheme 1(c), below:

Scheme 1(c)

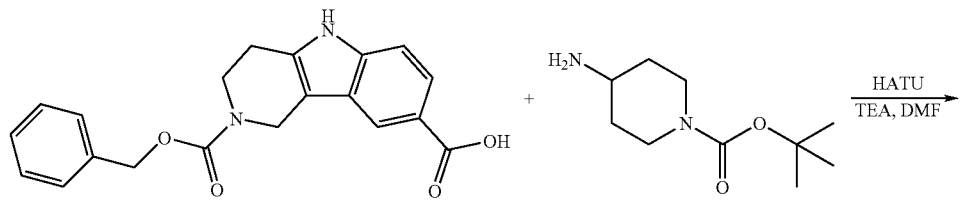

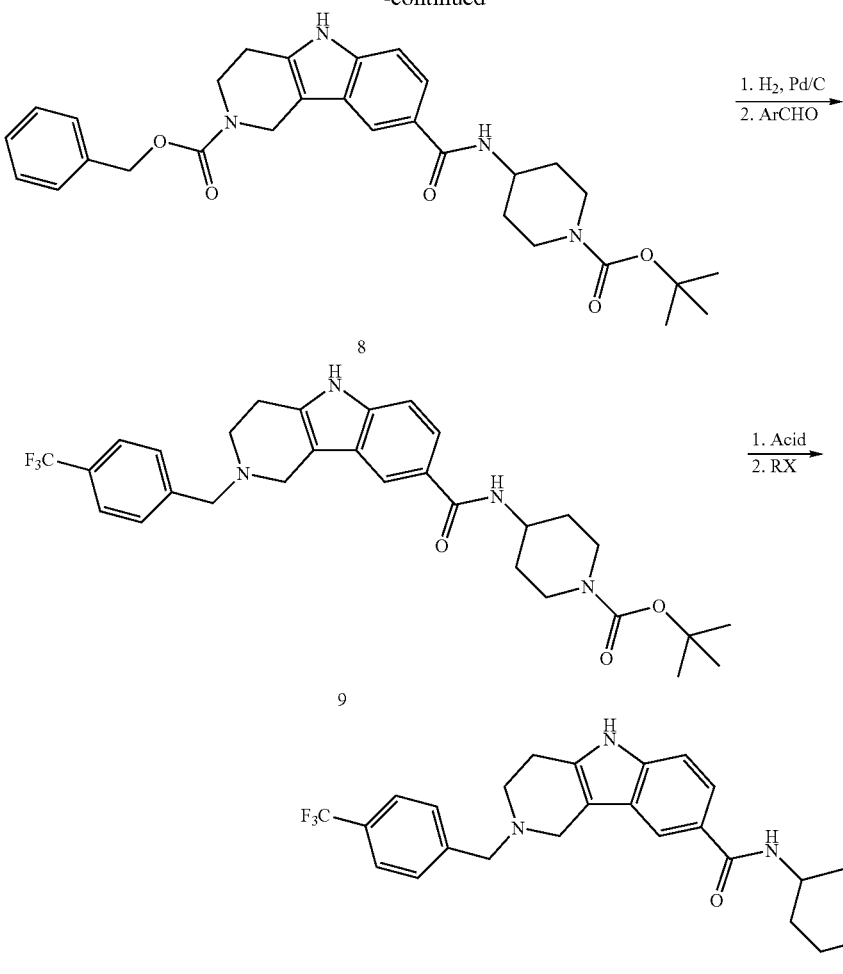

Compound 21: R = —SO₂-Ph-4-CN
Compound 22: R = —SO₂-Ph-4-pyridyl
Compound 23: R = —SO₂-Ph-4-CF₃
Compound 28: R = —SO₂-Ph-4-F
Compound 29: R = —SO₂-Ph-3-CN
Compound 30: R = —SO₂-Ph-3-CF3
Compound 32: R = —SO₂-Ph-4-Cl
Compound 42: R = —CO-3-pyridyl
Compound 50: R = —CH₂-4-pyridyl
Compound 51: R = —CO-4-pyridyl
Compound 52: R = —CH₂-Ph-4-CONH₂
Compound 53: R = —CH₂-4-N-Me-imidazole
Compound 54: R = —CH₂-4-oxazole Step 1

Benzyl 8-(1-(tert-butoxycarbonyl)piperidin-4-ylcarbamoyl)-3,4-dihydro-1H-pyrido[4,3-b]indole-2(5H)-carboxylate (8 in Scheme 1(c)) was prepared as described in step 2 of Synthetic Example 1(b) above as an off-white solid (95%). ¹H NMR (DMSO-d₆, 300 MHZ) 11.15 (s, 1H), 8.05 (d, J=8.0 Hz, 1H), 7.98 (br s, 1H), 7.59 (d, J=8.8 Hz, 1H), 7.38-7.27 (m, 6H), 5.14 (s, 2H), 4.66 (br s, 2H), 4.06-3.88 (m, 3H), 3.80 (br s, 2H), 2.87-2.77 (m, 4H), 1.84-1.72 (m, 2H), 1.52-1.35 (m, 11H) ppm; MS (ES) 533 (M+H).

Step 2 i) A solution of benzyl 8-(1-(tert-butoxycarbonyl)piperidin-4-ylcarbamoyl)-3,4-dihydro-1H-pyrido[4,3-b]indole-2(5H)-carboxylate (8, 20.98 g, 39 mmol) and Pd/C (10% wt.) (4.0 g) in MeOH (300 mL) was allowed to stir at room temperature overnight. The palladium was then filtered, washed with MeOH and the resulting clear solution was concentrated to give tert-butyl 4-(2,3,4,5-tetrahydro-1H-pyrido[4,3-b]indole-8-carboxamido)piperidine-1-carboxylate as a white foamy residue (11.63 g, 74%) ppm; MS (ES) 399 (M+H).

ii) To a solution of tert-butyl 4-(2,3,4,5-tetrahydro-1H-pyrido[4,3-b]indole-8-carboxamido)piperidine-1-carboxylate (11.63 g, 29.2 mmol) and 4-(trifluoromethyl)benzaldehyde (4.8 mL, 6.12 g, 35.1 mmol) in DCM (200 mL), sodium triacetoxyborohydride (12.4 g, 8.5 mmol) was added. The reaction mixture was allowed to stir at room temperature overnight and then poured into saturated sodium bicarbonate solution (300 mL). The layers were separated, and the aqueous layer was extracted with DCM (3×100 mL). The combined organic layers were washed with brine (2×50 mL), dried (MgSO₄), filtered and concentrated to give an off-white solid. Trituration with ethyl ether provided tert-butyl 4-(2-(4-(trifluoromethyl)benzyl)-2,3,4,5-tetrahydro-1H-pyrido[4,3-b]indole-8-carboxamido)piperidine-1-carboxylate (9 in Scheme 1(c)) as a white solid (13.60 g, 84%). ¹H NMR (DMSO-d₆, 300 MHZ) 11.03 (br s, 1H), 8.01 (d, J=7.7 Hz, 1H), 7.83 (s, 1H), 7.71 (d, J=8.3 Hz, 2H), 7.62 (d, J=7.7 Hz, 2H), 7.55 (d, J=8.8 Hz, 1H), 7.26 (d, J=8.5 Hz, 1H), 4.22-3.83 (m, 5H), 3.62 (s, 2H), 2.90-2.77 (br s, 6H), 1.82-1.70 (m, 2H), 1.55-1.30 (m, 11H) ppm; MS (ES) 557 (M+H)

Step 3

To a solution of tert-butyl 4-(2-(4-(trifluoromethyl)benzyl)-2,3,4,5-tetrahydro-1H-pyrido[4,3-b]indole-8-carboxamido)piperidine-1-carboxylate (9, 50 mg, 90 µmol) in DCM (1.0 mL), TFA (1.0 mL) was added. After allowing the reaction mixture to stir at room temperature for 2 h, the volatiles were evaporated, DCM and toluene (10 mL) were added and the volatiles evaporated (2×). The resulting residue was dissolved in DMF (2.0 mL) and triethylamine (0.5 mL, 0.36 g, 3.6 mmol) and 4-cyanobenzenesulfonyl chloride (22 mg, 110 µmol) were added. The resulting reaction mixture was allowed to stir at room temperature overnight, poured into saturated sodium bicarbonate solution (20 mL) to give a tan solid which was triturated with ethyl ether to provide N-(1-(4-cyanophenylsulfonyl)piperidin-4-yl)-2-(4-(trifluoromethyl)benzyl)-2,3,4,5-tetrahydro-1H-pyrido[4,3-b]indole-8-carboxamide (Compound 21, 54 mg, 97%). $^1$H NMR (DMSO-$d_6$, 300 MHZ) 11.04 (br s, 1H), 8.12 (d, J=8.5 Hz, 2H), 8.04 (d, J=7.7 Hz, 1H), 7.92 (d, J=8.3 Hz, 2H), 7.79 (s, 1H), 7.71 (d, J=8.0 Hz, 2H), 7.62 (d, J=7.7 Hz, 2H), 7.51 (d, J=8.5 Hz, 1H), 7.25 (d, J=8.5 Hz, 1H), 3.86 (s, 2H), 3.82-3.72 (m, 1H), 3.70-3.59 (m, 4H), 2.90-2.78 (m, 4H), 2.56-2.44 (m, 2H), 1.90-1.80 (m, 2H), 1.64-1.48 (m, 2H) ppm; MS (ES) 622 (M+H).

The following compounds were prepared using methods analogous to those described in Synthetic Example 1(c) and in Scheme 1(c).

Compound 22: N-(1-(pyridin-3-ylsulfonyl)piperidin-4-yl)-2-(4-(trifluoromethyl)benzyl)-2,3,4,5-tetrahydro-1H-pyrido[4,3-b]indole-8-carboxamide (93%). $^1$H NMR (CD$_3$OD, 300 MHz) 8.94-8.93 (m, 1H), 8.82 (dd, J=4.8, 1.5 Hz, 1H), 8.21 (ddd, J=8.0, 2.3, 1.5 Hz, 1H), 7.83-7.79 (m, 1H), 7.69-7.61 (m, 5H), 7.53 (dd, J=8.5, 1.7 Hz, 1H), 7.28 (d, J=8.5 Hz, 1H), 3.90-3.83 (m, 5H), 3.72 (s, 2H), 2.95-2.93 (m, 4H), 2.56 (t, J=12.0 Hz, 2H), 2.06-1.96 (m, 2H), 1.78-1.62 (m, 2H) ppm; MS (ES) 598 (M+H).

Compound 23: 2-(4-(trifluoromethyl)benzyl)-N-(1-(4-(trifluoromethyl)phenylsulfonyl)piperidin-4-yl)-2,3,4,5-tetrahydro-1H-pyrido[4,3-b]indole-8-carboxamide (97%). $^1$H NMR (DMSO-$d_6$, 300 MHZ) 11.03 (br s, 1H), 8.06 (s, 1H), 8.02 (d, J=8.0 Hz, 2H), 7.96 (d, J=8.3 Hz, 2H), 7.79 (s, 1H), 7.71 (d, J=8.3 Hz, 2H), 7.62 (d, J=8.0 Hz, 2H), 7.51 (d, J=8.5 Hz, 1H), 7.25 (d, J=8.5 Hz, 1H), 3.86 (s, 2H), 3.82-3.74 (m, 1H), 3.67 (d, J=11.6 Hz, 2H), 3.61 (s, 2H), 2.90-2.78 (m, 4H), 2.54-2.47 (m, 2H), 1.92-1.82 (m, 2H), 1.51 (q, J=11.4 Hz, 2H) ppm; MS (ES) 665 (M+H).

Compound 28: N-(1-(4-fluorophenylsulfonyl)piperidin-4-yl)-2-(4-(trifluoromethyl)benzyl)-2,3,4,5-tetrahydro-1H-pyrido[4,3-b]indole-8-carboxamide (10d) (79%). $^1$H NMR (DMSO-$d_6$, 300 MHZ) 11.03 (br s, 1H), 7.83-7.79 (m, 4H), 7.71 (d, J=8.0 Hz, 2H), 7.62 (d, J=8.3 Hz, 2H), 7.53-7.45 (m, 3H), 7.25 (d, J=8.5 Hz, 1H), 3.86 (s, 2H), 3.80-3.70 (m, 1H), 3.68-3.55 (m, 4H), 2.84 (br s, 4H), 2.41 (t, J=10.9 Hz, 2H), 1.90-1.80 (m, 2H), 1.66-1.50 (m, 2H) ppm; MS (ES) 615 (M+H).

Compound 29: N-(1-(3-cyanophenylsulfonyl)piperidin-4-yl)-2-(4-(trifluoromethyl)benzyl)-2,3,4,5-tetrahydro-1H-pyrido[4,3-b]indole-8-carboxamide (81%). $^1$H NMR (DMSO-$d_6$, 300 MHZ) 11.03 (br s, 1H), 8.19 (d, J=8.8 Hz, 2H), 8.07-8.03 (m, 2H), 7.84 (t, J=7.7 Hz, 1H), 7.79 (s, 1H), 7.71 (d, J=8.3 Hz, 2H), 7.62 (d, J=8.3 Hz, 2H), 7.51 (dd, J=8.5, 1.7 Hz, 1H), 7.25 (d, J=8.5 Hz, 1H), 3.86 (s, 2H), 3.82-3.72 (m, 1H), 3.67 (d, J=11.6 Hz, 2H), 3.62 (s, 2H), 2.84 (br s, 4H), 2.53-2.46 (m, 2H), 1.92-1.82 (m, 2H), 1.65-1.50 (m, 2H) ppm; MS (ES) 622 (M+H).

Compound 30: 2-(4-(trifluoromethyl)benzyl)-N-(1-(3-(trifluoromethyl)phenylsulfonyl)piperidin-4-yl)-2,3,4,5-tetrahydro-1H-pyrido[4,3-b]indole-8-carboxamide (75%). $^1$H NMR (DMSO-$d_6$, 300 MHZ) 11.04 (br s, 1H), 8.11 (d, J=7.4 Hz, 1H), 8.06 (dd, J=7.2, 6.1 Hz, 2H), 7.96 (s, 1H), 7.90 (t, J=7.7 Hz, 1H), 7.79 (s, 1H), 7.71 (d, J=8.3 Hz, 2H), 7.62 (d, J=8.0 Hz, 2H), 7.51 (dd, J=8.5, 1.4 Hz, 1H), 7.24 (d, J=8.3 Hz, 1H), 3.86 (s, 2H), 3.82-3.72 (m, 1H), 3.68 (d, J=11.6 Hz, 2H), 3.61 (s, 2H), 2.84 (br s, 4H), 2.51-2.45 (m, 2H), 1.92-1.82 (m, 2H), 1.66-1.52 (m, 2H) ppm; MS (ES) 665 (M+H).

Compound 32: N-(1-(4-chlorophenylsulfonyl)piperidin-4-yl)-2-(4-(trifluoromethyl)benzyl)-2,3,4,5-tetrahydro-1H-pyrido[4,3-b]indole-8-carboxamide trifluoroacetate (59%). $^1$H NMR (DMSO-$d_6$, 300 MHZ) 11.45 (br s, 1H), 10.41 (br s, 1H), 8.12 (d, J=7.4 Hz, 1H), 7.91 (d, J=10.5 Hz, 3H), 7.82 (d, J=6.9 Hz, 2H), 7.76 (d, J=8.8 Hz, 2H), 7.72 (d, J=9.1 Hz, 2H), 7.59 (d, J=8.5 Hz, 1H), 7.35 (d, J=8.5 Hz, 1H), 4.67 (br s, 2H), 4.54-4.32 (m, 2H), 3.77 (br s, 2H), 3.65 (d, J=11.6 Hz, 2H), 3.60-3.50 (m, 1H), 3.13 (br s, 2H), 2.44 (t, J=10.7 Hz, 2H), 1.92-1.81 (m, 2H), 1.66-1.50 (m, 2H) ppm; MS (ES) 631 (M+H).

(d) Synthetic Example

N-(1-nicotinoylpiperidin-4-yl)-2-(4-(trifluoromethyl)benzyl)-2,3,4,5-tetrahydro-1H-pyrido[4,3-b]indole-8-carboxamide (Compound 42)

N-(1-Nicotinoylpiperidin-4-yl)-2-(4-(trifluoromethyl)benzyl)-2,3,4,5-tetrahydro-1H-pyrido[4,3-b]indole-8-carboxamide (compound 42) was prepared as described in step 3 of Synthetic Example 1(c) above (using nicotinyl chloride hydrochloride instead of sulfonyl chlorides) as an off-white solid (87%). $^1$H NMR (DMSO-$d_6$, 300 MHZ) 11.05 (s, 1H), 8.64 (dd, J=5.0, 1.7 Hz, 1H), 8.57 (d, J=1.9 Hz, 1H), 8.07 (d, J=7.7 Hz, 1H), 7.84 (s, 1H), 7.80 (dt, J=8.0, 1.9 Hz, 1H), 7.71 (d, J=8.3 Hz, 2H), 7.62 (d, J=8.0 Hz, 2H), 7.55 (dd, J=8.5, 1.7 Hz, 1H), 7.48 (ddd, J=7.7, 5.0, 0.8 Hz, 1H), 7.26 (d, J=8.5 Hz, 1H), 4.45 (d, J=11.0 Hz, 1H), 4.14-4.00 (m, 1H), 3.86 (s, 2H), 3.62 (s, 2H), 3.60-3.50 (m, 1H), 3.27-3.14 (m, 1H), 3.02-2.78 (m, 5H), 1.97-1.73 (m, 2H), 1.62-1.40 (m, 2H) ppm; MS (ES) 562 (M+H).

(e) Synthetic Example

N-(1-(Pyridin-4-ylmethyl)piperidin-4-yl)-2-(4-(trifluoromethyl)benzyl)-2,3,4,5-tetrahydro-1H-pyrido[4,3-b]indole-8-carboxamide (Compound 50)

Step 1

A solution of tert-butyl 4-(2-(4-(trifluoromethyl)benzyl)-2,3,4,5-tetrahydro-1H-pyrido[4,3-b]indole-8-carboxamido)piperidine-1-carboxylate (9 in Scheme 1(c)), 340 mg, 0.6 mmol) in 4 N HCl/dioxane (10.0 mL) was allowed to stir at room temperature for 2 h. The reaction mixture was then concentrated and the resulting residue was triturated with ethyl ether to give 4-(2-(4-(trifluoromethyl)benzyl)-2,3,4,5-tetrahydro-1H-pyrido[4,3-b]indole-8-carboxamido)piperidine dihydrochloride salt as a white solid (320 mg, 100%).

Step 2

A solution of the dihydrochloride salt of step 1, above (65 mg, 0.12 mmol) was dissolved in DMF (2.0 mL) and 4-(bromomethyl)pyridine hydrobromide (2×35 mg, 2×0.14 mmol) and triethylamine (2×80 μL, 2×58 mg, 2×570 μmol) were added. The resulting reaction mixture was allowed to stir at room temperature overnight, poured into saturated sodium bicarbonate solution (20 mL) to give an off-white solid which was triturated with ethyl ether to provide N-(1-(pyridin-4-ylmethyl)piperidin-4-yl)-2-(4-(trifluoromethyl)benzyl)-2,3,4,5-tetrahydro-1H-pyrido[4,3-b]indole-8-carboxamide (Compound 50, 60%). $^1$H NMR (DMSO-$d_6$, 300 MHZ) 11.02 (s, 1H), 8.49 (d, J=4.7 Hz, 2H), 7.99 (d, J=8.0 Hz, 1H), 7.84 (s, 1H), 7.71 (d, J=8.0 Hz, 2H), 7.62 (d, J=8.3 Hz, 2H), 7.55 (d, J=8.3 Hz, 1H), 7.31 (d, J=4.7 Hz, 2H), 7.25 (d, J=8.3 Hz, 1H), 3.86 (s, 2H), 3.82-3.70 (m, 1H), 3.63 (s, 2H), 3.50 (s, 2H), 2.90-2.74 (m, 6H), 2.06 (t, J=11.1 Hz, 2H), 1.77 (d, J=10.2 Hz, 2H), 1.60 (q, J=10.9 Hz, 2H) ppm; MS (ES) 548 (M+H).

The following compounds were prepared as described in Synthetic Example 1(e) and in Scheme 1(c).

Compound 51: N-(1-isonicotinoylpiperidin-4-yl)-2-(4-(trifluoromethyl)benzyl)-2,3,4,5-tetrahydro-1H-pyrido[4,3-b]indole-8-carboxamide (67%). $^1$H NMR (DMSO-$d_6$, 300 MHZ) 11.04 (s, 1H), 8.66 (d, J=4.7 Hz, 2H), 8.06 (d, J=7.4 Hz, 1H), 7.84 (s, 1H), 7.71 (d, J=8.0 Hz, 2H), 7.62 (d, J=8.3 Hz, 2H), 7.55 (d, J=8.5 Hz, 1H), 7.35 (d, J=4.7 Hz, 2H), 7.26 (d, J=8.5 Hz, 1H), 4.44 (d, J=12.9 Hz, 1H), 4.15-4.00 (m, 1H), 3.87 (s, 2H), 3.63 (s, 2H), 3.46 (d, J=12.9 Hz, 1H), 3.18 (t, J=12.4 Hz, 1H), 2.95 (t, J=12.4 Hz, 1H), 2.85 (br s, 4H), 1.92 (d, J=11.3 Hz, 1H), 1.78 (d, J=11.0 Hz, 1H), 1.57-1.44 (m, 2H) ppm; MS (ES) 562 (M+H).

Compound 52: N-(1-(4-carbamoylbenzyl)piperidin-4-yl)-2-(4-(trifluoromethyl)benzyl)-2,3,4,5-tetrahydro-1H-pyrido[4,3-b]indole-8-carboxamide (66%). $^1$H NMR (DMSO-$d_6$, 300 MHZ) 11.02 (s, 1H), 7.99 (d, J=7.4 Hz, 1H), 7.91 (s, 1H), 7.83 (s, 1H), 7.81 (d, J=8.8 Hz, 2H), 7.71 (d, J=8.0 Hz, 2H), 7.62 (d, J=8.0 Hz, 2H), 7.54 (d, J=8.5 Hz, 1H), 7.35 (d, J=7.7 Hz, 2H), 7.30 (s, 1H), 7.25 (d, J=8.5 Hz, 1H), 3.86 (s, 2H), 3.80-3.68 (m, 1H), 3.63 (s, 2H), 3.51 (s, 2H), 2.90-2.76 (m, 6H), 2.03 (t, J=11.1 Hz, 2H), 1.76 (d, J=10.2 Hz, 2H), 1.58 (q, J=10.6 Hz, 2H) ppm; MS (ES) 590 (M+H).

(f) Synthetic Example

N-(1-((1-methyl-1H-imidazol-4-yl)methyl)piperidin-4-yl)-2-(4-(trifluoromethyl)benzyl)-2,3,4,5-tetrahydro-1H-pyrido[4,3-b]indole-8-carboxamide. (Compound 53)

To a solution of the dihydrochloride salt prepared in step 1 of Synthetic Example 1 (e) (65 mg, 0.12 mmol) was dissolved in DCM (2.0 mL), 1-methyl-1H-imidazole-4-carbaldehyde (2×16 mg, 2×0.15 mmol) and sodium triacetoxyborohydride (2×55 mg, 3×260 μmol) were added. The resulting reaction mixture was allowed to stir at room temperature overnight, and upon reaction completion, was poured into saturated sodium bicarbonate solution (30 mL). The layers were separated, extracted aqueous layer with EtOAc (3×20 mL), washed combined organic layer with brine (2×10 mL), dried (MgSO$_4$), filtered and concentrated. Trituration of the residue with ethyl ether provided N-(1-((1-methyl-1H-imidazol-4-yl)methyl)piperidin-4-yl)-2-(4-(trifluoromethyl)benzyl)-2,3,4,5-tetrahydro-1H-pyrido[4,3-b]indole-8-carboxamide as a white solid (Compound 53, 31 mg, 46%). $^1$H NMR (DMSO-$d_6$, 300 MHZ) 11.02 (s, 1H), 7.98 (d, J=7.4 Hz, 1H), 7.82 (s, 1H), 7.71 (d, J=8.0 Hz, 2H), 7.62 (d, J=7.7 Hz, 2H), 7.54 (d, J=8.5 Hz, 1H), 7.44 (s, 1H), 7.25 (d, J=8.5 Hz, 1H), 6.92 (s, 1H), 3.86 (s, 2H), 3.78-3.66 (m, 1H), 3.63 (s, 2H), 3.60 (s, 3H), 3.30 (s, 2H), 2.92-2.78 (m, 6H), 1.98 (t, J=11.3 Hz, 2H), 1.73 (d, J=11.0 Hz, 2H), 1.52 (q, J=10.8 Hz, 2H) ppm; MS (ES) 551 (M+H).

The following compounds were prepared as described in Synthetic Example 1(f) and in Scheme 1(c).

Compound 54: N-(1-(oxazol-4-ylmethyl)piperidin-4-yl)-2-(4-(trifluoromethyl)benzyl)-2,3,4,5-tetrahydro-1H-pyrido[4,3-b]indole-8-carboxamide (46%). $^1$H NMR (DMSO-$d_6$, 300 MHZ) 11.02 (s, 1H), 8.28 (s, 1H), 7.99 (d, J=8.0 Hz, 1H), 7.95 (s, 1H), 7.82 (s, 1H), 7.70 (d, J=8.3 Hz, 2H), 7.62 (d, J=8.0 Hz, 2H), 7.54 (d, J=8.5 Hz, 1H), 7.25 (d, J=8.5 Hz, 1H), 3.86 (s, 2H), 3.78-3.66 (m, 1H), 3.62 (s, 2H), 3.39 (s, 2H), 2.90-2.76 (m, 6H), 2.04 (t, J=11.0 Hz, 2H), 1.75 (d, J=10.7 Hz, 2H), 1.54 (q, J=10.9 Hz, 2H) ppm; MS (ES) 538 (M+H).

(g) Synthetic Example

N-Carbamoyl Compounds 27, 31, 33

Compound 27 was prepared as shown in Scheme 1(g)

Scheme 1(g)

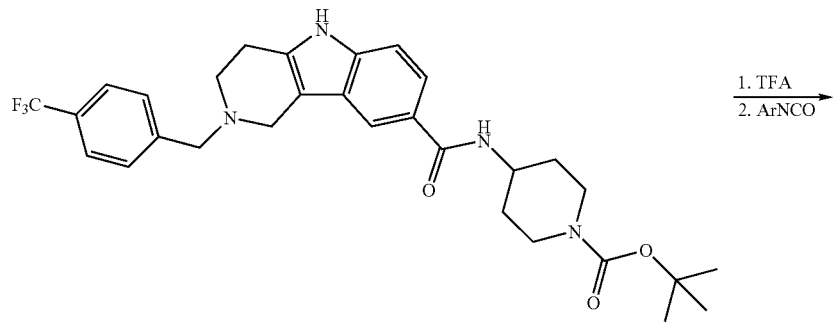

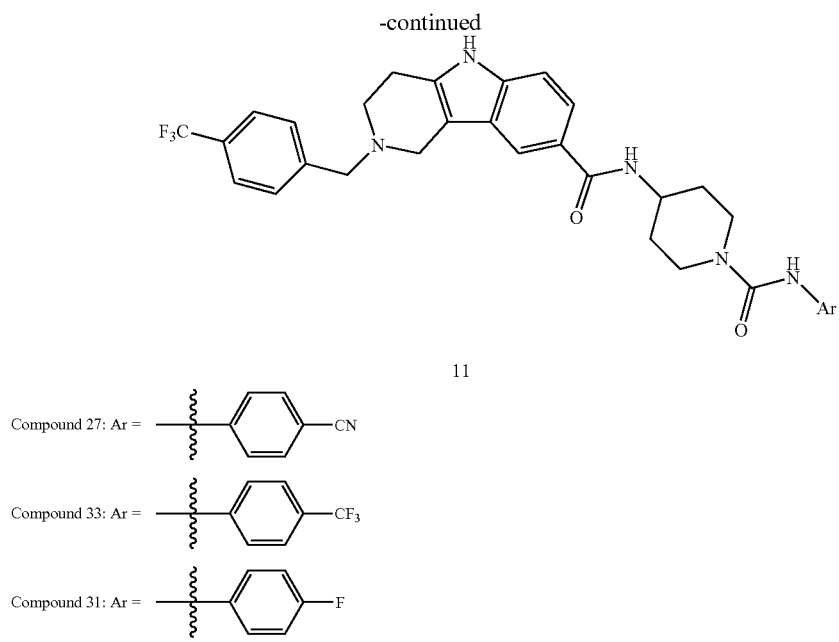

11

Compound 27: Ar = —⟨benzene⟩—CN

Compound 33: Ar = —⟨benzene⟩—CF₃

Compound 31: Ar = —⟨benzene⟩—F

N-(1-(4-cyanophenylcarbamoyl)piperidin-4-yl)-2-(4-(trifluoromethyl)benzyl)-2,3,4,5-tetrahydro-1H-pyrido[4,3-b]indole-8-carboxamide (Compound 27) was prepared as described in step 3 of Synthetic Example 1(c), with purification by column chromatography (5%→10% MeOH/DCM) to yield the title compound as an off-white solid (37%). $^1$H NMR (CD$_3$OD, 300 MHz) 7.85 (d, J=1.4 Hz, 1H), 7.68-7.59 (m, 8H), 7.56 (d, J=1.7 Hz, 1H), 7.30 (d, J=8.5 Hz, 1H), 4.23 (d, J=13.5 Hz, 2H), 4.16-4.08 (m, 1H), 3.90 (s, 2H), 3.73 (s, 2H), 3.07 (t, J=12.0 Hz, 2H), 2.96-2.93 (m, 4H), 2.02 (d, J=10.2 Hz, 2H), 1.67-1.55 (m, 2H) ppm; MS (ES) 601 (M+H).

2-(4-(Trifluoromethyl)benzyl)-N-(1-(4-(trifluoromethyl)phenylcarbamoyl)piperidin-4-yl)-2,3,4,5-tetrahydro-1H-pyrido[4,3-b]indole-8-carboxamide trifluoroacetate (Compound 33) was prepared as described in step 3 of Synthetic Example 1(c) above followed by purification using HPLC as a yellow solid (60%). $^1$H NMR (DMSO-d$_6$, 300 MHZ) 11.46 (s, 1H), 10.46 (br s, 1H), 8.95 (s, 1H), 8.12 (d, J=8.0 Hz, 1H), 7.97 (s, 1H), 7.90 (d, J=7.7 Hz, 2H), 7.81 (d, J=8.0 Hz, 2H), 7.70-7.63 (m, 3H), 7.57 (d, J=8.5 Hz, 2H), 7.36 (d, J=8.5 Hz, 1H), 4.67 (br s, 2H), 4.58-4.33 (m, 2H), 4.15 (d, J=12.7 Hz, 2H), 4.10-3.98 (m, 1H), 3.78 (br s, 2H), 3.14 (br s, 2H), 2.95 (t, J=12.1 Hz, 2H), 1.84 (d, J=10.5 Hz, 2H), 1.56-1.45 (m, 2H) ppm; MS (ES) 644 (M+H).

N-(1-(4-Fluorophenylcarbamoyl)piperidin-4-yl)-2-(4-(trifluoromethyl)benzyl)-2,3,4,5-tetrahydro-1H-pyrido[4,3-b]indole-8-carboxamide was prepared as described in step 3 of Synthetic Example 1(c) above as an off-white solid (96%). $^1$H NMR (DMSO-d$_6$, 300 MHZ) 11.04 (s, 1H), 8.55 (s, 1H), 8.05 (d, J=7.7 Hz, 1H), 7.84 (s, 1H), 7.70 (d, J=8.3 Hz, 2H), 7.61 (d, J=8.0 Hz, 2H), 7.56 (dd, J=8.5, 1.7 Hz, 1H), 7.47-7.43 (m, 2H), 7.26 (d, J=8.5 Hz, 1H), 7.05 (t, J=8.8 Hz, 2H), 4.11 (d, J=13.2 Hz, 2H), 4.06-3.96 (m, 1H), 3.86 (s, 2H), 3.62 (s, 2H), 2.94-2.78 (m, 6H), 1.81 (d, J=11.0 Hz, 2H), 1.54-1.40 (m, 2H) ppm; MS (ES) 594 (M+H).

(h) Synthetic Example

Carboxamide Compounds

Compounds were prepared as shown in Scheme 1(h).

Scheme 1(h)

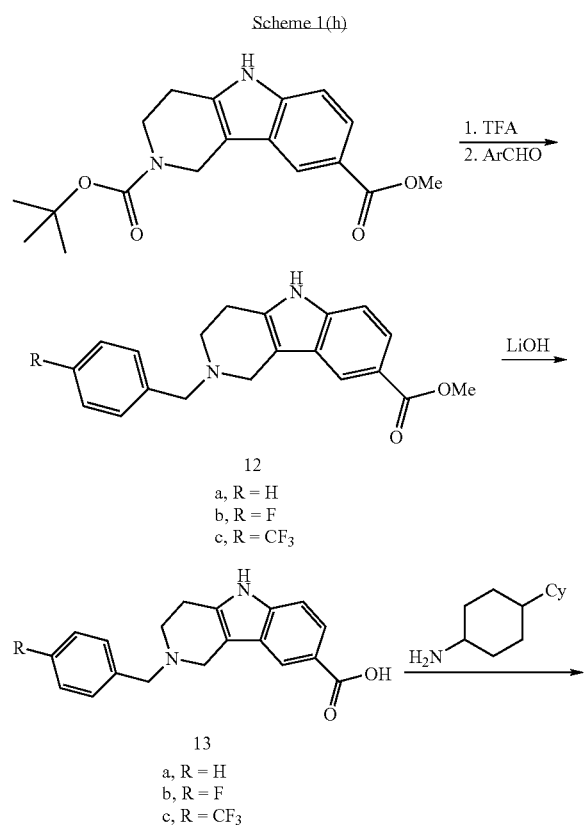

12
a, R = H
b, R = F
c, R = CF$_3$ 13
a, R = H
b, R = F
c, R = CF$_3$

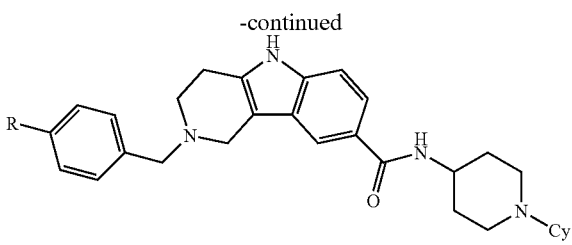

Compound 4: R = H, Cy = 4-cyanobenzyl
Compound 5: R = H, Cy = 4-(trifluoromethyl)benzyl
Compound 7: R = H, Cy = 4-pyridylmethyl
Compound 8: R = F, Cy = 3-pyridylmethyl
Compound 9: R = F, Cy = 4-cyanobenzyl
Compound 10: R = F, Cy = 4-(trifluoromethyl)benzyl
Compound 11: R = CF$_3$, Cy = 3-pyridylmethyl
Compound 12: R = CF$_3$, Cy = 4-cyanobenzyl
Compound 13: R = CF$_3$, Cy = 4-(trifluoromethyl)benzyl
Compound 14: R = CF$_3$, Cy = phenylethyl
Compound 15: R = CF$_3$, Cy = 4-fluorophenyl Step 1

To a solution of 2-tert-butyl 8-methyl 3,4-dihydro-1H-pyrido[4,3-b]indole-2,8(5H)-dicarboxylate (0.50 g, 1.5 mmol) in DCM (5.0 mL), TFA (5.0 mL) was added. After allowing the reaction mixture to stir at room temperature for 1 h, the volatiles were evaporated, DCM and toluene (20 mL) were added and the volatiles evaporated (2×). The resulting residue was dissolved in THF/MeOH (4:1, 10 mL) and benzaldehyde (0.17 mL, 0.18 g, 1.7 mmol) and sodium triacetoxyborohydride (0.485 g, 2.3 mmol) were added. The reaction mixture was allowed to stir at room temperature overnight and 4 more equivalents of the aldehyde and reducing agent were added to cause the reaction to go to completion. The reaction mixture was then poured into saturated sodium bicarbonate solution (300 mL). The layers were separated, and the aqueous layer was extracted with DCM (3×100 mL). The combined organic layers were washed with brine (2×50 mL), dried (MgSO$_4$), filtered and concentrated to give a foamy residue. Column chromatography (DCM→3% MeOH/DCM) provided methyl 2-benzyl-2,3,4,5-tetrahydro-1H-pyrido[4,3-b]indole-8-carboxylate (12a in Scheme 1(h)) as a white solid (0.32 g, 66%). $^1$H NMR (CD$_3$OD, 300 MHz) 8.17 (d, J=1.1 Hz, 1H), 7.73 (dd, J=8.7, 1.8 Hz, 1H), 7.44-7.27 (m, 6H), 3.88 (s, 3H), 3.83 (s, 2H), 3.73 (s, 2H), 2.95-2.88 (m, 4H) ppm; MS (ES) 321 (M+H).

Methyl 2-(4-fluorobenzyl)-2,3,4,5-tetrahydro-1H-pyrido[4,3-b]indole-8-carboxylate (12b in Scheme 1(h)) was prepared in similar fashion as a white solid (51%). $^1$H NMR (CD$_3$OD, 300 MHz) 8.04 (d, J=1.4 Hz, 1H), 7.73 (dd, J=8.5, 1.7 Hz, 1H), 7.46-7.41 (m, 2H), 7.30 (d, J=8.5 Hz, 1H), 7.09 (t, J=8.8 Hz, 2H), 3.88 (s, 3H), 3.81 (s, 2H), 3.72 (s, 2H), 2.90 (br s, 4H) ppm; MS (ES) 339 (M+H).

Methyl 2-(4-(trifluoromethyl)benzyl)-2,3,4,5-tetrahydro-1H-pyrido[4,3-b]indole-8-carboxylate (12c in Scheme 1(h)) was prepared in similar fashion as an off-white solid (0.37 g, 63%). $^1$H NMR (CD$_3$OD, 300 MHz) 8.05 (d, J=1.1 Hz, 1H), 7.73 (dd, J=8.5, 1.7 Hz, 1H), 7.67 (d, J=8.5 Hz, 2H), 7.62 (d, J=8.8 Hz, 2H), 7.30 (d, J=8.5 Hz, 1H), 3.91 (s, 2H), 3.88 (s, 3H), 3.75 (s, 2H), 2.91 (br s, 4H) ppm; MS (ES) 389 (M+H).

Step 2

To a solution of methyl 2-benzyl-2,3,4,5-tetrahydro-1H-pyrido[4,3-b]indole-8-carboxylate (12a, 0.31 g, 1.0 mmol) in THF/MeOH (2:1, 9 mL), a solution of lithium hydroxide hydrate (0.24 g, 5.7 mmol) in water (3.0 mL) was added. After allowing the reaction mixture to stir at room temperature for 2d, the volatiles were evaporated to give a yellow residue. Trituration of the residue with 10% HCl solution provided 2-benzyl-2,3,4,5-tetrahydro-1H-pyrido[4,3-b]indole-8-carboxylic acid (13a in Scheme 1(h)) as a yellow solid (0.27 g, 92%). $^1$H NMR (DMSO-d$_6$, 300 MHZ) 11.59 (s, 1H), 10.92 (s, 1H), 8.07 (s, 1H), 7.71 (d, J=8.5 Hz, 1H), 7.65 (d, J=3.6 Hz, 2H), 7.49 (d, J=3.6 Hz, 3H), 7.39 (d, J=8.5 Hz, 1H), 4.58-4.30 (m, 4H), 3.78-3.69 (m, 1H), 3.52-3.05 (m, 3H) ppm; MS (ES) 307 (M+H).

2-(4-Fluorobenzyl)-2,3,4,5-tetrahydro-1H-pyrido[4,3-b]indole-8-carboxylic acid (13b in Scheme 1(h)) was prepared as a white solid from methyl 2-(4-fluorobenzyl)-2,3,4,5-tetrahydro-1H-pyrido[4,3-b]indole-8-carboxylate (12b) in similar fashion (99%). $^1$H NMR (CD$_3$OD, 300 MHz) 8.16 (s, 1H), 7.84 (dd, J=8.5, 1.7 Hz, 1H), 7.66-7.61 (m, 2H), 7.39 (d, J=8.5 Hz, 1H), 7.28 (t, J=8.67 Hz, 2H), 4.58 (s, 2H), 4.53 (br s, 2H), 3.76 (br s, 2H), 3.24 (t, J=5.8 Hz, 2H) ppm; MS (ES) 325 (M+H).

2-(4-(Trifluoromethyl)benzyl)-2,3,4,5-tetrahydro-1H-pyrido[4,3-b]indole-8-carboxylic acid (13c in Scheme 1(h)) was prepared as an off-white solid from methyl 2-(4-(trifluoromethyl)benzyl)-2,3,4,5-tetrahydro-1H-pyrido[4,3-b]indole-8-carboxylate (12c) in similar fashion (97%). $^1$H NMR (CD$_3$OD, 300 MHz) 8.17 (s, 1H), 7.88-7.79 (m, 5H), 7.39 (d, J=8.5 Hz, 1H), 4.69 (s, 2H), 4.62 (br s, 1H), 4.54 (br s, 1H), 3.90 (br s, 1H), 3.66 (br s, 1H), 3.26 (br s, 2H) ppm; MS (ES) 375 (M+H).

Step 3

2-Benzyl-N-(1-(4-cyanobenzyl)piperidin-4-yl)-2,3,4,5-tetrahydro-1H-pyrido[4,3-b]indole-8-carboxamide (Compound 4) was prepared as an off-white solid from 2-benzyl-2,3,4,5-tetrahydro-1H-pyrido[4,3-b]indole-8-carboxylic acid (13a in Scheme 1(h)) as described in step 2 of Synthetic Example 1(b) above (97%). $^1$H NMR (DMSO-d$_6$, 300 MHZ) 11.00 (s, 1H), 8.00 (d, J=7.7 Hz, 1H), 7.82 (s, 1H), 7.78 (d, J=8.3 Hz, 2H), 7.53 (d, J=11.8 Hz, 1H), 7.50 (d, J=7.7 Hz, 2H), 7.39 (d, J=6.6 Hz, 2H), 7.36 (d, J=8.3 Hz, 2H), 7.32-7.23 (m, 2H), 3.76 (s, 3H), 3.58 (s, 2H), 3.56 (s, 2H), 2.89-2.73 (m, 6H), 2.06 (t, J=11.0 Hz, 2H), 1.76 (d, J=9.9 Hz, 2H), 1.58 (q, J=10.7 Hz, 2H) ppm; MS (ES) 504 (M+H).

2-Benzyl-N-(1-(4-(trifluoromethyl)benzyl)piperidin-4-yl)-2,3,4,5-tetrahydro-1H-pyrido[4,3-b]indole-8-carboxamide (Compound 5) was prepared as an off-white solid from 2-benzyl-2,3,4,5-tetrahydro-1H-pyrido[4,3-b]indole-8-carboxylic acid (13a) as described in step 2 of Synthetic Example 1(b) above (83%). $^1$H NMR (DMSO-d$_6$, 300 MHZ) 11.01 (s, 1H), 8.01 (d, J=7.7 Hz, 1H), 7.82 (s, 1H), 7.68 (d, J=8.0 Hz, 2H), 7.55-7.51 (m, 3H), 7.40-7.32 (m, 3H), 7.28-7.23 (m, 3H), 3.76 (s, 3H), 3.59 (s, 2H), 3.56 (s, 2H), 2.90-2.72 (m, 6H), 2.05 (t, J=11.3 Hz, 2H), 1.77 (d, J=9.9 Hz, 2H), 1.59 (q, J=10.5 Hz, 2H) ppm; MS (ES) 547 (M+H).

2-Benzyl-N-(1-(pyridin-4-ylmethyl)piperidin-4-yl)-2,3,4,5-tetrahydro-1H-pyrido[4,3-b]indole-8-carboxamide (Compound 7) was prepared as a white solid upon HPLC purification from 2-benzyl-2,3,4,5-tetrahydro-1H-pyrido[4,3-b]indole-8-carboxylic acid (13a) as a yellow solid as described in step 2 of Synthetic Example 1(b) above (43%). $^1$H NMR (DMSO-d$_6$, 300 MHZ) 11.49 (s, 1H), 10.39 (br s, 1H), 10.01 (br s, 1H), 8.69 (d, J=5.5 Hz, 2H), 8.30 (d, J=7.7 Hz, 1H), 7.93 (s, 1H), 7.64-7.51 (m, 7H), 7.36 (d, J=8.5 Hz, 1H), 4.60-4.30 (m, 5H), 4.00 (br s, 1H), 3.80-3.25 (m, 5H), 3.14 (br s, 4H), 2.04 (d, J=11.3 Hz, 2H), 1.79 (q, J=11.6 Hz, 2H) ppm; MS (ES) 480 (M+H).

2-(4-Fluorobenzyl)-N-(1-(pyridin-3-ylmethyl)piperidin-4-yl)-2,3,4,5-tetrahydro-1H-pyrido[4,3-b]indole-8-carboxamide (Compound 8) was prepared as an off-white solid from 2-(4-fluorobenzyl)-2,3,4,5-tetrahydro-1H-pyrido[4,3-b]indole-8-carboxylic acid (13b in Scheme 1(h)) as described in step 2 of Synthetic Example 1(b) above (81%). $^1$H NMR (CD$_3$OD, 300 MHz) 8.51 (br s, 1H), 8.44 (dd, J=4.8, 1.5 Hz, 1H), 7.87-7.82 (m, 2H), 7.55 (dd, J=8.4, 1.8 Hz, 1H), 7.46-7.40 (m, 3H), 7.29 (d, J=8.5 Hz, 1H), 7.08 (t, J=8.8 Hz, 2H), 3.96-3.84 (m, 1H), 3.80 (s, 2H), 3.71 (s, 2H), 3.61 (s, 2H), 2.98-2.86 (m, 6H), 2.21 (t, J=11.1 Hz, 2H), 1.95 (d, J=11.3 Hz, 2H), 1.69 (qd, J=11.8, 3.0 Hz, 2H) ppm; MS (ES) 498 (M+H).

N-(1-(4-Cyanobenzyl)piperidin-4-yl)-2-(4-fluorobenzyl)-2,3,4,5-tetrahydro-1H-pyrido[4,3-b]indole-8-carboxamide (Compound 9) was prepared as an off-white solid from 2-(4-fluorobenzyl)-2,3,4,5-tetrahydro-1H-pyrido[4,3-b]indole-8-carboxylic acid (13b) as described in step 2 of Synthetic Example 1(b) above (87%). $^1$H NMR (CD$_3$OD, 300 MHz) 7.84 (d, J=1.4 Hz, 1H), 7.69 (d, J=8.3 Hz, 2H), 7.57-7.53 (m, 3H), 7.47-7.42 (m, 2H), 7.29 (d, J=8.5 Hz, 1H), 7.09 (t, J=8.8 Hz, 2H), 3.96-3.84 (m, 1H), 3.82 (s, 2H), 3.72 (s, 2H), 3.63 (s, 2H), 3.00-2.86 (m, 6H), 2.20 (t, J=11.2 Hz, 2H), 1.94 (d, J=10.2 Hz, 2H), 1.70 (q, J=11.0 Hz, 2H) ppm; MS (ES) 522 (M+H).

2-(4-Fluorobenzyl)-N-(1-(4-(trifluoromethyl)benzyl)piperidin-4-yl)-2,3,4,5-tetrahydro-1H-pyrido[4,3-b]indole-8-carboxamide (Compound 10) as an off-white solid was prepared from 2-(4-fluorobenzyl)-2,3,4,5-tetrahydro-1H-pyrido[4,3-b]indole-8-carboxylic acid (13b) as described in step 2 of Synthetic Example 1(b) above (73%). $^1$H NMR (CD$_3$OD, 300 MHz) 7.84 (d, J=1.1 Hz, 1H), 7.63 (d, J=8.0 Hz, 2H), 7.57-7.53 (m, 3H), 7.44 (dd, J=8.5, 5.5 Hz, 2H), 7.29 (d, J=8.5 Hz, 1H), 7.08 (t, J=8.7 Hz, 2H), 3.96-3.84 (m, 1H), 3.81 (s, 2H), 3.72 (s, 2H), 3.63 (s, 2H), 3.00-2.86 (m, 6H), 2.20 (t, J=10.7 Hz, 2H), 1.94 (d, J=10.7 Hz, 2H), 1.70 (qd, J=11.8, 2.8 Hz, 2H) ppm; MS (ES) 565 (M+H).

N-(1-(Pyridin-3-ylmethyl)piperidin-4-yl)-2-(4-(trifluoromethyl)benzyl)-2,3,4,5-tetrahydro-1H-pyrido[4,3-b]indole-8-carboxamide (Compound 11) was prepared as an off-white solid from 2-(4-(trifluoromethyl)benzyl)-2,3,4,5-tetrahydro-1H-pyrido[4,3-b]indole-8-carboxylic acid (13c in Scheme 1(h)) as described in step 2 of Synthetic Example 1(b) above (66%). $^1$H NMR (CD$_3$OD, 300 MHz) 8.51 (d, J=1.7 Hz, 1H), 8.44 (dd, J=4.8, 1.5 Hz, 1H), 7.86-7.82 (m, 2H), 7.64 (AB q, J=11.7, 8.9 Hz, 4H), 7.55 (dd, J=8.5, 1.9 Hz, 1H), 7.42 (dd, J=7.7, 5.0 Hz, 1H), 7.29 (d, J=8.5 Hz, 1H), 3.96-3.84 (m, 3H), 3.73 (s, 2H), 3.61 (s, 2H), 2.98-2.88 (m, 6H), 2.21 (t, J=11.8 Hz, 2H), 1.94 (d, J=10.7 Hz, 2H), 1.69 (qd, J=11.8, 2.9 Hz, 2H) ppm; MS (ES) 548 (M+H).

N-(1-(4-Cyanobenzyl)piperidin-4-yl)-2-(4-(trifluoromethyl)benzyl)-2,3,4,5-tetrahydro-1H-pyrido[4,3-b]indole-8-carboxamide (Compound 12) was prepared as an off-white solid from 2-(4-(trifluoromethyl)benzyl)-2,3,4,5-tetrahydro-1H-pyrido[4,3-b]indole-8-carboxylic acid (13c) as described in step 2 of Synthetic Example 1(b) above (63%). $^1$H NMR (CD$_3$OD, 300 MHz) 7.84 (d, J=1.4 Hz, 1H), 7.71-7.61 (m, 6H), 7.57-7.53 (m, 3H), 7.44 (d, J=8.5 Hz, 1H), 3.96-3.84 (m, 3H), 3.74 (s, 2H), 3.62 (s, 2H), 3.00-2.86 (m, 6H), 2.20 (t, J=11.4 Hz, 2H), 1.93 (d, J=11.3 Hz, 2H), 1.69 (qd, J=11.8, 3.0 Hz, 2H) ppm; MS (ES) 572 (M+H).

2-(4-(Trifluoromethyl)benzyl)-N-(1-(4-(trifluoromethyl)benzyl)piperidin-4-yl)-2,3,4,5-tetrahydro-1H-pyrido[4,3-b]indole-8-carboxamide (Compound 13) was prepared as an off-white solid from 2-(4-(trifluoromethyl)benzyl)-2,3,4,5-tetrahydro-1H-pyrido[4,3-b]indole-8-carboxylic acid (13c) as described in step 2 of Synthetic Example 1(b) above (55%). $^1$H NMR (CD$_3$OD, 300 MHz) 7.84 (d, J=1.1 Hz, 1H), 7.68-7.61 (m, 6H), 7.57-7.53 (m, 3H), 7.29 (d, J=8.5 Hz, 1H), 3.96-3.84 (m, 3H), 3.73 (s, 2H), 3.63 (s, 2H), 3.00-2.88 (m, 6H), 2.20 (t, J=11.9 Hz, 2H), 1.94 (d, J=12.1 Hz, 2H), 1.70 (qd, J=11.7, 2.8 Hz, 2H) ppm; MS (ES) 615 (M+H).

N-(1-Phenethylpiperidin-4-yl)-2-(4-(trifluoromethyl)benzyl)-2,3,4,5-tetrahydro-1H-pyrido[4,3-b]indole-8-carboxamide (Compound 14) was prepared as an off-white solid from 2-(4-(trifluoromethyl)benzyl)-2,3,4,5-tetrahydro-1H-pyrido[4,3-b]indole-8-carboxylic acid (13c) as described in step 2 of Synthetic Example 1(b) above (41%). $^1$H NMR (CD$_3$OD, 300 MHz) 7.85 (d, J=1.1 Hz, 1H), 7.65 (AB q, J=11.3, 8.8 Hz, 4H), 7.57 (dd, J=8.5, 1.7 Hz, 1H), 7.32-7.17 (m, 6H), 3.98-3.88 (m, 3H), 3.74 (s, 2H), 3.11 (d, J=11.8 Hz, 2H), 3.00-2.90 (m, 4H), 2.87-2.82 (m, 2H), 2.67-2.62 (m, 2H), 2.26 (t, J=11.8 Hz, 2H), 1.99 (d, J=10.5 Hz, 2H), 1.72 (qd, J=11.8, 2.9 Hz, 2H) ppm; MS (ES) 561 (M+H).

N-(1-(4-Fluorophenyl)piperidin-4-yl)-2-(4-(trifluoromethyl)benzyl)-2,3,4,5-tetrahydro-1H-pyrido[4,3-b]indole-8-carboxamide (Compound 15) was prepared as its bistrifluoroacetate salt and purified by reverse phase HPLC as a white solid from 2-(4-(trifluoromethyl)benzyl)-2,3,4,5-tetrahydro-1H-pyrido[4,3-b]indole-8-carboxylic acid (13c) as described in step 2 of Synthetic Example 1(b) above (27%). $^1$H NMR (CD$_3$OD, 300 MHz) 8.16 (s, 1H), 7.95 (s, 1H), 7.88-7.79 (m, 6H), 7.67 (dd, J=8.5, 1.4 Hz, 1H), 7.39 (dd, J=8.7, 2.1 Hz, 2H), 7.25 (dd, J=9.1, 4.4 Hz, 2H), 7.10 (t, J=8.7 Hz, 2H), 4.69 (d, J=2.2 Hz, 3H), 4.57 (br s, 1H), 4.53 (s, 2H), 4.18-4.06 (m, 1H), 3.68 (d, J=12.7 Hz, 2H), 3.28-3.22 (m, 2H), 3.14 (t, J=11.4 Hz, 2H), 2.16 (d, J=10.5 Hz, 2H), 1.93 (qd, J=12.0, 3.1 Hz, 2H) ppm; MS (ES) 551 (M+H).

(i) Synthetic Example

5-Methyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide (Compound 18)

Compound 18 was prepared as shown in Scheme 1(i)

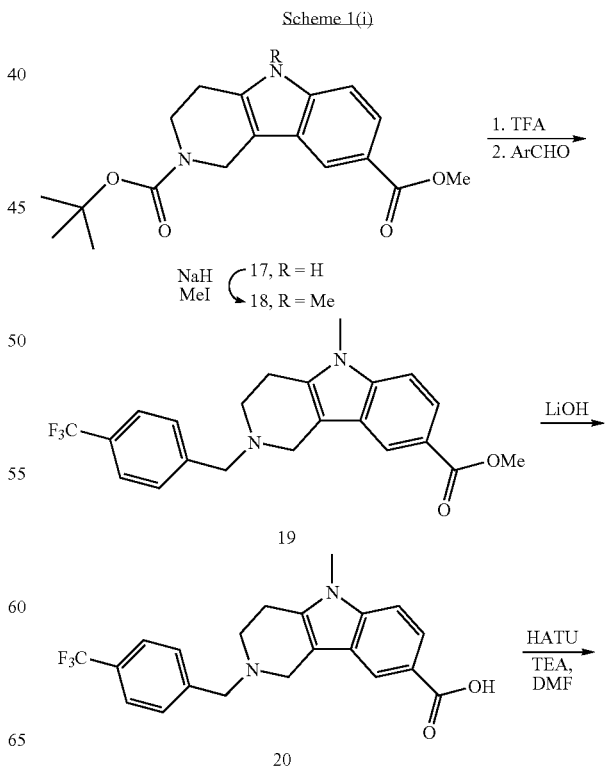

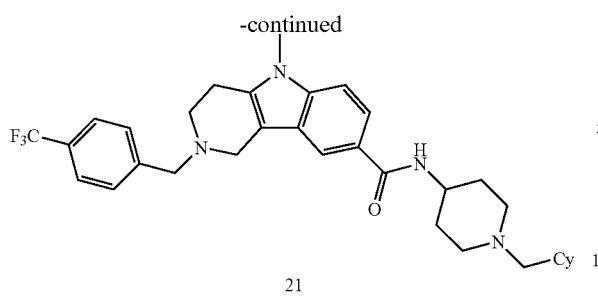

21

Compound 18: Cy = 3-pyridyl-
Compound 16: Cy = 4-NC-Ph-
Compound 17: Cy = 4-F₃C-Ph- Step 1

A solution of 2-tert-butyl 8-methyl 3,4-dihydro-1H-pyrido[4,3-b]indole-2,8(5H)-dicarboxylate (17 in Scheme 1(i), 1.0 g, 3.0 mmol) in DMF (6.0 mL) was added to a cold solution (ice bath) of NaH (60%, 121 mg, 3.0 mmol) in DMF (3 mL). After stirring at 0° C. under $N_2$ atmosphere for 30 min, iodomethane (210 µL, 471 mg, 3.3 mmol) was added dropwise. The reaction mixture was then allowed to warm up to room temperature overnight, cooled down to 0° C. and poured into saturated $NH_4Cl$ solution (20 mL). The resulting brown precipitate was filtered, dried and chromatographed (neat DCM→2% MeOH/DCM) to provide, upon trituration with ethyl ether, 2-tert-butyl 8-methyl 5-methyl-3,4-dihydro-1H-pyrido[4,3-b]indole-2,8(5H)-dicarboxylate (18 in Scheme 1(i), 0.82 g, 79%). $^1$H NMR (CD$_3$OD, 300 MHz) 8.13 (s, 1H), 7.82 (dd, J=8.8, 1.7 Hz, 1H), 7.38 (d, J=8.5 Hz, 1H), 4.64 (br s, 2H), 3.90 (s, 3H), 3.84 (t, J=5.6 Hz, 2H), 3.69 (s, 3H), 2.86 (t, J=5.6 Hz, 2H), 1.52 (s, 9H) ppm; MS (ES) 345 (M+H).

Step 2

To a solution of 2-tert-butyl 8-methyl 5-methyl-3,4-dihydro-1H-pyrido[4,3-b]indole-2,8(5H)-dicarboxylate (18 in Scheme 1(i), 0.30 g, 0.9 mmol) in DCM (3.0 mL), TFA (3.0 mL) was added. After allowing the reaction mixture to stir at room temperature for 0.5 h, the volatiles were evaporated, DCM (20 mL) and cold 1N NaOH solution (20 mL) were added. After 5 min, the organic layer was separated, washed the aqueous layer with DCM (2×20 mL), and the combined organic layer was washed with brine (1×25 mL), dried (MgSO$_4$), filtered and concentrated to give the free amine as a clear oil. Treatment of the free amine with 4-(trifluoromethyl)benzaldehyde (290 µL, 370 mg, 2.1 mmol) and sodium triacetoxyborohydride (340 mg, 1.6 mmol) in DCM (3 mL) at room temperature overnight provided upon pouring the reaction mixture into saturated NaHCO$_3$ solution, separating the organic layer, extracting the aqueous layer with DCM, drying (MgSO$_4$) and concentration a yellow oil. Column chromatography (neat DCM→2% MeOH/DCM) provided methyl 5-methyl-2-(4-(trifluoromethyl)benzyl)-2,3,4,5-tetrahydro-1H-pyrido[4,3-b]indole-8-carboxylate (19 in scheme 1(i)) as a white solid (0.28 g, 78%). $^1$H NMR (CD$_3$OD, 300 MHz) 8.05 (d, J=1.1 Hz, 1H), 7.79 (dd, J=8.8, 1.7 Hz, 1H), 7.64 (AB q, J=14.3, 8.3 Hz, 4H), 7.35 (d, J=8.8 Hz, 1H), 3.89 (s, 2H), 3.88 (s, 3H), 3.74 (s, 2H), 3.67 (s, 3H), 2.95-2.88 (m, 4H) ppm; MS (ES) 403 (M+H).

Step 3

To a solution of methyl 5-methyl-2-(4-(trifluoromethyl)benzyl)-2,3,4,5-tetrahydro-1H-pyrido[4,3-b]indole-8-carboxylate (19 in Scheme 1(i), 0.27 g, 0.7 mmol) in THF/MeOH (2:1, 6 mL), a solution of lithium hydroxide hydrate (0.17 g, 4.1 mmol) in water (2.0 mL) was added. After allowing the reaction mixture to stir at room temperature for 3 d, the volatiles were evaporated to give a yellow residue. Trituration of the residue with 10% HCl solution provided 5-methyl-2-(4-(trifluoromethyl)benzyl)-2,3,4,5-tetrahydro-1H-pyrido[4,3-b]indole-8-carboxylic acid (20 in scheme 1(i)) as an off-white solid (0.21 g, 82%). $^1$H NMR (CD$_3$OD, 300 MHz) 8.17 (d, J=1.1 Hz, 1H), 7.90 (dd, J=8.5, 1.7 Hz, 1H), 7.83 (AB q, J=15.8, 8.4 Hz, 4H), 7.46 (d, J=8.8 Hz, 1H), 4.66 (s, 2H), 4.55 (s, 2H), 3.82-3.78 (m, 2H), 3.76 (s, 3H), 3.26 (t, J=5.9 Hz, 2H) ppm; MS (ES) 389 (M+H).

Step 4

5-Methyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide (Compound 18 of Table 1) was prepared as its bistrifluoroacetate salt and purified by reverse phase HPLC as an off-white solid from 5-methyl-2-(4-(trifluoromethyl)benzyl)-2,3,4,5-tetrahydro-1H-pyrido[4,3-b]indole-8-carboxylic acid as described in step 2 of Synthetic Example 1(b) above (33%). $^1$H NMR (DMSO-d$_6$, 300 MHZ) 10.54 (br s, 1H), 9.79 (br s, 1H), 8.69 (s, 1H), 8.67 (d, J=4.7 Hz, 1H), 8.31 (d, J=7.4 Hz, 1H), 7.96 (d, J=11.6 Hz, 2H), 7.90 (d, J=8.0 Hz, 2H), 7.81 (d, J=8.0 Hz, 2H), 7.69 (d, J=8.3 Hz, 1H), 7.55 (d, J=4.7 Hz, 1H), 7.51 (d, J=8.8 Hz, 1H), 4.70-4.55 (m, 3H), 4.50-4.33 (m, 4H), 4.02 (br s, 1H), 3.86 (br s, 1H), 3.71 (s, 3H), 3.60-3.37 (m, 2H), 3.35-3.05 (m, 4H), 2.05 (d, J=13.2, 2H), 1.77 (q, J=12.2 Hz, 2H) ppm; MS (ES) 562 (M+H).

N-(1-(4-Cyanobenzyl)piperidin-4-yl)-5-methyl-2-(4-(trifluoromethyl)benzyl)-2,3,4,5-tetrahydro-1H-pyrido[4,3-b]indole-8-carboxamide (Compound 16 of Table 1) was prepared as an off-white solid from 5-methyl-2-(4-(trifluoromethyl)benzyl)-2,3,4,5-tetrahydro-1H-pyrido[4,3-b]indole-8-carboxylic acid as described in step 2 of Synthetic Example 1(b) above (70%). $^1$H NMR (CD$_3$OD, 300 MHz) 7.86 (d, J=1.4 Hz, 1H), 7.70-7.60 (m, 7H), 7.54 (d, J=8.3 Hz, 2H), 7.35 (d, J=8.5 Hz, 1H), 3.96-3.84 (m, 3H), 3.74 (s, 2H), 3.68 (s, 3H), 3.62 (s, 2H), 3.20-2.86 (m, 6H), 2.19 (t, J=12.0 Hz, 2H), 1.93 (d, J=11.8 Hz, 2H), 1.69 (qd, J=12.0, 3.2 Hz, 2H) ppm; MS (ES) 586 (M+H).

5-Methyl-2-(4-(trifluoromethyl)benzyl)-N-(1-(4-(trifluoromethyl)benzyl)piperidin-4-yl)-2,3,4,5-tetrahydro-1H-pyrido[4,3-b]indole-8-carboxamide (Compound 17 of Table 1) was prepared as an off-white solid from 5-methyl-2-(4-(trifluoromethyl)benzyl)-2,3,4,5-tetrahydro-1H-pyrido[4,3-b]indole-8-carboxylic acid as described in step 2 of Synthetic Example 1(b) above (68%). $^1$H NMR (CD$_3$OD, 300 MHz) 7.86 (d, J=1.4 Hz, 1H), 7.68-7.61 (m, 7H), 7.54 (d, J=8.0 Hz, 2H), 7.35 (d, J=8.5 Hz, 1H), 3.96-3.84 (m, 3H), 3.74 (s, 2H), 3.68 (s, 3H), 3.63 (s, 2H), 3.20-2.88 (m, 6H), 2.19 (t, J=11.0 Hz, 2H), 1.94 (d, J=12.4 Hz, 2H), 1.70 (qd, J=12.1, 3.3 Hz, 2H) ppm; MS (ES) 629 (M+H).

(i) Synthetic Example

5-Acetyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide Bistrifluoroacetate (Compound 20)

Compound 20 was prepared as shown in Scheme 1(j).

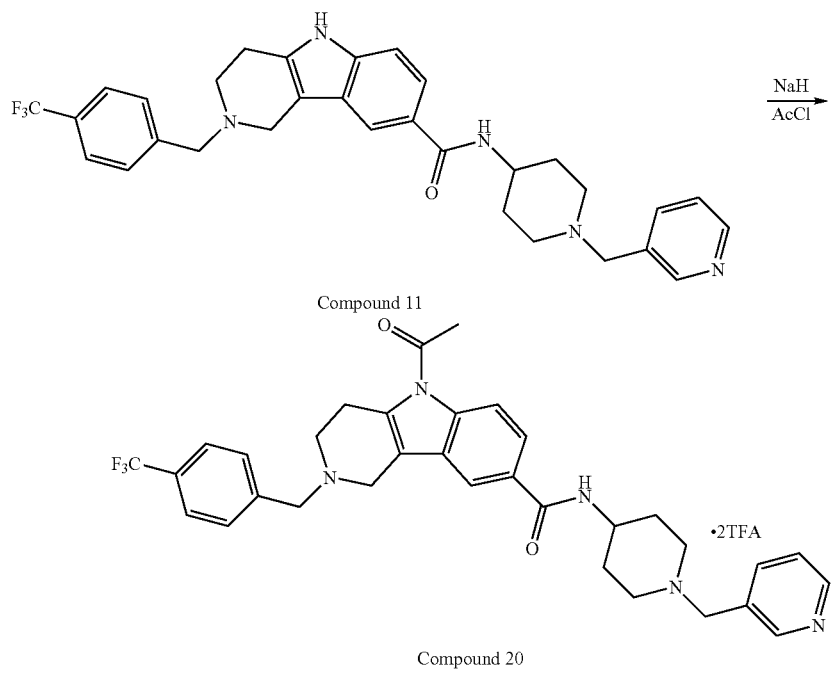

To a solution of N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide (Compound 11, 50 mg, 0.09 mmol) in DMF (1.0 mL), NaH (60%, 5 mg, 0.13 mmol) was added at room temperature. The resulting brown reaction mixture was allowed to stir for 20 min, cooled down to −25° C. and acetyl chloride (7 μL, 7.7 mg, 0.1 mmol) was added. The reaction mixture was then allowed to warm up to room temperature over 1 h and poured over ice-cold saturated NaHCO₃ solution to give a brown precipitate which was collected and purified by reverse phase HPLC. The purified material was triturated with ethyl ether to provide 5-acetyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide (Compound 20) as its bistrifluoroacetate salt as a white solid (31%). $^1$H NMR (CD$_3$OD, 300 MHz) 8.73 (d, J=1.7 Hz, 1H), 8.70 (dd, J=5.1, 1.5 Hz, 1H), 8.14 (d, J=8.8 Hz, 1H), 8.07 (dt, J=7.4, 1.7 Hz, 1H), 7.97 (s, 1H), 7.87-7.79 (m, 5H), 7.61 (dd, J=8.0, 5.0 Hz, 1H), 4.69 (s, 2H), 4.53 (s, 2H), 4.45 (s, 2H), 4.26-4.14 (m, 1H), 3.77 (br s, 2H), 3.64-3.52 (m, 4H), 3.28-3.20 (m, 2H), 2.80 (s, 3H), 2.26 (d, J=14.4 Hz, 2H), 1.99 (br s, 2H) ppm; MS (ES) 590 (M+H).

(k) Synthetic Example 2-(4-Fluorophenyl)-N-(1-(pyridin-3-ylmethyl)piperidin-4-yl)-2,3,4,5-tetrahydro-1H-pyrido[4,3-b]indole-8-carboxamide (Compound 36)

Compound 36 was prepared as shown in Scheme 1(k).

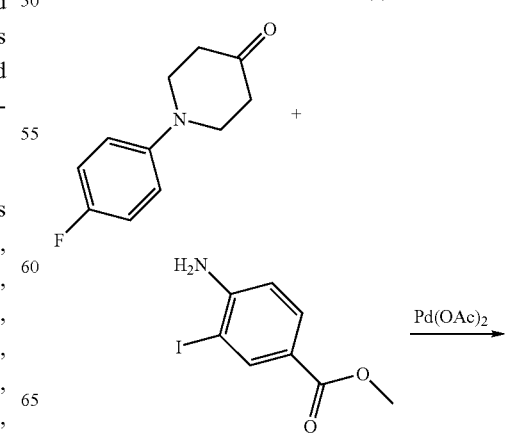

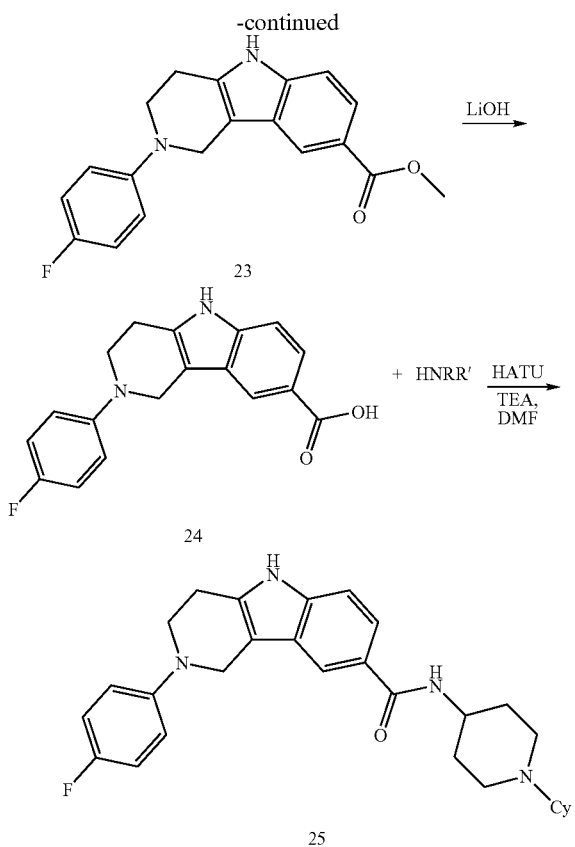

Compound 36: Cy = 3-pyridylmethyl
Compound 34: Cy = 4-cyanobenzyl
Compound 37: Cy = 4-(trifluoromethyl)benzyl
Compound 35: Cy = 4-fluorophenylsulfonyl Step 1

A solution of methyl 4-amino-3-iodobenzoate (0.5 g, 1.8 mmol), 1-(4-fluorophenyl)piperidin-4-one (1.05 g, 5.4 mmol), 1,4-diazabicyclo[2.2.2]octane (0.61 g, 5.4 mmol) and palladium (II) acetate (20 mg, 0.09 mmol) in DMF (10.0 mL) was degassed, filled with argon (3×) and allowed to stir at 110° C. for 3.5 h. The reaction mixture was allowed to cool to room temperature and partitioned between EtOAc (40 mL) and water (40 mL), and the aqueous layer was extracted with EtOAc (2×20 mL). The combined organic layers were washed with water (2×20 mL), brine (1×20 mL), dried (MgSO$_4$), filtered and concentrated. Column chromatography (25% EtOAc/hexane) provided, upon trituration with ethyl ether, methyl 2-(4-fluorophenyl)-2,3,4,5-tetrahydro-1H-pyrido[4,3-b]indole-8-carboxylate (23 in Scheme 1(k)) as a yellow solid (0.23 g, 39%). $^1$H NMR (CDCl$_3$, 300 MHZ) 8.17 (s, 1H), 7.77 (d, J=7.2 Hz, 1H), 7.23 (d, J=8.0 Hz, 3H), 7.09 (t, J=8.1 Hz, 2H), 4.53 (s, 2H), 3.96 (s, 3H), 3.73 (t, J=5.6 Hz, 2H), 3.12 (br s, 2H) ppm; MS (ES) 325 (M+H).

Step 2

To a solution of methyl 2-(4-fluorophenyl)-2,3,4,5-tetrahydro-1H-pyrido[4,3-b]indole-8-carboxylate (23, 0.22 g, 0.7 mmol) in THF/MeOH (2:1, 3.0 mL), a solution of lithium hydroxide hydrate (3×0.17 g, 3×4.0 mmol) in water (1.0 mL) was added. After allowing the reaction mixture to stir at room temperature until the starting material is consumed, the volatiles were evaporated to give a yellow residue. Trituration of the residue with 10% HCl solution provided 2-(4-fluorophenyl)-2,3,4,5-tetrahydro-1H-pyrido[4,3-b]indole-8-carboxylic acid (24 in Scheme 1(k)) as a yellow solid (0.21 g, 98%). $^1$H NMR (DMSO-d$_6$, 300 MHZ) 11.41 (s, 1H), 8.16 (s, 1H), 7.69 (dd, J=8.4, 1.5 Hz, 1H), 7.44 (br s, 2H), 7.37 (d, J=8.5, 1H), 7.23 (t, J=8.0 Hz, 2H), 4.59 (s, 2H), 3.80 (s, 2H), 3.06 (s, 2H) ppm; MS (ES) 311 (M+H).

Step 3

To a solution of 2-(4-fluorophenyl)-2,3,4,5-tetrahydro-1H-pyrido[4,3-b]indole-8-carboxylic acid (24, 50 mg, 0.16 mmol) in DMF (2.0 mL), HATU (75 mg, 0.2 mmol), 1-(pyridin-3-ylmethyl)piperidin-4-amine dihydrochloride (48 mg, 0.16 mmol) and triethylamine (150 μL, 110 mg, 1.1 mmol) were added. The resulting reaction mixture was allowed to stir at room temperature overnight, poured into saturated sodium bicarbonate solution (10 mL) to give a precipitate, filtered and dried under vacuum overnight. Trituration with ethyl ether provided 2-(4-fluorophenyl)-N-(1-(pyridin-3-ylmethyl)piperidin-4-yl)-2,3,4,5-tetrahydro-1H-pyrido[4,3-b]indole-8-carboxamide (Compound 36) as a pale yellow solid (57 mg, 73%). $^1$H NMR (DMSO-d$_6$, 300 MHZ) 11.08 (s, 1H), 8.49 (d, J=1.4 Hz, 1H), 8.45 (dd, J=4.8, 1.5 Hz, 1H), 8.03 (d, J=8.0 Hz, 1H), 8.02 (s, 1H), 7.70 (dt, J=7.7, 1.8 Hz, 1H), 7.56 (dd, J=8.4, 1.5 Hz, 1H), 7.35 (dd, J=7.7, 4.7 Hz, 1H), 7.28 (d, J=8.3 Hz, 1H), 7.06 (d, J=5.0 Hz, 2H), 7.05 (d, J=3.3 Hz, 2H), 4.37 (s, 2H), 3.87-3.72 (m, 1H), 3.63 (t, J=5.2 Hz, 2H), 3.52 (s, 2H), 2.92-2.78 (m, 4H), 2.12-2.00 (m, 2H), 1.80 (d, J=10.5 Hz, 2H), 1.61 (qd, J=11.7, 3.0 Hz, 2H) ppm; MS (ES) 484 (M+H).

N-(1-(4-Cyanobenzyl)piperidin-4-yl)-2-(4-fluorophenyl)-2,3,4,5-tetrahydro-1H-pyrido[4,3-b]indole-8-carboxamide (Compound 34) was prepared as a pale yellow solid as described in step 3 of synthetic example 1(k) above (73%). $^1$H NMR (DMSO-d$_6$, 300 MHZ) 11.07 (s, 1H), 8.02 (s, 2H), 7.79 (d, J=8.0 Hz, 2H), 7.57 (d, J=8.5 Hz, 1H), 7.51 (d, J=8.0 Hz, 2H), 7.28 (d, J=8.5 Hz, 1H), 7.07 (s, 2H), 7.05 (d, J=3.3 Hz, 2H), 4.38 (s, 2H), 3.88-3.72 (m, 1H), 3.63 (t, J=5.5 Hz, 2H), 3.58 (s, 2H), 2.89 (br s, 2H), 2.82 (d, J=11.3 Hz, 2H), 2.09 (t, J=10.7 Hz, 2H), 1.81 (d, J=12.3 Hz, 2H), 1.63 (q, J=10.0 Hz, 2H) ppm; MS (ES) 508 (M+H).

2-(4-Fluorophenyl)-N-(1-(4-(trifluoromethyl)benzyl)piperidin-4-yl)-2,3,4,5-tetrahydro-1H-pyrido[4,3-b]indole-8-carboxamide (Compound 37) was prepared as a pale yellow solid as described in step 3 of Synthetic Example 1(k) (36%). $^1$H NMR (DMSO-d$_6$, 300 MHZ) 11.08 (s, 1H), 8.04 (d, J=8.0 Hz, 1H), 8.03 (s, 1H), 7.69 (d, J=8.3 Hz, 2H), 7.58 (d, J=1.7 Hz, 1H), 7.54 (d, J=8.8 Hz, 2H), 7.28 (d, J=8.5 Hz, 1H), 7.07 (s, 2H), 7.05 (d, J=3.3 Hz, 2H), 4.37 (s, 2H), 3.88-3.74 (m, 1H), 3.63 (t, J=5.2 Hz, 2H), 3.57 (s, 2H), 2.92-2.78 (m, 4H), 2.08 (t, J=10.9, 2H), 1.80 (d, J=10.7 Hz, 2H), 1.62 (q, J=11.4 Hz, 2H) ppm; MS (ES) 551 (M+H).

2-(4-Fluorophenyl)-N-(1-(4-fluorophenylsulfonyl)piperidin-4-yl)-2,3,4,5-tetrahydro-1H-pyrido[4,3-b]indole-8-carboxamide (Compound 35) was prepared as an off-white solid as described in step 3 of Synthetic Example 1(k) (75%). $^1$H NMR (DMSO-d$_6$, 300 MHZ) 11.09 (s, 1H), 8.09 (d, J=7.4 Hz, 1H), 7.99 (s, 1H), 7.82 (dd, J=8.7, 5.4 Hz, 2H), 7.51 (q, J=8.7 Hz, 3H), 7.27 (d, J=8.5 Hz, 1H), 7.07 (s, 2H), 7.05 (d, J=1.9 Hz, 2H), 4.37 (s, 2H), 3.86-3.72 (m, 1H), 3.70-3.58 (m, 4H), 2.88 (br s, 2H), 2.44 (t, J=10.2 Hz, 2H), 1.90 (d, J=9.9 Hz, 2H), 1.63 (q, J=11.3 Hz, 2H) ppm; MS (ES) 551 (M+H).

(1) Synthetic Example

N-(1-(4-Fluorobenzoyl)piperidin-4-yl)-2-(4-fluorophenyl)-2,3,4,5-tetrahydro-1H-pyrido[4,3-b]indole-8-carboxamide (Compound 39)

Compound 39 was prepared as described in Scheme 1(I).

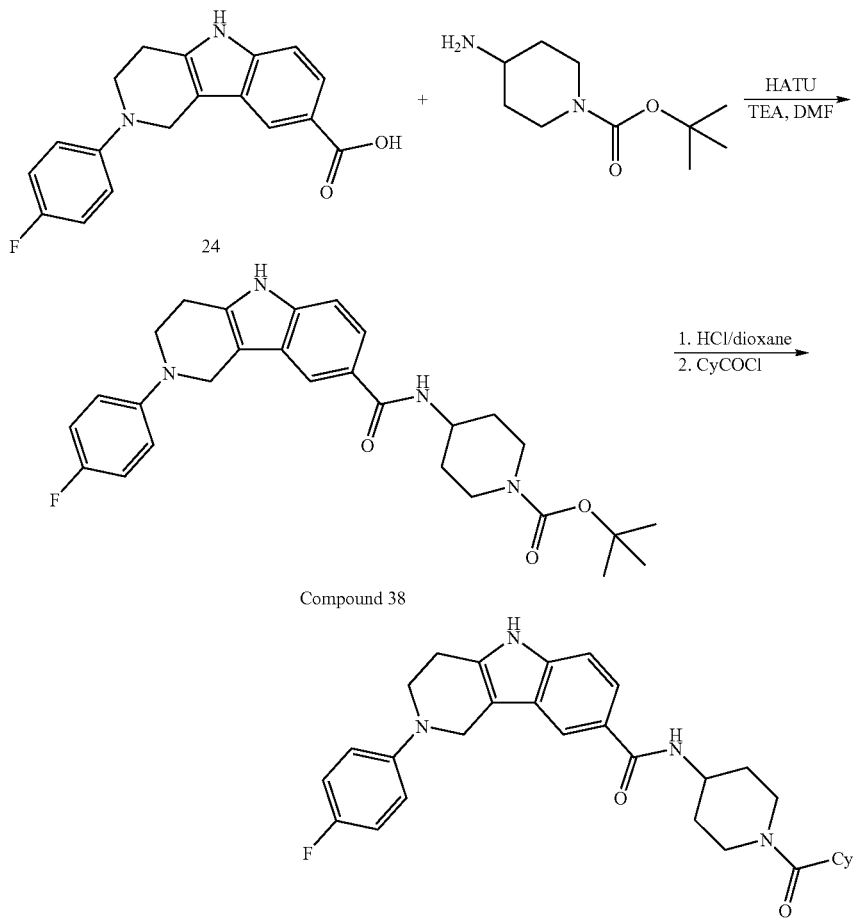

Compound 39: Cy = 4-fluorophenyl
Compound xx: Cy = 3-pyridyl
Compound xx: Cy = 4-(trifluoromethyl)phenyl Step 1 tert-Butyl 4-(2-(4-Fluorophenyl)-2,3,4,5-tetrahydro-1H-pyrido[4,3-b]indole-8-carboxamido)piperidine-1-carboxylate (Compound 38) was prepared as an off-white solid as described in step 3 of Synthetic Example 1(k) above (1.42 g, 98%). $^1$H NMR (DMSO-$d_6$, 300 MHZ) 11.08 (s, 1H), 8.05 (d, J=7.7 Hz, 1H), 8.02 (s, 1H), 7.57 (dd, J=8.4, 1.8 Hz, 1H), 7.25 (d, J=8.5 Hz, 1H), 7.07 (s, 2H), 7.05 (d, J=3.6 Hz, 2H), 4.38 (s, 2H), 4.00-3.90 (m, 3H), 3.63 (br s, 2H), 2.92-2.84 (m, 4H), 1.80 (d, J=11.8 Hz, 2H), 1.52-1.44 (m, 2H), 1.42 (s, 9H) ppm; MS (ES) 515 (M+Na).

Step 2

A solution of tert-butyl 4-(2-(4-fluorophenyl)-2,3,4,5-tetrahydro-1H-pyrido[4,3-b]indole-8-carboxamido)piperidine-1-carboxylate (Compound 38, 50 mg, 100 μmol) in 4 N HCl/dioxane (3.0 mL) was allowed to stir at room temperature for 2 h. The reaction mixture was then concentrated, MeOH (5.0 mL) was added and the volatiles were evaporated (2x). The resulting residue was dissolved in DMF (2.0 mL) and 4-fluorobenzoyl chloride (15 μL, 20 mg, 130 μmol) and triethylamine (0.5 mL, 0.36 g, 3.6 mmol) were added. The resulting reaction mixture was allowed to stir at room temperature overnight, poured into saturated sodium bicarbonate solution (20 mL) to give a yellow solid which was triturated with ethyl ether and then purified by reverse phase HPLC to provide N-(1-(4-fluorobenzoyl)piperidin-4-yl)-2-(4-fluorophenyl)-2,3,4,5-tetrahydro-1H-pyrido[4,3-b]indole-8-carboxamide (Compound 39) (46%). $^1$H NMR (DMSO-$d_6$, 300 MHZ) 11.13 (s, 1H), 8.09 (d, J=7.7 Hz, 1H), 8.03 (s, 1H), 7.58 (dd, J=8.4, 1.5 Hz, 1H), 7.45 (dd, J=8.5, 5.5 Hz, 2H), 7.28 (t, J=8.8 Hz, 3H), 7.10 (m, 4H), 4.43 (s, 3H), 4.18-4.03 (m, 2H), 3.70-3.54 (m, 3H), 3.16 (br s, 1H), 2.92 (br s, 2H), 1.87 (br s, 2H), 1.54 (br s, 2H) ppm; MS (ES) 515 (M+H).

2-(4-Fluorophenyl)-N-(1-nicotinoylpiperidin-4-yl)-2,3,4,5-tetrahydro-1H-pyrido[4,3-b]indole-8-carboxamide (Compound 40) was prepared as a yellow solid as described in step 2 of Synthetic Example 1(l) above (22%). $^1$H NMR (DMSO-$d_6$, 300 MHZ) 11.15 (s, 1H), 8.69 (d, J=5.0 Hz, 1H), 8.65 (s, 1H), 8.12 (d, J=7.7 Hz, 1H), 8.04 (s, 1H), 7.92 (d, J=8.0 Hz, 1H), 7.58 (d, J=8.0 Hz, 1H), 7.56 (d, J=5.2 Hz, 1H), 7.30 (d, J=8.5 Hz, 1H), 7.16-7.08 (m, 4H), 4.60-4.40 (m, 3H), 4.11 (br s, 1H), 3.69 (br s, 2H), 3.63-3.51 (m, 1H), 3.30-3.18 (br s, 1H), 3.06-2.88 (m, 3H), 2.00-1.77 (m, 2H), 1.69-1.42 (m, 2H) ppm; MS (ES) 498 (M+H).

2-(4-Fluorophenyl)-N-(1-(4-(trifluoromethyl)benzoyl)piperidin-4-yl)-2,3,4,5-tetrahydro-1H-pyrido[4,3-b]indole-8-carboxamide (Compound 41) was prepared as a yellow solid as described in step 2 of Synthetic Example 1(1) (35%). $^1$H NMR (DMSO-d$_6$, 300 MHZ) 11.14 (s, 1H), 8.12 (d, J=7.7 Hz, 1H), 8.03 (s, 1H), 7.83 (d, J=8.3 Hz, 2H), 7.61-7.57 (m, 3H), 7.30 (d, J=8.5 Hz, 1H), 7.13-7.06 (m, 4H), 4.52-4.43 (m, 1H), 4.42 (s, 2H), 4.20-4.04 (m, 1H), 3.67 (br s, 2H), 3.52 (d, J=12.1 Hz, 1H), 3.21 (t, J=12.1 Hz, 1H), 2.92 (br s, 2H), 2.00-1.75 (m, 2H), 1.69-1.41 (m, 2H) ppm; MS (ES) 565 (M+H).

(m) Synthetic Example 2-(4-Carbamoylbenzyl)-N-(1-(4-cyanobenzyl)piperidin-4-yl)-2,3,4,5-tetrahydro-1H-pyrido[4,3-b]indole-8-carboxamide (Compound 44)

Compound 44 was prepared as shown in Scheme 1(m).

Scheme 1(m)

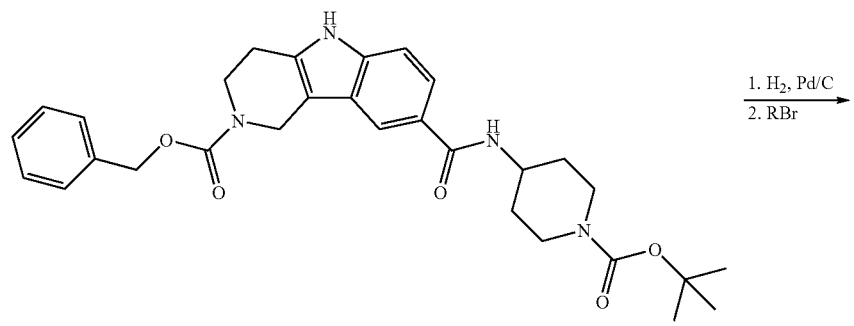

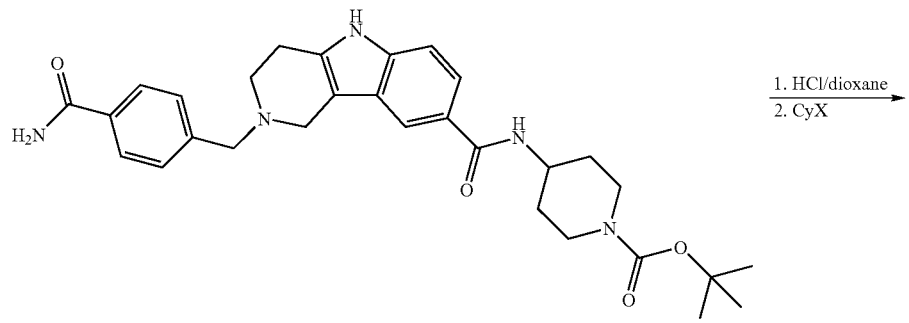

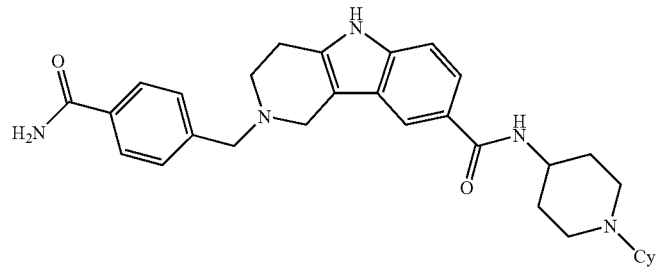

Compound 44: Cy = 4-NC-Ph-CH$_2$—
Compound 45: Cy = 4-pyridyl-CH$_2$—
Compound 46: Cy = 4-pyridyl-CO—
Compound 47: Cy = 4-CF$_3$-Ph-CH$_2$—
Compound 48: Cy = 4-F-Ph-CH$_2$—
Compound 49: Cy = 4-H$_2$NCO-Ph-CH$_2$—

Step 1 i) A solution of benzyl 8-(1-(tert-butoxycarbonyl)piperidin-4-ylcarbamoyl)-3,4-dihydro-1H-pyrido[4,3-b]indole-2(5H)-carboxylate (8 in Scheme 1(m), 1.0 g, 1.9 mmol) and Pd/C (10% wt., 0.2 g) in MeOH (20 mL) was allowed to stir at room temperature overnight. The palladium was then removed by filtration and washed with MeOH; and the resulting clear solution was concentrated to give tert-butyl 4-(2,3,4,5-tetrahydro-1H-pyrido[4,3-b]indole-8-carboxamido)piperidine-1-carboxylate as an-off white solid (0.745 g, 100%). MS (ES) 399 (M+H).

ii) To a solution of tert-butyl 4-(2,3,4,5-tetrahydro-1H-pyrido[4,3-b]indole-8-carboxamido)piperidine-1-carboxylate (0.745 g, 1.9 mmol) in DMF (10 mL), 4-bromomethylbenzamide (0.44 g, 2.1 mmol) and TEA (1.2 mL, 0.857 g, 8.5 mmol) were added. The resulting dark yellow reaction mixture was allowed to stir at room temperature under $N_2$ atmosphere overnight and then poured into saturated sodium bicarbonate solution (100 mL). The resulting precipitate was collected and dried under vacuum overnight to provide tert-butyl 4-(2-(4-carbamoylbenzyl)-2,3,4,5-tetrahydro-1H-pyrido[4,3-b]indole-8-carboxamido)piperidine-1-carboxylate (28 in Scheme 1(m)) as a white solid (0.75 g, 75%). $^1$H NMR (DMSO-$d_6$, 300 MHZ) 10.80 (s, 1H), 7.86-7.79 (m, 4H), 7.55 (d, J=8.5 Hz, 1H), 7.45 (d, J=8.3 Hz, 3H), 7.26 (d, J=8.5 Hz, 2H), 4.00-3.88 (m, 3H), 3.82 (s, 2H), 3.65 (s, 2H), 2.92-2.80 (m, 6H), 1.80 (d, J=9.9 Hz, 2H), 1.54-1.47 (m, 2H), 1.43 (s, 9H) ppm; MS (ES) 532 (M+H).

Step 2 i) A solution of tert-butyl 4-(2-(4-carbamoylbenzyl)-2,3,4,5-tetrahydro-1H-pyrido[4,3-b]indole-8-carboxamido)piperidine-1-carboxylate (28, 745 mg, 1.4 mmol) in 4 N HCl/dioxane (20.0 mL) was allowed to stir at room temperature for 2 h. The reaction mixture was then concentrated to give a tan solid which was triturated with ethyl ether to give 2-(4-carbamoylbenzyl)-N-(1-(4-cyanobenzyl)piperidin-4-yl)-2,3,4,5-tetrahydro-1H-pyrido[4,3-b]indole-8-carboxamide as an off-white solid (700 mg, 99%); MS (ES) 432 (M+H).

ii) To a solution of 2-(4-carbamoylbenzyl)-N-(1-(4-cyanobenzyl)piperidin-4-yl)-2,3,4,5-tetrahydro-1H-pyrido[4,3-b]indole-8-carboxamide (75 mg, 0.15 mmol) in DMF (1.0 mL), α-bromo-p-tolunitrile (32 mg, 0.16 mmol) and triethylamine (75 μL, 54 mg, 0.54 mmol) were added. The resulting reaction mixture was allowed to stir at room temperature overnight, poured into saturated sodium bicarbonate solution (20 mL) to give a white solid which was collected and triturated with ethyl ether to give 2-(4-carbamoylbenzyl)-N-(1-(4-cyanobenzyl)piperidin-4-yl)-2,3,4,5-tetrahydro-1H-pyrido[4,3-b]indole-8-carboxamide (Compound 44) (55 mg, 68%). $^1$H NMR (DMSO-$d_6$, 300 MHZ) 11.01 (s, 1H), 8.00 (d, J=7.4 Hz, 1H), 7.93 (br s, 1H), 7.84 (d, J=8.3 Hz, 2H), 7.82 (br s, 1H), 7.78 (d, J=8.3 Hz, 2H), 7.54 (dd, J=10.2, 1.4 Hz, 1H), 7.50 (d, J=8.3 Hz, 2H), 7.45 (d, J=8.3 Hz, 2H), 7.31 (br s, 1H), 7.25 (d, J=8.3 Hz, 1H), 3.81 (s, 2H), 3.78-3.68 (m, 1H), 3.60 (s, 2H), 3.55 (s, 2H), 2.88 (m, 6H), 2.05 (t, J=10.6 Hz, 2H), 1.76 (d, J=10.7 Hz, 2H), 1.58 (q, J=10.5 Hz, 2H) ppm; MS (ES) 547 (M+H).

2-(4-Carbamoylbenzyl)-N-(1-(pyridin-4-ylmethyl)piperidin-4-yl)-2,3,4,5-tetrahydro-1H-pyrido[4,3-b]indole-8-carboxamide (Compound 45) was prepared as described in step 2.ii of Synthetic Example 1(m) above (54%). $^1$H NMR (DMSO-$d_6$, 300 MHZ) 11.01 (s, 1H), 8.49 (dd, J=4.4, 1.4 Hz, 2H), 8.00 (d, J=8.0 Hz, 1H), 7.93 (br s, 1H), 7.84 (d, J=8.3 Hz, 2H), 7.83 (br s, 1H), 7.54 (d, J=8.5 Hz, 1H), 7.45 (d, J=8.0 Hz, 2H), 7.30 (d, J=5.8 Hz, 3H), 7.25 (d, J=8.5 Hz, 1H), 3.81 (s, 2H), 3.78-3.70 (m, 1H), 3.60 (s, 2H), 3.50 (s, 2H), 2.88-2.76 (m, 6H), 2.05 (t, J=11.0, 2H), 1.77 (d, J=11.3 Hz, 2H), 1.51 (q, J=11.8 Hz, 2H) ppm; MS (ES) 523 (M+H).

2-(4-Carbamoylbenzyl)-N-(1-isonicotinoylpiperidin-4-yl)-2,3,4,5-tetrahydro-1H-pyrido[4,3-b]indole-8-carboxamide (Compound 46) was prepared as described in step 2.ii of Synthetic Example 1(m) above (31%). $^1$H NMR (DMSO-$d_6$, 300 MHZ) 11.03 (s, 1H), 8.66 (dd, J=4.4, 1.7 Hz, 2H), 8.07 (d, J=7.2 Hz, 1H), 7.93 (br s, 1H), 7.84 (d, J=8.0 Hz, 2H), 7.82 (br s, 1H), 7.54 (d, J=8.3 Hz, 1H), 7.45 (d, J=8.0 Hz, 2H), 7.35 (dd, J=4.4, 1.7 Hz, 2H), 7.32 (br s, 1H), 7.26 (d, J=8.5 Hz, 1H), 4.44 (d, J=12.9 Hz, 1H), 4.13-4.00 (m, 1H), 3.81 (s, 2H), 3.59 (s, 2H), 3.45 (d, J=11.8 Hz, 1H), 3.17 (t, J=12.2 Hz, 1H), 2.94 (t, J=12.7 Hz, 1H), 2.84 (br s, 4H), 1.92 (d, J=11.0 Hz, 1H), 1.78 (d, J=11.0 Hz, 1H), 1.50 (q, J=12.8 Hz, 2H) ppm; MS (ES) 537 (M+H).

2-(4-Carbamoylbenzyl)-N-(1-(4-(trifluoromethyl)benzyl)piperidin-4-yl)-2,3,4,5-tetrahydro-1H-pyrido[4,3-b]indole-8-carboxamide (Compound 47) was prepared as described in step 2.ii of Synthetic Example 1(m) above (66%). $^1$H NMR (DMSO-$d_6$, 300 MHZ) 11.01 (s, 1H), 8.00 (d, J=7.4 Hz, 1H), 7.93 (br s, 1H), 7.84 (d, J=8.3 Hz, 2H), 7.83 (s, 1H), 7.68 (d, J=8.0 Hz, 2H), 7.55-7.51 (m, 3H), 7.45 (d, J=8.3 Hz, 2H), 7.31 (br s, 1H), 7.25 (d, J=8.3 Hz, 1H), 3.81 (s, 2H), 3.78-3.70 (m, 1H), 3.60 (s, 2H), 3.56 (s, 2H), 2.88-2.74 (m, 6H), 2.05 (t, J=11.1 Hz, 2H), 1.76 (d, J=10.2 Hz, 2H), 1.58 (q, J=10.7 Hz, 2H) ppm; MS (ES) 590 (M+H).

2-(4-Carbamoylbenzyl)-N-(1-(4-fluorobenzyl)piperidin-4-yl)-2,3,4,5-tetrahydro-1H-pyrido[4,3-b]indole-8-carboxamide (Compound 48) was prepared as described in step 2.ii of Synthetic Example 1(m) above (60%). $^1$H NMR (DMSO-$d_6$, 300 MHZ) 11.01 (s, 1H), 8.00 (d, J=7.7 Hz, 1H), 7.93 (br s, 1H), 7.84 (d, J=8.0 Hz, 2H), 7.82 (s, 1H), 7.54 (d, J=8.5 Hz, 1H), 7.45 (d, J=8.0 Hz, 2H), 7.34-7.29 (m, 3H), 7.25 (d, J=8.5 Hz, 1H), 7.13 (t, J=8.7 Hz, 2H), 3.81 (s, 2H), 3.78-3.68 (m, 1H), 3.60 (s, 2H), 3.44 (s, 2H), 2.88-2.74 (m, 6H), 2.00 (t, J=11.0 Hz, 2H), 1.75 (d, J=9.9 Hz, 2H), 1.56 (qd, J=11.8, 2.5 Hz, 2H) ppm; MS (ES) 539 (M+H).

2-(4-carbamoylbenzyl)-N-(1-(4-carbamoylbenzyl)piperidin-4-yl)-2,3,4,5-tetrahydro-1H-pyrido[4,3-b]indole-8-carboxamide (Compound 49) was prepared as described in step 2.ii of Synthetic Example 1(m) above (80%). $^1$H NMR (DMSO-$d_6$, 300 MHZ) 11.01 (s, 1H), 7.99 (d, J=7.4 Hz, 1H), 7.92 (d, J=5.8 Hz, 2H), 7.86-7.80 (m, 5H), 7.54 (d, J=8.5 Hz, 1H), 7.45 (d, J=8.0 Hz, 2H), 7.35 (d, J=8.0 Hz, 2H), 7.30 (d, J=3.3 Hz, 2H), 7.25 (d, J=8.5 Hz, 1H), 3.81 (s, 2H), 3.78-3.68 (m, 1H), 3.60 (s, 2H), 3.50 (s, 2H), 2.88-2.76 (m, 6H), 2.02 (t, J=11.3 Hz, 2H), 1.75 (d, J=10.7 Hz, 2H), 1.57 (q, J=10.64 Hz, 2H) ppm; MS (ES) 565 (M+H).

(n). Increase in AMPK activity

Compounds 1-54 were assayed for their ability to activate AMPK using an enzyme-linked immunosorbent assay. The $EC_{50}$ values for AMPK activation for compounds 1-54 are presented in Table 2 below, in which "A" is less than 0.5 μM; "B" is 0.5-1 μM; "C" is 1-5 μM; and "D" is 5-10 μM; "E" is 10-50 μM; and "F" is >100 μM:

TABLE 2

| Cpd No. | AMPK $EC_{50}$ |
|---|---|
| 1 | C |
| 2 | E |
| 3 | E |
| 4 | C |
| 5 | C |
| 6 | B |
| 7 | D |
| 8 | D |

TABLE 2-continued

| Cpd No. | AMPK EC$_{50}$ |
|---|---|
| 9 | A |
| 10 | B |
| 11 | A |
| 12 | A |
| 13 | A |
| 14 | A |
| 15 | A |
| 16 | A |
| 17 | B |
| 18 | C |
| 19 | F |
| 20 | C |
| 21 | B |
| 22 | B |
| 23 | C |
| 24 | C |
| 25 | E |
| 26 | E |
| 27 | C |
| 28 | C |
| 29 | C |
| 30 | C |
| 31 | C |
| 32 | C |
| 33 | C |
| 24 | C |
| 35 | E |
| 36 | F |
| 37 | D |
| 38 | E |
| 39 | E |
| 40 | F |
| 41 | E |
| 43 | F |
| 44 | E |
| 45 | F |
| 46 | F |
| 47 | E |
| 48 | F |
| 49 | F |
| 50 | A |
| 51 | B |
| 52 | C |
| 53 | E |
| 54 | A |

Example 2

(a) Synthetic Example 4-((4-benzylpiperazin-1-yl)methyl)-N-(1-benzylpiperidin-4-yl)benzamide (compound 55)

Step 1

To a stirred mixture of 4-formylbenzoic acid (1 g, 6.66 mmol) in anhydrous dichloromethane (5 mL) was added triethylamine (1.4 mL, 7.99 mmol), 1-(3-dimethylaminopropyl)-3-ethylcarbodiimide hydrochloride (1.53 g, 7.99 mmol), and 1-benzyl-piperidin-4-ylamine (1.26 mL, 6.66 mmol). The mixture was stirred at room temperature overnight and then concentrated under reduced pressure. The residue obtained was triturated with methanol. The resulting solids were collected by filtration, washed methanol and dried under reduced pressure to afford N-(1-benzylpiperidin-4-yl)-4-formylbenzamide as a white solid (1.7 g, 80%). $^1$H NMR (DMSO, 300 MHz): δ 8.41 (s, 1H), 7.85 (d, 2H), 7.77 (d, 2H), 7.28 (m, 5H), 3.78 (m, 1H), 3.4 (m, 2H), 3.80 (m, 2H), 2.05 (m, 2H), 1.45-1.80 (m, 4H); LCMS (m/z): 324 (MH$^+$).

Step 2

N-(1-Benzylpiperidin-4-yl)-4-formylbenzamide (100 mg, 0.31 mmol) and 1-benzylpipeazine (54 µL, 0.31 mmol) were mixed in 1,2 dichloroethane (5 mL) and treated with sodium triacetoxyborohydride (86 mg, 0.403 mmol). The mixture was stirred at room temperature under N$_2$ overnight. The reaction mixture was quenched with 1N NaOH, and the product was extracted with EtOAc. The organic layers were washed with brine and dried (MgSO$_4$). The final product was purified by flash chromatography (2% MeOH/CH$_2$Cl$_2$) to afford the title compound as a white solid. (104 mg, 70%) $^1$H NMR (CDCl$_3$, 300 MHz): δ 7.89 (d, 2H), δ 7.46-7.62 (m, 5H), δ 7.31-7.44 (m, 5H), δ 7.28 (d, 2H), δ 4.25 (s, 2H), δ 4.22 (s, 4H), δ 3.98 (m, 2H), δ 3.44 (m, 8H), δ 2.88 (m, 2H), δ2.56 (m, 2H), δ 2.45 (m, 2H), δ 2.20 (m, 2H); LCMS (m/z): 484 (MH$^+$).

(b) $^1$H-NMR and Mass Spectral Data

The following compounds were prepared using methods analogous to those described in Synthetic Example 2(a) and in Scheme 2.

Compound 56: N-(1-benzylpiperidin-4-yl)-4-((4-(cyclohexylmethyl)piperazin-1-yl)methyl)benzamide. $^1$H NMR (CDCl$_3$, 300 MHz): δ 7.68 (d, 2H), 7.29-7.38 (m, 7H), 6.05 (d, 1H), 4.02 (m, 1H), 3.61 (s, 2H), 3.57 (s, 2H), 2.97 (m, 2H), 2.28 (m, 4H), 2.02 (m, 2H), 1.77-2.05 (m, 12H), 1.23 (m, 7H), 0.91 (m, 4H); LCMS (m/z): 490 (MH$^+$).

Compound 57: N-(1-benzylpiperidin-4-yl)-4-((4-(5-(trifluoromethyl)pyridin-2-yl)piperazin-1-yl)methyl)benzamide. $^1$H NMR (CDCl$_3$, 300 MHz): δ 8.38 (s, 1H), 7.93 (d, 2H), 7.77 (d, 2H), 7.26-7.46 (m, 5H), 6.62 (d, 1H), 4.44 (m, 1H), 4.25 (s, 2H), 4.20 (s, 2H), 3.90 (m, 2H), 3.50 (m, 6H), 3.0 (m, 2H), 2.95 (m, 2H), 2.50 (m, 2H), 2.21 (m, 2H); LCMS (m/z): 538 (MH$^+$).

Compound 58: N-(1-benzylpiperidin-4-yl)-4-((4-(pyridin-2-yl)piperazin-1-yl)methyl)benzamide. $^1$H NMR (CDCl$_3$, 300 MHz): δ 8.36 (s, 1H), 7.78 (d, 1H), 7.43 (d, 2H), 7.42-7.66 (m, 7H), 7.16 (d, 1H), 6.61 (d, 2H), 4.20 (m, 1H), 4.10 (s, 2H), 3.65 (s, 2H), 3.65 (m, 4H), 3.42 (m, 2H), 2.70 (m, 6H), 2.20 (m, 2H); LCMS (m/z): 470 (MH$^+$).

Compound 59: 4-((4-benzylpiperazin-1-yl)methyl)-N-(1-(pyridin-4-ylmethyl)piperidin-4-yl)benzamide. $^1$H NMR (CDCl$_3$, 300 MHz): δ 8.48 (d, 2H), δ 8.16 (d, 1H), δ 7.75 (d, 2H), δ7.28 (m, 9H), δ 3.75 (m, 1H), δ 3.47 (s, 2H), δ 3.43 (s, 2H), δ 3.31 (s, 2H), δ 2.78 (m, 2H), δ 2.48 (s, 8H), δ 2.05 (m, 2H), δ 1.75 (m, 2H), δ 1.61 (m, 2H); LCMS (m/z): 484 (MH$^+$).

Compound 60: 4-((4-benzylpiperazin-1-yl)methyl)-N-(1-(pyridin-3-ylmethyl)piperidin-4-yl)benzamide. $^1$H NMR (CDCl$_3$, 300 MHz): δ 8.43 (m, 3H), δ 8.14 (d, 2H), δ 7.73 (d, 2H), δ7.66 (d, 2H), δ7.31 (m, 7H ), δ 3.74 (m, 1H), δ 3.47 (s, 2H), δ 3.43 (s, 2H), δ 3.31 (s, 2H), δ 2.81 (m, 2H), δ 2.48 (s, 8H), δ 2.11 (m, 2H), δ 1.65 (m, 2H), δ 1.55 (m, 2H); LCMS (m/z): 484 (MH$^+$).

Compound 61: 4-((4-benzylpiperazin-1-yl)methyl)-N-(1-(4-cyanobenzyl)piperidin-4-yl)benzamide. $^1$H NMR (CDCl$_3$, 300 MHz): δ 8.25 (d, 2H), δ 7.76 (m, 4H), δ 7.48 (d, 2H), δ7.28 (m, 5H), δ 3.74 (m, 1H), δ 3.55 (s, 2H), δ 3.48 (d, 2H), δ 3.31 (s, 2H), δ 2.78 (m, 2H), δ 2.48 (s, 8H), δ 2.08 (m, 2H), δ 1.75 (m, 2H), δ 1.58 (m, 2H); LCMS (m/z): 508 (MH$^+$).

Compound 62: 4-((4-benzylpiperazin-1-yl)methyl)-N-(1-(4-trifluoromethylbenzyl)piperidin-4-yl)benzamide. $^1$H NMR (CDCl$_3$, 300 MHz): δ 8.18 (d, 1H), δ 7.73 (d, 2H), δ 7.67 (d, 2H), δ 7.51 (d, 2H), δ 7.32 (d, 2H), δ7.26 (m, 5H ), δ 3.74 (m, 1H), δ 3.55 (s, 2H), δ 3.45 (d, 2H), δ 3.31 (s, 2H), δ

2.68 (m, 2H), δ 2.48 (s, 8H), δ 2.05 (m, 2H), δ 1.75 (m, 2H), δ 1.58 (m, 2H); LCMS (m/z): 551 (MH+).

(c) Increase in AMPK activity

Compounds 55-62 of Table 1 were assayed for their ability to activate AMPK using an enzyme-linked immunosorbent assay. The $EC_{50}$ values for AMPK activation for compounds 55-62 are presented in Table 3 below, in which "A" is less than 0.1 μM; "B" is 0.1-0.5 μM; "C" is 0.5-1 μM; and "D" is 1-10 μM; "E" is 10-100 μM; and "F" is >100 μM:

TABLE 3

| Cpd No. | AMPK $EC_{50}$ |
|---------|----------------|
| 55 | A |
| 56 | D |
| 57 | A |
| 58 | D |
| 59 | B |
| 60 | B |
| 61 | A |
| 62 | A |

Example 3

(a) Synthetic Example

N-(1-benzylpiperidin-4-yl)-6-(1-(4-(trifluoromethyl)phenyl)piperidin-4-yloxy)-2-naphthamide (Compound 65)

Step 1

To a stirred mixture of 6-hydroxy-2-napthoic acid (100 mg, 0.531 mmol) in anhydrous dimethylormamide (5 mL) was added triethylamine (163 μl, 1.168 mmol), 1-(3-dimethylaminopropyl)-3-ethylcarbodiimide hydrochloride (112 mg, 0.584 mmol), and 1-benzyl-piperidine-4-amine (100 μl, 0.531 mmol). The mixture was allowed to stir at room temperature overnight, then poured into water. The resulting solids were collected by filtration and purified by column chromatography to yield N-(1-benzylpiperidin-4-yl)-6-hydroxy-2-naphthamide as a light brown solid (0.191 g, 80%).

Step 2

To a stirred suspension of N-(1-benzylpiperidin-4-yl)-6-hydroxy-2-naphthamide (0.1 g, 0.277 mmol) in toluene (5 mL) at room temperature was added diisopropyl azodicarboxylate (82 μl, 0.416 mmol), 1-(4-(trifluoromethyl)phenyl)piperidin-4-ol (0.068 g, 0.277 mmol), and triphenyl phosphine (0.109 g, 0416 mmol). The mixture was stirred at 50° C. overnight, then concentrated under reduced pressure. The residue was purified by flash chromatography (silica gel, 3% methanol in methylene chloride) to afford the title compound as a white solid (0.093 g, 57%). $^1$H-NMR (CDCl$_3$, 300 MHz): δ 8.738 (s, 1H), 8.242 (s, 1H), 8.093 (s, 1H), 7.837-7.250 (m, 11H), 7.167 (s, 1H), 6.87 (m, 1H), 4.63 (m, 1H), 4.31 (m, 1H), 4.162 (s, 2H), 3.647 (m, 2H), 3.557 (m, 2H), 3.519 (m, 2H), 2.814 (m, 2H), 2.584 (m, 2H), 2.222-2.083 (m, 6H); LCMS: >98%; MS : 588.28 (M+1).

(b) Increase in AMPK activity

Compounds 63-66 of Table 1 were assayed for their ability to activate AMPK using an enzyme-linked immunosorbent assay. The $EC_{50}$ values for AMPK activation for compounds 63-66 are presented in Table 4 below, in which "A" is less than 0.5 μM; "B" is 0.5-1 μM; "C" is 1-5 μM; and "D" is 5-50 μM:

TABLE 4

| Cpd No. | AMPK $EC_{50}$ |
|---------|----------------|
| 63 | A |
| 64 | A |
| 65 | C |
| 66 | C |

Example 4

(a) Synthetic Example

N-(1-(4-cyanobenzyl)piperidin-4-yl)-6-(1-(4-(trifluoromethyl)phenyl)piperidin-4-yloxy)quinoline-3-carboxamide (Compound 69)

Step 1

6-Methoxyquinoline-3-carboxylic acid (2.5 g, 12.3 mmol) was suspended in anhydrous dichloromethane (20 mL) under nitrogen; the suspension was cooled to −78° C. A solution of BBr$_3$ in dichloromethane (100 mL of 1M solution, 100 mmol) was added dropwise. The mixture was stirred for 30 min at −78° C., warmed slowly to RT, and allowed to stir at room temperature overnight. The reaction was quenched by dropwise addition of ice-water. The resulting solids were collected by filtration, and washed with water to yield 3.2 g (97%) of 6-hydroxyquinoline-3-carboxylic acid as an HBr salt. LCMS: >98%; MS: 190.27 (M+1, free base).

Step 2

To a stirred mixture of the product of step a (500 mg, 2.63 mmol) in anhydrous dimethylormamide (5 mL) was added triethylamine (733 μL, 5.62 mmol), HATU (1.1 g, 2.89 mmol), and tert-butyl 4-aminopiperidine-1-carboxylate (526 mg, 2.63 mmol). The mixture was allowed to stir at room temperature overnight and then poured into water. The resulting solids were collected by filtration and purified by column chromatography to yield tert-butyl 4-(6-hydroxyquinoline-3-carboxamido)piperidine-1-carboxylate as a light brown solid (0.7 g, 71%). LCMS (m/z): 372 (MH+)

Step 3

To a stirred suspension of the product of step 2 above (0.7 g, 1.88 mmol) in toluene (15 mL) at room temperature was added diisopropyl azodicarboxylate (557 μl, 2.83 mmol), 1-(4-(trifluoromethyl)phenyl)piperidin-4-ol (0.693 g, 2.83 mmol), and triphenyl phosphine (0.742 g, 2.83 mmol). The mixture was stirred at 50° C. overnight and then concentrated under reduced pressure. The residue was purified by flash chromatography (silica gel, 3% methanol in methylene chloride) to afford tert-butyl 4-(6-(1-(4-(trifluoromethyl)phenyl)piperidin-4-yloxy)quinoline-3-carboxamido)piperidine-1-carboxylate as a white solid (0.306 g, 27%). LCMS (m/z): 599 (MH+)

Step 4

The product of step 3 above was dissolved in 4N HCl in dioxane, and stirred for 1 h at room temperature. The reaction mixture was concentrated to dryness. The residue (100 mg, 0.31 mmol) and 4-cyanobenzaldehyde (33 mg, 0.247 mmol) were mixed in 1,2 dichloroethane (5 mL) and treated with sodium triacetoxyborohydride (70 mg, 0.328 mmol). The mixture was stirred at room temperature under N$_2$ overnight, then quenched with 1N NaOH, and the product was extracted with EtOAc. The organic layers were washed with brine and dried (MgSO$_4$). The final product was purified by flash chromatograph (2% MeOH/DCM) to afford the title compound as a white solid (87%). $^1$H-NMR (CDCl$_3$, 300 MHz): δ 9.1 (s, 1H), 8.468 (s, 1H), 8.015 (d, 2H), 7.689 (m, 4H), 7.467 (m, 4H), 7.178 (s, 1H), 6.965 (d, 2H), 4.691 (s, 2H), 4.295 (m, 1H), 3.910 (m, 1H), 3.628 (m, 2H), 3.336 (m, 4H), 2.592 (m, 2H), 2.174-2.053 (m, 8H); LCMS (m/z): 614 (MH$^+$).

(b) Increase in AMPK Activity

Compounds 67-71 of Table 1 were assayed for their ability to activate AMPK using an enzyme-linked immunosorbent assay. The EC$_{50}$ values for AMPK activation for compounds 67-71 are presented in Table 5 below, in which "A" is less than 0.1 µM; "B" is 0.1-0.5 µM; "C" is 0.5-5 µM; and "D" is >5 µM:

TABLE 5

| Cpd No. | AMPK EC$_{50}$ |
|---|---|
| 67 | B |
| 68 | D |
| 69 | A |
| 70 | A |
| 71 | A |

Example 5

(a) Synthetic Example

N-(1-benzylpiperidin-4-yl)-5-(1-(4-(trifluoromethyl)phenyl)piperidin-4-yloxy)-1H-indole-2-carboxamide (Compound 72)

Step 1

To a stirred mixture of 5-hydroxy-1H-indole-2-carboxylic acid (1.85 g, 10.43 mmol) in anhydrous dimethylformamide (15 mL) was added triethylamine (1.73 mL), 1-hydroxybenzotriazole (1.64 g), 1-(3-dimethylaminopropyl)-3-ethylcarbodiimide hydrochloride (2.39 g) and 1-benzylpiperidin-4-ylamine (2.39 g, 12.54 mmol). The reaction mixture was stirred at room temperature over-night and then solvents were removed under reduced pressure, poured into water, filter the solid and washed with water. The solid was purified by silica gel column chromatography, eluted with CH$_2$Cl$_2$:MeOH (93:7) to afford 0.87 g (24%) of N-(1-benzylpiperidin-4-yl)-5-hydroxy-1H-indole-2-carboxamide as a white solid. $^1$H NMR (DMSO-d$_6$, 300 MHz): δ 11.17(s, 1H), 8.72 (s, 1H), 8.07 (d, J=7.8 Hz, 1H), 7.7.29 (m, 6H), 6.91 (s, 1H), 6.82 (s, 1H), 6.68 (m, 1H), 3.75 (br s, 1H), 3.46 (s, 2H), 2.81 (d, J=11.4 Hz, 2H), 2.02 (t, J=10.8 Hz, 2H), 1.77 (m, 2H), 1.56 (m, 2H); LCMS (m/z): 350 (MH$^+$).

Step 2

To a stirred mixture of N-(1-benzylpiperidin-4-yl)-5-hydroxy-1H-indole-2-carboxamide (85.5 mg, 0.245 mmol) in anhydrous toluene (3 mL) at room temperature was added diisopropyl azodicarboxylate (0.05 mL, 0.25 mmol), 1-(4-trifluorophenyl)piperidin-4-ol (60 mg, 0.245 mmol) and triphenylphosphine (64 mg, 0.25 mmol). The reaction mixture was heated with stirred at 80° C. under N$_2$ atmosphere over-night and then concentrated under reduced pressure. The residue thus obtained was purified by silica gel column chromatography, eluted with CH$_2$Cl$_2$:MeOH (97:3) and finally by HPLC to afford N-(1-benzylpiperidin-4-yl)-5-(1-(4-(trifluoromethyl)phenyl)piperidin-4-yloxy)-1H-indole-2-carboxamide (10 mg) as a white solid. LCMS (m/z): 577 (MH$^+$).

(b) Increase in AMPK Activity

Compound 72 of Table 1 was assayed for its ability to activate AMPK using an enzyme-linked immunosorbent assay. The EC$_{50}$ values for AMPK activation for compound 72 is presented in Table 6 below, in which "A" is less than 0.1 µM; "B" is 0.1-0.5 µM; "C" is 0.5-1 µM; and "D" is 1-50 µM:

TABLE 6

| Cpd No. | AMPK EC$_{50}$ |
|---|---|
| 1 | A |

What is claimed is:
1. A compound having the structural formula

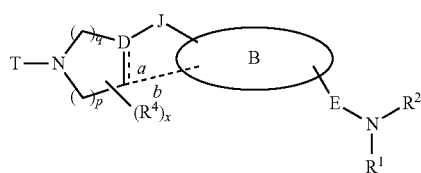

or a pharmaceutically acceptable salt or N-oxide thereof, wherein

"B" represents -(aryl or heteroaryl)- substituted by w R$^3$ and k R$^{14}$;

the dotted line denoted by "b" is a single bond or a double bond;

the dotted line denoted by "a" is a bond or absent, provided that if the dotted line denoted by "b" is a double bond, then the dotted line denoted by "a" is absent;

D is a carbon or N when the dotted line denoted by "a" is absent, and a carbon when the dotted line denoted by "a" is a bond;

J is —O—, —N(R$^{38}$)—, —CH$_2$—, —CH(R$^{26}$)— or —C(R$^{26}$)$_2$—;

E is —C(O)—, —S(O)$_2$— or a single bond, provided that when "B" is phenyl, J is —O— and D is a carbon, E is not —C(O)—;

R$^1$ is H, —(C$_1$-C$_4$ alkyl), —C(O)—(C$_1$-C$_4$ alkyl) or —C(O)O—(C$_1$-C$_4$ alkyl);

R$^2$ is -Hca, -Cak-N(R$^9$)-G-R$^{22}$ or —(C$_2$-C$_8$ alkyl)-N(R$^9$)—R$^{24}$ in which one or two carbons of the (C$_2$-C$_8$ alkyl) are optionally replaced by —O—, —S— or —N(R$^9$)— and R$^{24}$ is —R$^{23}$, -G-R$^{23}$, or —C(O)O—(C$_1$-C$_6$ alkyl), provided that two consecutive carbons of the (C$_2$-C$_8$ alkyl) are not replaced by —O—;

each R$^3$ is substituted on a benzo, pyrido or pyrazino carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

w is 0, 1, 2 or 3;

each R$^{14}$ is substituted on a non-benzo, non-pyrido, non-pyrazino carbon of the ring system denoted by "B", and is independently selected from —(C$_1$-C$_6$ alkyl), —(C$_1$-C$_6$ halooalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

k is 0, 1 or 2;

each R$^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^4$ on the same carbon optionally combine to form oxo;

x is 0, 1, 2, 3 or 4;
p is 0, 1, 2, 3 or 4;
q is 0, 1, 2, 3 or 4;
the sum of p and q is 1, 2, 3 or 4;
T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$ or

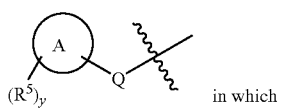

in which

Q is —S(O)$_2$— L or —(C$_0$-C$_3$ alkyl)-, in which each carbon of the —(C$_0$-C$_3$ alkyl)- is optionally and independently substituted with one or two R$^{16}$;
the ring system denoted by "A" is heteroaryl, aryl, cycloalkyl or heterocycloalkyl;
each R$^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, —(C$_0$-C$_6$ alkyl)-C(O)R$^{10}$, -halogen, —NO$_2$ and —CN; and
y is 0, 1, 2, 3 or 4;

in which
each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—,
each R$^6$, R$^7$, R$^8$ and R$^{10}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl),
each R$^9$ is independently selected from —H, —(C$_1$-C$_4$ alkyl), —C(O)—(C$_1$-C$_4$ alkyl) and —C(O)O—(C$_1$-C$_4$ alkyl),
each G is independently —S(O)$_2$—, L or —(C$_0$-C$_3$ alkyl)-, in which each carbon of the —(C$_0$-C$_3$ alkyl)- is optionally and independently substituted with one or two R$^{16}$,
each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo,
each R$^{26}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{26}$ on the same carbon combine to form oxo,
each R$^{38}$ is independently selected from —H, —(C$_1$-C$_4$ alkyl), —C(O)—(C$_1$-C$_4$ alkyl) and —C(O)O—(C$_1$-C$_4$ alkyl),
each R$^{22}$ and R$^{23}$ is independently Ar or Het,
each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted,
wherein when the compound has the structure formula (II) or (III)

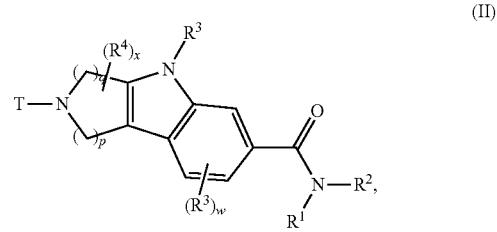

(II)

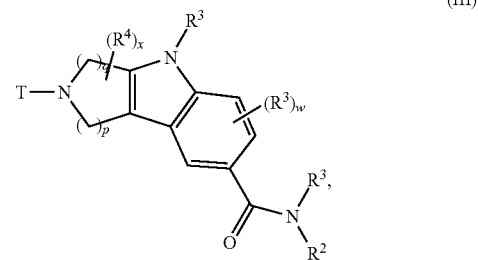

(III)

wherein R$^1$, R$^3$, R$^4$, w, x, p, q, T, and R$^{38}$ are as defined above,
then R$^2$ is not tetrahydro-2H-pyran-4-yl or tetrahydrothiophene S,S-dioxide.

2. A compound according to claim 1, wherein "B" represents

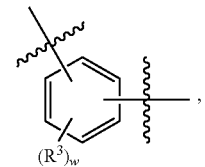

the dotted line denoted by "b" is a single bond, the dotted line denoted by "a" is a bond, k is 0, J is —N(R$^{38}$)— and D is a carbon.

3. A compound according to claim 1, wherein the "B" represents

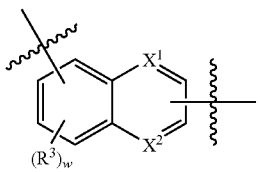

in which $X^1$ and $X^2$ are independently a carbon or N, and k is 0.

4. A compound according to claim 3, wherein one of $X^1$ and $X^2$ is a carbon and the other is N.

5. A compound according to claim 1, wherein "B" represents

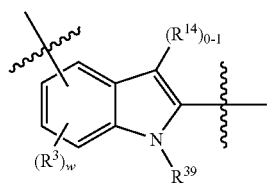

in which $R^{39}$ is H, —($C_1$-$C_4$ alkyl), —C(O)—($C_1$-$C_4$ alkyl) or —C(O)O—($C_1$-$C_4$ alkyl).

6. A compound according to claim 1, wherein E is —C(O)—.

7. A compound according to claim 1, wherein T is

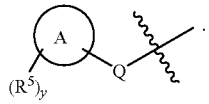

8. A compound according to claim 7, wherein each $R^{16}$ is independently selected from —($C_1$-$C_6$ alkyl), —($C_1$-$C_6$ haloalkyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group.

9. A compound according to claim 7, wherein Q is —$CH_2$—, a single bond, —C(O)—, —S(O)$_2$— or —CH($CH_3$)—.

10. A compound according to claim 7, wherein each $R^5$ is independently selected from —($C_1$-$C_6$ alkyl), —($C_1$-$C_6$ haloalkyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group.

11. A compound according to claim 7, wherein the ring system denoted by "A" is an aryl or a heteroaryl.

12. A compound according to claim 7, wherein the ring system denoted by "A" is a phenyl.

13. A compound according to claim 1, wherein the sum of p and q is 2 or 3.

14. A compound according to claim 1, wherein $R^1$ is H.

15. A compound according to claim 1, wherein $R^2$ is Hca.

16. A compound according to claim 15, wherein $R^2$ is an optionally-substituted monocyclic heterocycloalkyl.

17. A compound according to claim 15, wherein $R^2$ is -(optionally-substituted azetidin-3-yl), -(optionally substituted piperidin-4-yl), -(optionally substituted pyrrolidin-3-yl) or -(optionally-substituted azepan-4-yl).

18. A compound according to claim 17, wherein $R^2$ is substituted at its 1-position with —($C_0$-$C_3$ alkyl)-Ar or —($C_0$-$C_3$ alkyl)-Het.

19. A compound according to claim 17, wherein $R^2$ is substituted at its 1-position with —C(O)—O($C_0$-$C_6$ alkyl), —C(O)-Het, —C(O)-Ar, —S(O)$_2$-Het, —S(O)$_2$-Ar or —S(O)$_2$—O($C_0$-$C_6$ alkyl).

20. A compound according to claim 17, wherein $R^2$ is substituted at its 1-position with —C(O)—$NR^9$-Het or —C(O)—$NR^9$-Ar.

21. A compound according to claim 1 wherein $R^2$ is -Cak-N($R^9$)-G-$R^{22}$.

22. A compound according to claim 1, wherein $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -$GR^{23}$, or —C(O)O—($C_1$-$C_6$ alkyl).

23. A compound according to claim 1, wherein each $R^3$ is independently selected from —($C_1$-$C_6$ alkyl), —($C_1$-$C_6$ haloalkyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group.

24. A compound according to claim 1, wherein each $R^4$ is independently selected from —($C_1$-$C_6$ alkyl), —($C_1$-$C_6$ haloalkyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group.

25. A compound according to claim 1, having the structural formula

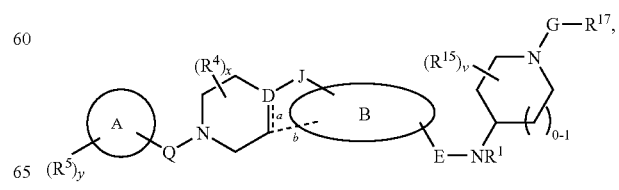

in which

Q and G are each independently a bond, —CH$_2$—, —C(H)(R$^{16}$)—, —C(R$^{16}$)$_2$—, L or —S(O)$_2$—;

v is 0, 1, 2, 3 or 4;

each R$^{15}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^{15}$ on the same carbon optionally combine to form oxo;

R$^{17}$ is Het or Ar.

26. A compound according to claim 25, having the structural formula

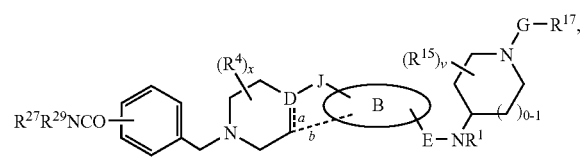

in which R$^{27}$ is selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl) -C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —C(O)—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

27. A compound according to claim 25, having the structural formula

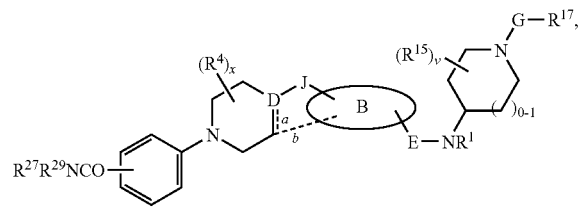

in which R$^{27}$ is selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

28. A compound according to claim 25, having the structural formula

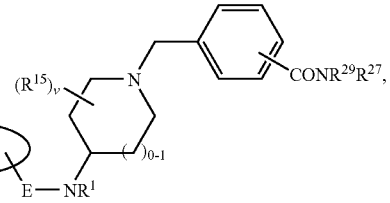

in which R$^{27}$ is selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

29. A compound according to claim 25, having the structural formula

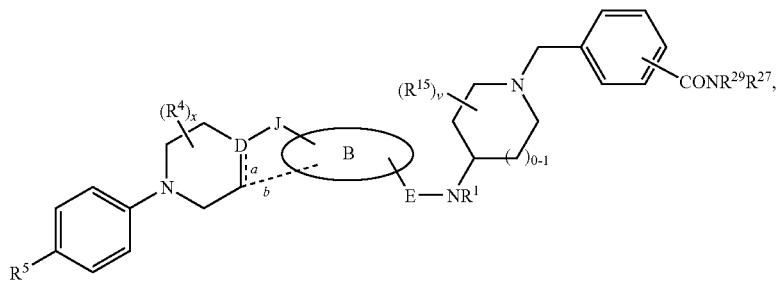

in which $R^{27}$ is selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

30. A compound according to claim 25, having the structural formula

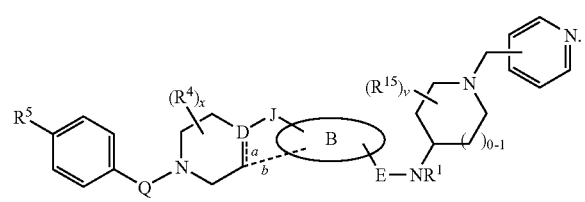

31. A compound according to claim 25, having the structural formula

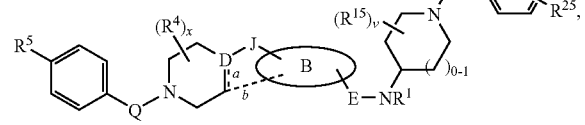

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl or haloalkyl is substituted by an aryl, heteroaryl, cycloalkyl or heterocycloalkyl-containing group.

32. A compound according to claim 25, having the structural formula

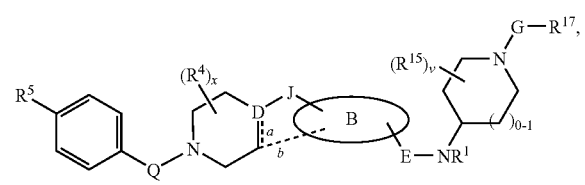

in which Q is —C(O)—, —S(O)$_2$— or —C(O)—NH—.

33. A compound according to claim 25, having the structural formula

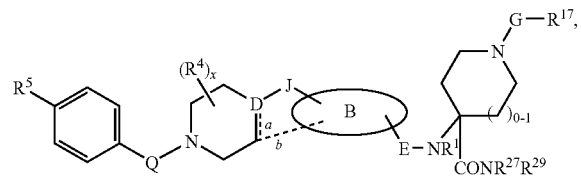

in which $R^{27}$ is selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

34. A compound according claim 25, having the structural formula

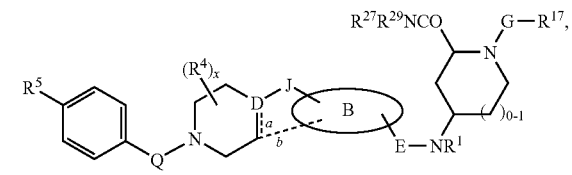

in which $R^{27}$ is selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

35. A compound according to claim 25, wherein the

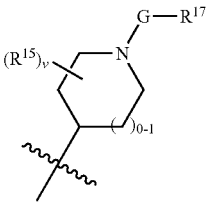

moiety has the structure

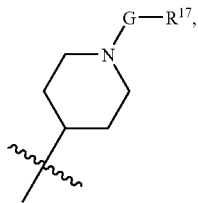

in which G is —CH₂—, —CH(CH₃)—, —C(O)—, —S(O)₂— or —C(O)—NH—.

36. A compound according to claim 25, wherein the

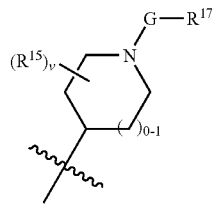

moiety has the structure

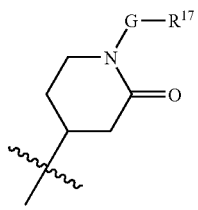

in which G is —CH₂—, —C(O)—, —S(O)₂— or —C(O)—NH—.

37. A compound which is
benzyl 8-(1-(4-cyanobenzyl)piperidin-4-ylcarbamoyl)-3,4-dihydro-1H-pyrido[4,3-b]indole-2(5H)-carboxylate;
benzyl 8-(1-(4-benzyl)piperidin-4-ylcarbamoyl)-3,4-dihydro-1H-pyrido[4,3-b]indole-2(5H)-carboxylate;
benzyl 8-(1-(tert-butoxycarbonyl)piperidin-4-ylcarbamoyl)-3,4-dihydro-1H-pyrido[4,3-b]indole-2(5H)-carboxylate;
2-benzyl-N-(1-(4-cyanobenzyl)piperidin-4-yl)-2,3,4,5-tetrahydro-1H-pyrido[4,3-b]indole-8-carboxamide;
2-benzyl-N-(1-(4-trifluoromethylbenzyl)piperidin-4-yl)-2,3,4,5-tetrahydro-1H-pyrido[4,3-b]indole-8-carboxamide;
tert-butyl 4-(2-(4-(trifluoromethyl)benzyl)-2,3,4,5-tetrahydro-1H-pyrido[4,3-b]indole-8-carboxamido)piperidine-1-carboxylate;
2-benzyl-N-(1-(pyridin-4-ylmethyl)piperidin-4-yl)-2,3,4,5-tetrahydro-1H-pyrido[4,3-b]indole-8-carboxamide;
2-(4-fluorobenzyl)-N-(1-(pyridin-3-ylmethyl)piperidin-4-yl)-2,3,4,5-tetrahydro-1H-pyrido[4,3-b]indole-8-carboxamide;
N-(1-(4-cyanobenzyl)piperidin-4-yl)-2-(4-fluorobenzyl)-2,3,4,5-tetrahydro-1H-pyrido[4,3-b]indole-8-carboxamide;
N-(1-(4-trifluoromethylbenzyl)piperidin-4-yl)-2-(4-fluorobenzyl)-2,3,4,5-tetrahydro-1H-pyrido[4,3-b]indole-8-carboxamide;
N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide;
N-(1-(4-cyanobenzyl)piperidin-4-yl)-2-(4-(trifluoromethyl)benzyl)-2,3,4,5-tetrahydro-1H-pyrido[4,3-b]indole-8-carboxamide;
N-(1-(4-trifluoromethylbenzyl)piperidin-4-yl)-2-(4-(trifluoromethyl)benzyl)-2,3,4,5-tetrahydro-1H-pyrido[4,3-b]indole-8-carboxamide;
N-(1-phenethylpiperidin-4-yl)-2-(4-(trifluoromethyl)benzyl)-2,3,4,5-tetrahydro-1H-pyrido[4,3-b]indole-8-carboxamide;
N-(1-(4-fluorophenyl)piperidin-4-yl)-2-(4-(trifluoromethyl)benzyl)-2,3,4,5-tetrahydro-1H-pyrido[4,3-b]indole-8-carboxamide;
N-(1-(4-cyanobenzyl)piperidin-4-yl)-5-methyl-2-(4-(trifluoromethyl)benzyl)-2,3,4,5-tetrahydro-1H-pyrido[4,3-b]indole-8-carboxamide;
N-(1-(4-trifluoromethylbenzyl)piperidin-4-yl)-5-methyl-2-(4-(trifluoromethyl)benzyl)-2,3,4,5-tetrahydro-1H-pyrido[4,3-b]indole-8-carboxamide;
5-methyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide;
N-(1-benzylpiperidin-4-yl)-2-(4-(trifluoromethyl)phenylsulfonyl)-2,3,4,5-tetrahydro-1H-pyrido[4,3-b]indole-8-carboxamide;
5-acetyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide;
N-(1-(4-cyanophenylsulfonyl)piperidin-4-yl)-2-(4-(trifluoromethyl)benzyl)-2,3,4,5-tetrahydro-1H-pyrido[4,3-b]indole-8-carboxamide;
N-(1-(pyridin-3-ylsulfonyl)piperidin-4-yl)-2-(4-(trifluoromethyl)benzyl)-2,3,4,5-tetrahydro-1H-pyrido[4,3-b]indole-8-carboxamide;
2-(4-(trifluoromethyl)benzyl)-N-(1-(4-(trifluoromethyl)phenylsulfonyl)piperidin-4-yl)-2,3,4,5-tetrahydro-1H-pyrido[4,3-b]indole-8-carboxamide;
N-(1-(4-cyanobenzyl)piperidin-4-yl)-2-(4-(trifluoromethyl)phenylsulfonyl)-2,3,4,5-tetrahydro-1H-pyrido[4,3-b]indole-8-carboxamide;
N-(1-(4-cyanobenzyl)piperidin-4-yl)-2-(4-cyanophenylsulfonyl)-2,3,4,5-tetrahydro-1H-pyrido[4,3-b]indole-8-carboxamide;
N-(1-(4-cyanobenzyl)piperidin-4-yl)-2-(pyridin-3-ylsulfonyl)-2,3,4,5-tetrahydro-1H-pyrido[4,3-b]indole-8-carboxamide;
N-(1-(4-cyanophenylcarbamoyl)piperidin-4-yl)-2-(4-(trifluoromethyl)benzyl)-2,3,4,5-tetrahydro-1H-pyrido[4,3-b]indole-8-carboxamide;
N-(1-(4-fluorophenylsulfonyl)piperidin-4-yl)-2-(4-(trifluoromethyl)benzyl)-2,3,4,5-tetrahydro-1H-pyrido[4,3-b]indole-8-carboxamide;
N-(1-(3-cyanophenylsulfonyl)piperidin-4-yl)-2-(4-(trifluoromethyl)benzyl)-2,3,4,5-tetrahydro-1H-pyrido[4,3-b]indole-8-carboxamide;
2-(4-(trifluoromethyl)benzyl)-N-(1-(3-(trifluoromethyl)phenylsulfonyl)piperidin-4-yl)-2,3,4,5-tetrahydro-1H-pyrido[4,3-b]indole-8-carboxamide;
N-(1-(3-fluorophenylcarbamoyl)piperidin-4-yl)-2-(4-(trifluoromethyl)benzyl)-2,3,4,5-tetrahydro-1H-pyrido[4,3-b]indole-8-carboxamide;
N-(1-(4-chlorophenylsulfonyl)piperidin-4-yl)-2-(4-(trifluoromethyl)benzyl)-2,3,4,5-tetrahydro-1H-pyrido[4,3-b]indole-8-carboxamide;
2-(4-(trifluoromethyl)benzyl)-N-(1-(4-(trifluoromethyl)phenylcarbamoyl)piperidin-4-yl)-2,3,4,5-tetrahydro-1H-pyrido[4,3-b]indole-8-carboxamide;

N-(1-(4-cyanobenzyl)piperidin-4-yl)-2-(4-fluorophenyl)-2,3,4,5-tetrahydro-1H-pyrido[4,3-b]indole-8-carboxamide;

2-(4-fluorophenyl)-N-(1-(4-fluorophenylsulfonyl)piperidin-4-yl)-2,3,4,5-tetrahydro-1H-pyrido[4,3-b]indole-8-carboxamide;

2-(4-fluorophenyl)-N-(1-(pyridin-3-ylmethyl)piperidin-4-yl)-2,3,4,5-tetrahydro-1H-pyrido[4,3-b]indole-8-carboxamide;

2-(4-fluorophenyl)-N-(1-(4-(trifluoromethyl)benzyl)piperidin-4-yl)-2,3,4,5-tetrahydro-1H-pyrido[4,3-b]indole-8-carboxamide;

tert-butyl 4-(2-(4-fluorophenyl)-2,3,4,5-tetrahydro-1H-pyrido[4,3-b]indole-8-carboxamido)piperidine-1-carboxylate;

N-(1-(4-fluorobenzoyl)piperidin-4-yl)-2-(4-fluorophenyl)-2,3,4,5-tetrahydro-1H-pyrido[4,3-b]indole-8-carboxamide;

2-(4-fluorophenyl)-N-(1-nicotinoylpiperidin-4-yl)-2,3,4,5-tetrahydro-1H-pyrido[4,3-b]indole-8-carboxamide;

2-(4-fluorophenyl)-N-(1-(4-(trifluoromethyl)benzoyl)piperidin-4-yl)-2,3,4,5-tetrahydro-1H-pyrido[4,3-b]indole-8-carboxamide;

N-(1-nicotinoylpiperidin-4-yl)-2-(4-(trifluoromethyl)benzyl)-2,3,4,5-tetrahydro-1H-pyrido[4,3-b]indole-8-carboxamide;

tert-butyl 4-(2-(4-carbamoylbenzyl)-2,3,4,5-tetrahydro-1H-pyrido[4,3-b]indole-8-carboxamido)piperidine-1-carboxylate;

2-(4-carbamoylbenzyl)-N-(1-(4-cyanobenzyl)piperidin-4-yl)-2,3,4,5-tetrahydro-1H-pyrido[4,3-b]indole-8-carboxamide;

2-(4-carbamoylbenzyl)-N-(1-(pyridin-4-ylmethyl)piperidin-4-yl)-2,3,4,5-tetrahydro-1H-pyrido[4,3-b]indole-8-carboxamide;

2-(4-carbamoylbenzyl)-N-(1-isonicotinoylpiperidin-4-yl)-2,3,4,5-tetrahydro-1H-pyrido[4,3-b]indole-8-carboxamide;

2-(4-carbamoylbenzyl)-N-(1-(4-(trifluoromethyl)benzyl)piperidin-4-yl)-2,3,4,5-tetrahydro-1H-pyrido[4,3-b]indole-8-carboxamide;

2-(4-carbamoylbenzyl)-N-(1-(4-fluorobenzyl)piperidin-4-yl)-2,3,4,5-tetrahydro-1H-pyrido[4,3-b]indole-8-carboxamide;

2-(4-carbamoylbenzyl)-N-(1-(4-carbamoylbenzyl)piperidin-4-yl)-2,3,4,5-tetrahydro-1H-pyrido[4,3-b]indole-8-carboxamide N-(1-(pyridin-4-ylmethyl)piperidin-4-yl)-2-(4-(trifluoromethyl)benzyl)-2,3,4,5-tetrahydro-1H-pyrido[4,3-b]indole-8-carboxamide;

N-(1-isonicotinoylpiperidin-4-yl)-2-(4-(trifluoromethyl)benzyl)-2,3,4,5-tetrahydro-1H-pyrido[4,3-b]indole-8-carboxamide;

N-(1-(4-carbamoylbenzyl)piperidin-4-yl)-2-(4-(trifluoromethyl)benzyl)-2,3,4,5-tetrahydro-1H-pyrido[4,3-b]indole-8-carboxamide;

N-(1-((1-methyl-1H-imidazol-4-yl)methyl)piperidin-4-yl)-2-(4-(trifluoromethyl)benzyl)-2,3,4,5-tetrahydro-1H-pyrido[4,3-b]indole-8-carboxamide;

N-(1-(oxazol-4-ylmethyl)piperidin-4-yl)-2-(4-(trifluoromethyl)benzyl)-2,3,4,5-tetrahydro-1H-pyrido[4,3-b]indole-8-carboxamide;

4-((4-benzylpiperazin-1-yl)methyl)-N-(1-benzylpiperidin-4-yl)benzamide

N-(1-benzylpiperidin-4-yl)-4-((4-(cyclohexylmethyl)piperazin-1-yl)methyl)benzamide;

N-(1-benzylpiperidin-4-yl)-4-((4-(5-(trifluoromethyl)pyridin-2-yl)piperazin-1-yl)methyl)benzamide;

N-(1-benzylpiperidin-4-yl)-4-((4-(pyridin-2-yl)piperazin-1-yl)methyl)benzamide 4-((4-benzylpiperazin-1-yl)methyl)-N-(1-(pyridin-4-ylmethyl)piperidin-4-yl)benzamide;

4-((4-benzylpiperazin-1-yl)methyl)-N-(1-(pyridin-3-ylmethyl)piperidin-4-yl)benzamide;

4-((4-benzylpiperazin-1-yl)methyl)-N-(1-(4-cyanobenzyl)piperidin-4-yl)benzamide 4-((4-benzylpiperazin-1-yl)methyl)-N-(1-(4-trifluoromethylbenzyl)piperidin-4-yl)benzamide;

N-(1-benzylpiperidin-4-yl)-6-(1-(4-(trifluoromethyl)benzyl)piperidin-4-yloxy)-2-naphthamide;

N-(1-benzylpiperidin-4-yl)-6-(1-(4-cyanobenzyl)piperidin-4-yloxy)-2-naphthamide

N-(1-benzylpiperidin-4-yl)-6-(1-(4-(trifluoromethyl)phenyl)piperidin-4-yloxy)-2-naphthamide;

tert-butyl 4-(7-(1-(4-(trifluoromethyl)phenyl)piperidin-4-yloxy)-2-naphthamido)piperidine-1-carboxylate;

tert-butyl 4-(6-(1-(4-(trifluoromethyl)phenyl)piperidin-4-yloxy)quinoline-3-carboxamido)piperidine-1-carboxylate;

N-(piperidin-4-yl)-6-(1-(4-(trifluoromethyl)phenyl)piperidin-4-yloxy)quinoline-3-carboxamide;

N-(1-(4-cyanobenzyl)piperidin-4-yl)-6-(1-(4-(trifluoromethyl)phenyl)piperidin-4-yloxy)quinoline-3-carboxamide;

N-(1-(4-(trifluoromethyl)benzyl)piperidin-4-yl)-6-(1-(4-(trifluoromethyl)phenyl)piperidin-4-yloxy)quinoline-3-carboxamide;

N-(1-benzylpiperidin-4-yl)-6-(1-(4-(trifluoromethyl)phenyl)piperidin-4-yloxy)quinoline-3-carboxamide; or N-(1-benzylpiperidin-4-yl)-5-(1-(4-(trifluoromethyl)phenyl)piperidin-4-yloxy)-1H-indole-2-carboxamide.

38. A pharmaceutical composition comprising:
at least one pharmaceutically acceptable carrier, diluent or excipient; and
a compound according to claim 1 or a pharmaceutically acceptable salt or N-oxide thereof.

39. A method for activating the AMPK pathway in a cell, the method comprising
contacting the cell with an effective amount of a compound according to claim 1, or a pharmaceutically acceptable salt or N-oxide thereof.

40. A method for increasing fatty acid oxidation in a cell, the method comprising
contacting the cell with an effective amount of a compound according to claim 1, or a pharmaceutically acceptable salt or N-oxide thereof.

41. A method for decreasing glycogen concentration in a cell, the method comprising
contacting the cell with an effective amount of a compound according to claim 1, or a pharmaceutically acceptable salt or N-oxide thereof.

42. A method for increasing glucose uptake in a cell, the method comprising
contacting the cell with an effective amount of a compound according to claim 1, or a pharmaceutically acceptable salt or N-oxide thereof.

43. A method for reducing triglyceride levels in a subject, the method comprising
administering to the subject an effective amount of a compound according to claim 1, or a pharmaceutically acceptable salt or N-oxide thereof.

44. A method for treating type II diabetes in a subject, the method comprising administering to the subject an effective amount of a compound according to claim 1, or a pharmaceutically acceptable salt or N-oxide thereof.

45. A method for treating atherosclerosis in a subject, the method comprising administering to the subject an effective amount of a compound according to claim 1, or a pharmaceutically acceptable salt or N-oxide thereof.

46. A labeled conjugate having the structural formula

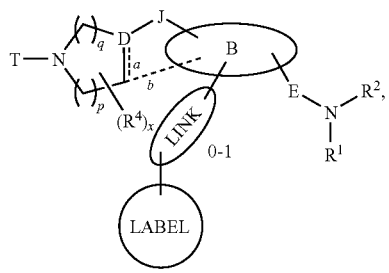

in which the "LINK" moiety is a linker and is optional, and the "LABEL" moiety is a labeling agent, and the

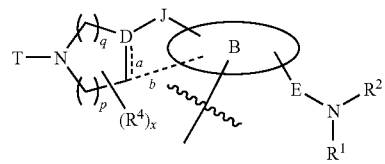

moiety is as described in claim 1.

47. A compound according to claim 25, wherein "B" represents

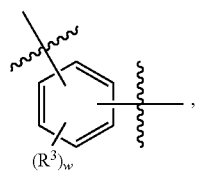

the dotted line denoted by "b" is a single bond, the dotted line denoted by "a" is a bond, k is 0, J is —N($R^{38}$)— and D is a carbon.

48. A compound according to claim 47, wherein w is 0 and v is 0.

49. A compound according to claim 47, wherein E is C(O).

50. A compound according to claim 7, wherein "B" represents

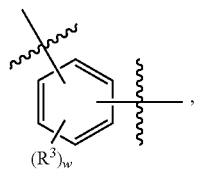

the dotted line denoted by "b" is a single bond, the dotted line denoted by "a" is a bond, k is 0, J is —N($R^{38}$)— and D is a carbon.

51. A compound according to claim 9, wherein "B" represents

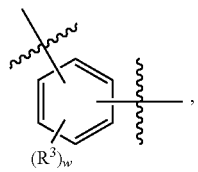

the dotted line denoted by "b" is a single bond, the dotted line denoted by "a" is a bond, k is 0, J is —N($R^{38}$)— and D is a carbon.

52. A compound according to claim 11, wherein "B" represents

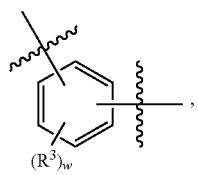

the dotted line denoted by "b" is a single bond, the dotted line denoted by "a" is a bond, k is 0, J is —N($R^{38}$)— and D is a carbon.

53. A compound according to claim 17, wherein "B" represents

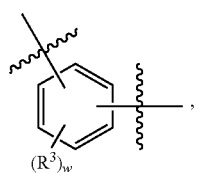

the dotted line denoted by "b" is a single bond, the dotted line denoted by "a" is a bond, k is 0, J is —N($R^{38}$)— and D is a carbon, and $R^2$ is substituted at its 1-position with —($C_0$-$C_3$ alkyl)—Ar, —($C_0$-$C_3$ alkyl)—Het, C(O)—O($C_0$-$C_6$ alkyl), —C(O)—Het, —C(O)—Ar, —S(O)$_2$—Het, —S(O)$_2$—Ar or —S(O)$_2$—O($C_0$-$C_6$ alkyl).

* * * * *